United States Patent
Yamamoto et al.

(10) Patent No.: US 11,786,534 B2
(45) Date of Patent: Oct. 17, 2023

(54) SUBSTITUTED PYRROLO[2,3-D]PYRIMIDINES AS EGFR INHIBITORS

(71) Applicant: TAIHO PHARMACEUTICAL CO., LTD., Chiyoda-ku (JP)

(72) Inventors: Fuyuki Yamamoto, Ibaraki (JP); Takashi Mizutani, Ibaraki (JP); Hidefumi Kasuga, Ibaraki (JP); Hirokazu Fuchida, Ibaraki (JP); Shoki Hara, Ibaraki (JP); Yu Kobayakawa, Ibaraki (JP); Yoshio Ogino, Ibaraki (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 171 days.

(21) Appl. No.: 17/430,208

(22) PCT Filed: Feb. 14, 2020

(86) PCT No.: PCT/JP2020/005684
§ 371 (c)(1),
(2) Date: Aug. 11, 2021

(87) PCT Pub. No.: WO2020/166680
PCT Pub. Date: Aug. 20, 2020

(65) Prior Publication Data
US 2022/0160719 A1    May 26, 2022

(30) Foreign Application Priority Data
Feb. 15, 2019   (JP) .................. 2019-025844

(51) Int. Cl.
| | |
|---|---|
| A61K 31/519 | (2006.01) |
| C07D 487/04 | (2006.01) |
| A61K 31/5377 | (2006.01) |
| A61P 35/00 | (2006.01) |
| C07D 519/00 | (2006.01) |

(52) U.S. Cl.
CPC ........ *A61K 31/5377* (2013.01); *A61K 31/519* (2013.01); *A61P 35/00* (2018.01); *C07D 487/04* (2013.01); *C07D 519/00* (2013.01)

(58) Field of Classification Search
CPC ............................ A61K 31/519; C07D 487/04
USPC ........................ 514/265.1; 544/280
See application file for complete search history.

(56) References Cited

U.S. PATENT DOCUMENTS

| | | |
|---|---|---|
| 2008/0014200 A1 | 1/2008 | Arnold et al. |
| 2008/0267957 A1 | 10/2008 | Arnold et al. |
| 2008/0299113 A1 | 12/2008 | Arnold et al. |
| 2014/0142126 A1 | 5/2014 | Chen et al. |
| 2015/0239897 A1 | 8/2015 | Chen et al. |
| 2016/0375026 A1 | 12/2016 | Chen et al. |
| 2017/0114063 A1 | 4/2017 | Zhang et al. |

FOREIGN PATENT DOCUMENTS

| | | |
|---|---|---|
| WO | WO 2007/075554 A2 | 7/2007 |
| WO | WO 2013/118817 A1 | 8/2013 |
| WO | WO 2014/078578 A1 | 5/2014 |
| WO | WO 2015/178955 A1 | 11/2015 |

OTHER PUBLICATIONS

International Search Report dated May 12, 2020 in PCT/JP2020/005684 filed Feb. 14, 2020, 2 pages.
Kim, E., et al., "Epidermal growth factor receptor biology (IMC-C225)", Current Opinion in Oncology, vol. 13, 2001, pp. 506-513.
Morgillo, F., et al., "Mechanisms of resistance to EGFR-targeted drugs: lung cancer", ESMO Open, vol. 1, 2016, e00060, pp. 1-9.
International Agency for Research on Cancer, WHO, Cancer Fact Sheets, "All cancers", 2018 URL:http://gcc.iarc.fr/today/data/factsheets/cancers/39-All-cancers-fact-sheet.pdf, pp. 1-2.
Ramalingam, S., et al., "Osimertinib as First-Line Treatment of EGFR Mutation-Positive Advanced Non-Small-Cell Lung Cancer", Journal of Clinical Oncology, vol. 36, No. 9, 2018, pp. 841-849, 11 total pages.
Doebele, R., et al., "New strategies to overcome limitations of reversible EGFR tyrosine kinase inhibitor therapy in non-small cell lung cancer", Lung Cancer, vol. 69, 2010, pp. 1-12.
Pao, W., et al., "Rational, biologically based treatment of EGFR-mutant non-small-cell lung cancer", Nature Reviews Cancer, vol. 10, 2010, pp. 760-774.
Lacouture, M., "Mechanisms of cutaneous toxicities to EGFR inhibitors", Nature Reviews Cancer, vol. 6, 2006, pp. 803-812.

*Primary Examiner* — Douglas M Willis
(74) *Attorney, Agent, or Firm* — Oblon, McClelland, Maier & Neustadt, L.L.P.

(57) ABSTRACT

The present invention provides a novel compound inhibiting EGFR or a salt of the compound. According to one embodiment of the present invention, provided is a compound represented by general formula (I) or a pharmaceutically acceptable salt thereof.

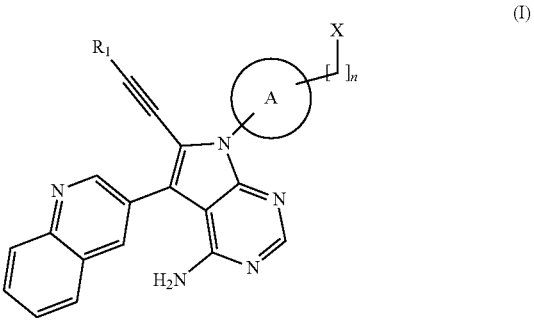

(I)

14 Claims, No Drawings
Specification includes a Sequence Listing.

SUBSTITUTED PYRROLO[2,3-D]PYRIMIDINES AS EGFR INHIBITORS

CROSS-REFERENCE TO RELATED APPLICATIONS

The present application is a National Stage application PCT/JP2020/005684, filed Feb. 14, 2020, which claims priority to JP 2019-025844, filed Feb. 15, 2019, the entire contents of both applications are incorporated hereby by reference.

TECHNICAL FIELD

The present invention relates to substituted compounds having an inhibitory effect against the epidermal growth factor receptor (EGFR) and a pharmaceutical composition comprising such a compound as an active ingredient.

BACKGROUND ART

EGFR is a receptor-type tyrosine kinase and exerts its physiological functions in normal tissue upon binding to epidemal growth factor (EGF) as a ligand. In the epidermal tissue, EGFR contributes to growth and apoptosis inhibition, etc. (Non-patent Literature 1).

Moreover, EGFR is also a kind of oncogene, and amplification of the EGFR gene and high expression and/or mutation of its protein have been known in various cancer types including head and neck cancer, breast cancer, large bowel cancer, esophageal cancer, pancreatic cancer, lung cancer, ovarian cancer, renal cancer, bladder cancer, skin cancer, brain tumor and so on (Non-patent Literature 2). In the countries of East Asia and the US and Europe, approximately 90 to 105 patients per 100,000 population die from cancer every year; and hence cancer ranks high as a cause of death (Non-patent Literature 3). In particular, the number of deaths caused by lung cancer has reached approximately 1,400,000 per year all over the world, and there has been a demand for the development of effective therapy for non-small cell lung cancer because it accounts for over 80% of lung cancer cases (Non-patent Literature 4).

In recent years, genes responsible for these cancers are having been identified, and EGFR gene mutation is one of them and provides an active mutated EGFR protein. Such an active mutated EGFR protein comprises, for example, a partial deletion (e.g., deletion ammo acids 746 to 750) in exon 19 (EGFR (Del19)) or a leucine to arginine mutation in the amino acid at position 858 (EGFR (L858R)), etc., and such a mutation has been reported, for example, in 20% to 40% of non-small cell lung cancer cases in Japan and also in 10% to 15% of non-small cell lung cancer cases in the US and Europe. Since non-small cell lung cancer having these mutations is highly susceptible to gefitnib (trade name: Iressa®) and erlotinib (trade name: Tarceva®), which are drugs inhibiting the kinase activity of EGFR (i.e., EGFR inhibitors), these drugs are used as therapeutic agents in Japan and the US and Europe. However, once 6 to 12 months have passed after the initiation of drug use, resistance to gefitinib and erlotinib will be acquired, and their therapeutic effects will be weakened. Thus, this acquired resistance has become a serious problem in the treatment of non-small cell lung cancer having highly susceptible mutated EGFR. It has been indicated that about 50% of this acquired resistance is due to the occurrence of a resistant mutated EGFR protein (EGFR (Del19/T790M) or EGFR (T790M/L858R)) having a second mutation in the EGFR gene which results in a change from threonine to methionine in the amino acid at position 790; and hence it has become an important problem to develop a therapeutic agent which is also effective against non-small cell lung cancer having this drug -resistant mutated EGFR (Non-patent Literature 5).

As a result of the subsequent development of EGFR inhibitors effective against the resistant mutated EGFR protein (EGFR (Del19/T790M) or EGFR (T790M/L858R)), osimertinib (trade name: Tagrisso®) was approved in Japan and the US and Europe, and has now been clinically used as a secondary therapeutic agent prescribed following gefitinib or erlotinib which is a primary therapeutic agent for EGFR-positive lung cancer. However, once about 10 months have passed after the use of osimertinib, the effect will be weakened again, thus indicating that resistance will be acquired. Genetic analysis has indicated the occurrence of EGFR (Del19/T790M/C797S) or EGFR (T790M/C797S/L858R) further having a change from cysteine to serine in the amino acid at position 797 as an osimertinib-resistant mutation. For this reason, there has been a demand for the development of therapy which is also effective against non-small cell lung cancer having EGFR triple mutations where an activating mutation and two resistance mutations have occurred (Non-patent Literature 6).

Recently, the therapeutic system for osimertinib has been amended such that osimertinib is also used as a primary therapeutic agent in clinical practice, in addition to its conventional use as a secondary therapeutic agent for EGFR-positive non-small cell lung cancer. In this case, there has been reported the occurrence of double mutated EGFR (Del19/C797S) or EGFR (L858R/C797S) having not only an activating mutation but also a serine mutation in the amino acid at position 797 as a new resistance mutation. Thus, to exert an effect on EGFR-positive lung cancer cells which have been resistant or refractory to osimertinib, there is a need to develop EGFR inbibitors which inhibit these double mutated resistant EGFR proteins (Non-patent Literature 7).

CITATION LIST

Patent Literature

Patent Literature 1: WO2013/118817

Non-Patent Literature

Non-patent Literature 1: Nature Rev. Cancer, vol. 6, pp, 803-811 (2006)

Non-patent Literature 2: Current Opinion in Oncology, vol. 13, pp. 506-513 (2001)

Non-patent Literature 3: international Agency for Research on Cancer, WHO, Cancer Fact Sheets, "All Cancers" (2018) [search on Feb. 13, 2019], Internet <URL: http://gco.iarc.fr/today/data/factsheets/cancers/39-All-cancers-fact-sheet.pdf>

Non-patent Literature 4: Lung Cancer, vol. 69, pp. 1-12 (2010)

Non-patent Literature 5: Nature Rev. Cancer, vol. 10, pp. 760-774 (2010)

Non-patent Literature 6: ESMO Open, vol. 1, e000060 (2016)

Non-patent Literature 7: J. Clin. Oncol., vol. 36, pp. 841-849 (2018)

SUMMARY OF THE INVENTION

Problem to be Solved by the Invention

Under these circumstances surrounding the therapeutic system, there has been a demand for the development of a drug effective in two cases of resistance mutations where osimertinib is used in secondary therapy and where osimertinib is used in primary therapy. Namely, upon administration of a drug whose inhibitory activity against wild-type EGFR is weaker in comparison with its inhibitory activity against cells expressing erlotinib-, gefitinib- and osimertinib-resistant mutated EGFR having not only an activating mutation but also a methionine mutation in the amino acid at position 790 and a serine mutation in the amino acid at position 797 or cells expressing osimertinib-resistant mutated EGFR having not only an activating mutation but also a serine mutation in the amino acid at position 797, such a drug can be expected to suppress the 2rowth of non-small cell lung cancer cells having drug-resistant mutated EGFR at a dose where side effects in the skin or digestive tract do not appear strongly.

As described above, EGFR inhibitors are expected to be effective in cancer therapy, but currently are not clinically effective enough in cancer having both an activating mutation and an osimertinib-resistant mutation.

Under the circumstances as stated above, there is a demand for a novel compound or a salt thereof, which inhibits EGFR. Moreover, there is also a demand for a novel compound or a salt thereof, which inhibits mutated EGFR, such as EGFR (Del19/C797S), EGFR (L858R/C797S), EGFR (Del19/T790M/C797S) or EGFR (L858R/T790M/C797S), but has weak inhibitory activity against wild-type EGFR (WT).

BRIEF SUMMARY OF THE INVENTION

As a result of extensive and intensive efforts, the inventors of the present invention have found pyrimidine-based novel compounds represented by formula (I) described later (7H-pyrrolo[2,3-d]pyrimidine-4-amine derivatives). These compounds are novel compounds characterized by having pyrrolo[2,3-d]pyrimidine as their skeletal structure whose 5-position is substituted with a quinoline ring and whose 7-position is substituted with a bicyclo ring.

Namely, one embodiment of the present invention provides [1] to [16] shown below.

[1]

A compound represented by the following general formula (I):

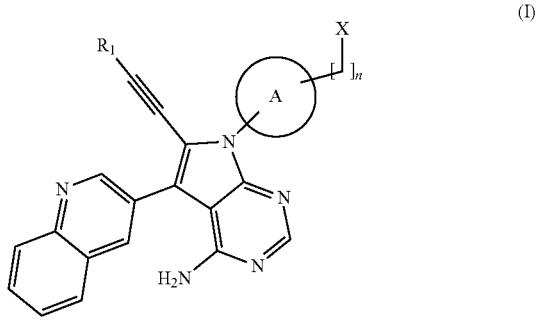

wherein
$R^1$ is a hydrogen atom or an optionally substituted C1-C3 alkyl group;
X is $NR^2R^3$, $OR^4$ or an optionally substituted monocyclic or polycyclic saturated or unsaturated heterocyclic group;
$R^2$ is a hydrogen atom or an optionally substituted C1-C6 alkyl group;
$R^3$ is a hydrogen atom, $C(=O)R^5$, $C(=S)R^6$, $S(=O)_2R^7$, an optionally substituted C1-C6 alkyl group, or an optionally substituted C3-C7 cycloalkyl group;
$R^4$ is a hydrogen atom, an optionally substituted C1-C6 alkyl group, an optionally substituted C3-C7 cycloalkyl group, or an optionally substituted carbonylamino group;
$R^5$ is an optionally substituted C1-C6 alky group, an optionally substituted C3-C7 cycloalkyl group, an optionally substituted C1-C6 alktaxy group, an optionally substituted amino group, an optionally substituted 4- to 10-membered monocyclic or polycyclic saturated heterocyclic group, an optionally substituted 5- to 10-membered monocyclic or polycyclic unsaturated. heterocyclic group, or an optionally substituted 6- to 10-membered monocyclic or polycyclic aromatic hydrocarbon group;
$R^6$ is a hydrogen atom, an optionally substituted C1-C6 alkyl group, an optionally substituted. C1-C6 mono- or di-alkylamino group, an optionally substituted C3-C7 cycloalkyl group, or an optionally substituted 4- to 10-membered monocyclic or polycyclic saturated heterocyclic group having 1 to 4 heteroatoms selected from a nitrogen atom, an oxygen atom and a sulfur atom;
$R^7$ is an optionally substituted C1-C6 alkyl group, an optionally substituted C3-C7 cycloalkyl group, an optionally substituted 5- to 10-membered saturated or unsaturated heterocyclic group, or an optionally substituted 6- to 10-membered aromatic hydrocarbon group;
the ring A is bicyclo[2.2.1]heptane or bicyclo[2.2.2]octane; and
n represents an integer of 0 to 3;
or a pharmaceutically acceptable salt thereof.

[2]

The compound or pharmaceutically acceptable salt thereof according to [1] above, wherein $R^1$ is a hydrogen atom or a C1-C3 alkyl group.

[3]

The compound or pharmaceutically acceptable salt thereof according to [1] or [2] above, wherein X is $NR^2R^3$, $OR^4$ or a 5- to 7-membered monocyclic saturated or unsaturated heterocyclic group having 1 to 3 heteroatoms selected from a nitrogen atom, an oxygen atom and a sulfur atom;
$R^2$ is a hydrogen atom or a C1-C6 alkyl group;
$R^3$ is $C(=O)R^5$, $C(=S)R^6$ or a C1-C6 alkyl group (which may have, as a substituent, a cyan group, a halogen atom or a 5- to 7-membered monocyclic unsaturated heterocyclic group having 1 to 3 heteroatoms selected from a nitrogen atom, an oxygen atom and a sulfur atom);
$R^4$ is a hydrogen atom;
$R^5$ is an optionally sastituted C1-C6 alkyl group, a C1-C6 alkoxy group, a C1-C6 mono- or di-alkylamino group, an optionally substituted 5- to 10-membered monocyclic or polycyclic unsaturated heterocyclic group, or a 6- to 10-membered monocyclic or polycyclic aromatic hydrocarbon group; and
$R^6$ is a C1-C6 mono- or di-alkylamino group, or a 4- to 10-membered monocyclic or polycyclic saturated heterocyclic group having 1 to 4 heteroatoms selected from a nitrogen atom, an oxygen atom and a sulfur atom, which may have a C1-C6 alkyl group.

[4]
The compound or pharmaceutically acceptable salt thereof according to any one of [1] to [3] above, wherein n is 0 or 1.

[5]
The compound or pharmaceutically acceptable salt thereof according to any one of to [1] to [4] above, wherein $R^1$ is a hydrogen atom.

[6]
The compound or pharmaceutically acceptable salt thereof according to any one of [1] to [5] above, wherein X is $NR^2R^3$ or a 5- to 7-membered monocyclic saturated or unsaturated heterocyclic group having 1 to 3 heteroatoms selected from a nitrogen atom, an oxygen atom and a sulfur atom;
$R^2$ is a hydrogen atom;
$R^3$ is C(=O)$R^5$; and
$R^5$ is an optionally substituted C1-C6 alkyl group, a C1-C6 alkoxy group, a C1-C6 mono- or di-alkylamino group, an optionally substituted 5- to 10-membered monocyclic or polycyclic unsaturated heterocyclic group, or a 6- to 10-membered monocyclic or polycyclic aromatic hydrocarbon group.

[7]
The compound or pharmaceutically acceptable salt thereof according to any one of [1] to [6] above, wherein X is $NR^2R^5$ or a 5- to 7-membered monocyclic saturated heterocyclic group haying 1 to 3 heteroatoms selected from a nitrogen atom, an oxygen atom and a sulfur atom;
$R^2$ is a hydrogen atom;
$R^3$ is C(=O)$R^5$; and
$R^5$ is a C1-C6 alkyl group which may have a halogen atom, or a 5- to 10-membered monocyclic or polycyclic fully unsaturated or partially saturated heterocyclic group having 1 to 4 heteroatoms selected from a nitrogen atom, an oxygen atom and a sulfur atom, which may have a C1-C6 alkyl group.

[8]
The compound or pharmaceutically acceptable salt thereof according to any one of [1] to [7] above, wherein the ring A is bicyclo[2.2.1]heptane.

[9]
The compound or pharmaceutically acceptable salt thereof according to any one of [1] to [8] above, wherein n is 0.

[10]
The compound or pharmaceutically acceptable salt thereof according to any one of [1] to [9] above, wherein the substituents are each selected from a halogen atom, a cyano group, a nitro group, an amino group, a hydroxyl group, an alkyl group, a haloalkyl group, a cycloalkyl group, an aralkyl group, an alkoxy group, a methylsulfonyl group, an alkoxyalkyl group, a fluoromethoxy group, a mono- or di-alkylamino group, a carbonylamino group, an oxo group, a carboxyl group, an alkoxycarbonyl group, a saturated or unsaturated heterocyclic group and an aromatic hydrocarbon group.

[10-1]
The compound or pharmaceutically acceptable salt thereof according to any one of [1] to [9] above, wherein the substituents are each selected from a halogen atom, a cyano group, a nitro group, an amino group, a hydroxyl group, an alkyl group, a haloalkyl group, a cycloalkyl group, an aralkyl group, an alkoxy group, a methylsulfonyl group, an alkoxyalkyl group, a hydroxyalkyl group, a fluoromethoxy group, a mono- or di-alkylamino group, a mono- or di-alkylaminoalkyl group, a carbonylamino group, an oxo group, an oxide group, a carboxyl group, an alkoxycarbonyl group, a phosphine oxide group, a saturated or unsaturated heterocyclic group, a heterocyclic alkyl group and an aromatic hydrocarbon group.

[11]
A compound selected from the following group of compounds:
(1) 6-ethynyl-7-(4-morpholinobicyclo[2.2.1]heptan-1-yl)-5-(quinolin-3-yl)-7H -pyrrolo[2,3-d]pyrimidine-4-amine,
(2) N-(4-(4-amino-6-ethynyl-5-(quinolin-3-yl)-7H-pyrrolo[2,3-d]pyrimidin-7-yl)bicyclo[2.2.1]heptan-1-yl)-1-methyl-1H-pyrazole-5-carboxamide,
(3) N-(4-(4-amino-6-ethynyl-5-(quinolin-3-yl)-7H-pyrrolo[2,3-d]pyrimidin-7-yl)bicyclo[2.2.1]heptan-1-yl)-2,2-difluoroacetamide,
(4) N-(4-(4-amino-6-ethynyl-5-(quinolin-3-yl)-7H-pyrrolo[2,3-d]pyrimidin-7-yl)bicyclo[2.2.1]heptan-1-yl)-5-methyl-1,2,4-oxadiazole-3-carboxamide,
(5) N-(4-(4-amino-6-ethynyl-5-(quinolin-3-yl)-7H-pyrrolo[2,3-d]pyrimidin-7-yl)bicyclo[2.2.1]heptan-1-yl)-5-methylpyrazine-2-carboxamide,
(6) N-(4-(4-amino-6-ethynyl-5-(quinolin-3-yl)-7H-pyrrolo[2,3-d]pyrimidin-7-yl)bicyclo[2.2.1]heptan-1-yl) oxazole-2-carboxamide,
(7) N-(4-(4-amino-6-ethynyl-5-(quinolin-3-yl)-7H-pyrrolo[2,3-d]pyrimidin-7-yl)bicyclo[2.2.1]heptan-1-yl) pyrazine-2-carboxamide, and
(8) N-(4-(4-amino-6-ethynyl-5-(quinolin-3-yl)-7H-pyrrolo[2,3-d]pyrimidin-7-yl)bicyclo[2.2.1]heptan-1-yl) pyridazine-3-carboxamide;
or a pharmaceutically acceptable salt thereof.

[11-1]
A compound selected from the following group of compounds:
(1) 6-ethynyl-7-(4-morpholinobicyclo[2.2.1]heptan-1-yl)-5-(quinolin-3-yl)-7H -pyrrolo[2,3-d]pyrimidine-4-amine,
(2) N-(4-(4-amino-6-ethynyl-5-(quinolin-3-yl)-7H-pyrrolo[2,3-d]pyrimidin-7-yl)bicyclo[2.2.1]heptan-1-yl)-1-methyl-1H-pyrazole-5-carboxamide,
(3) N-(4-(4-amino-6-ethynyl-5-(quinolin-3-yl)-7H-pyrrolo[2,3-d]pyrimidin-7-yl)bicyclo[2.2.1]heptan-1-yl)-2,2-difluoroacetamide,
(4) N-(4-(4-amino-6-ethynyl-5-(quinolin-3-yl)-7H-pyrrolo[2,3-d]pyrimidin-7-yl)bicyclo[2.2.1]heptan-1-yl)-5-methyl-1,2,4-oxadiazole-3-carboxamide,
(5) N-(4-(4-amino-6-ethynyl-5-(quinolin-3-yl)-7H-pyrrolo[2,3-d]pyrimidin-7-yl)bicyclo[2.2.1]heptan-1-yl)-5-methylpyrazine-2-carboxamide,
(6) N-(4-(4-amino-6-ethynyl-5-(quinolin-3-yl)-7H-pyrrolo[2,3-d]pyrimidin-7-yl)bicyclo[2.2.1]heptan-1-yl) oxazole-2-carboxamide,
(7) N-(4-(4-amino-6-ethynyl-5-(quinolin-3-yl)-7H-pyrrolo[2,3-d]pyrimidin-7-yl)bicyclo[2.2.1]heptan-1-yl) pyrazine-2-carboxamide,
(8) N-(4-(4-amino-6-ethynyl-5-(quinolin-3-yl)-7H-pyrrolo[2,3-d]pyrimidin-7-yl)bicyclo[2.2.1]heptan-1-yl) pyridazine-3-carboxamide,
(9) N-(4-(4-amino-6-ethynyl-5-(quinolin-3-yl)-7H-pyrrolo[2,3-d]pyrimidin-7-yl)bicyclo[2.2.1]heptan-1-yl) pyrimidine-5-carboxamide,
(10) N-(4-(4-amino-6-ethynyl-5-(quinolin-3-yl)-7H-pyrrolo[2,3-d]pyrimidin-7-yl)bicyclo[2.2.1]heptan-1-yl)-1-cyclopropyl-1H-pyrazole-5-carboxamide, and

(11) N-(4-(4-amino-6-ethynyl-5-(quinolin-3-yl)-7H-pyrrolo[2,3-d]pyrimidin-7-yl)bicyclo[2.2.1]heptan-1-yl)isoxazole-5-carboxamide;

or a pharmaceutically acceptable salt thereof.

[12]
An antitumor agent comprising the compound or pharmaceutically acceptable salt thereof according to any one of [1] to [11-1] above as an active ingredient.

[13]
A pharmaceutical composition comprising the compound or pharmaceutically acceptable salt thereof according to any one of [1] to [11-1] above and a pharmaceutically acceptable carrier.

[14]
A method for the treatment of tumor, comprising administering the compound or pharmaceutically acceptable salt thereof according to any one of [1] to [11-1] above.

[14-1]
A method for the treatment of tumor, which comprises administering an effective amount of the compound or pharmaceutically acceptable salt thereof according to any one of [1] to [11-1] above to a subject in need thereof.

[15]
The compound or pharmaceutically acceptable salt thereof according to any one of [1] to [11-1] above for use in the treatment of tumor.

[16]
The use of the compound or pharmaceutically acceptable salt thereof according to any one of [1] to [11-1] above for the manufacture of an antitumor agent.

Effects of the Invention

According to one embodiment of the present invention, there is provided a novel compound represented by the above general formula (I) or a salt thereof, which inhibits EGFR.

DESCRIPTION OF EMBODIMENTS

The compound of the present invention represented by the following formula (I) has pyrrolo[2,3-d]pyrimidine as its skeletal structure and is a novel compound:

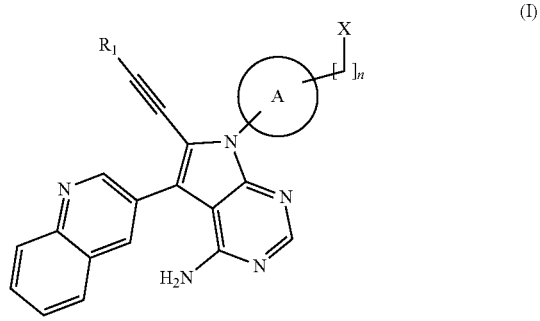

wherein $R^1$ is a hydrogen atom or an optionally substituted C1-C3 alkyl group;

X is $NR^2R^3$, $OR^4$ or an optionally substituted monocyclic or polycyclic saturated or unsaturated heterocyclic group;

$R^2$ is a hydrogen atom or an optionally substituted C1-C6 alkyl group;

$R^3$ is a hydrogen atom, $C(=O)R^5$, $C(=S)R^6$, $S(=O)_2R^7$, an optionally substituted C1-C6 alkyl group, or an optionally substituted C3-C7 cycloalkyl group;

$R^4$ is a hydrogen atom, an optionally substituted C1-C6 alkyl group, an optionally substituted C3-C7 cycloalkyl group, or an optionally substituted carbonylamino aroup;

$R^5$ is an optionally substituted C1-C6 alkyl group, an optionally substituted C3-C7 cycloalkyl group, an optionally substituted C1-C6 alkoxy group, an optionally substituted amino group, an optionally substituted 4- to 10-membered monocyclic or polycyclic saturated heterocyclic group, an optionally substituted 5- to 10-membered monocyclic polycyclic unsaturated heterocyclic group, or an optionally substituted 6- to 10-membered monocyclic polycyclic aromatic hydrocarbon group;

$R^6$ is a hydrogen atom, an optionally substituted C1-C6 alkyl group, an optionally substituted. C1-C6 mono- or di-alkylamino group, an optionally substituted C3-C7 cycloalkyl group, or an optionally substituted 4- to 10-membered monocyclic or polycyclic saturated heterocyclic group having 1 to 4 heteroatoms selected from a nitrogen atom, an oxygen atom and a sulfur atom;

$R^7$ is an optionally substituted C1-C6 alkyl group, an optionally substituted C3-C7 cycloalkyl group, an optionally substituted 5- to 10-membered saturated or unsaturated heterocyclic group, or an optionally substituted 6- to 10-membered aromatic hydrocarbon group;

the ring A is bicyclo[2.2.1]heptane or bicyclo[2.2.2]octane; and n represents an integer of 0 to 3,

[Definitions of Substituents]

As used herein, the term "substituent" is intended to include, unless otherwise specified, a hydrogen atom, a halogen atom, a cyano group, a nitro group, an amino group, a hydroxyl group, an alkyl group, a haloalkyl group, a cycloalkyl group, an aralkyl group, an alkoxy group, a methylsulfonyl group, an alkoxyalkyl group, a fluoromethoxy group, a mono- or di-alkylamino group, a carbonylamino group, an oxo group, a carboxyl group, an alkoxycarbonyl group, a saturated or unsaturated heterocyclic group, an aromatic hydrocarbon group and so on, by way of example. In cases where the above substituents are present, the number of these substituents is typically 1, 2 or 3, preferably 1 or 2, and most preferably 1 unless otherwise specified.

In one embodiment of the present invention, substituents may be selected from a halogen atom, a cyano group, a nitro group, an amino group, a hydroxyl group, an alkyl group, a haloalkyl group, a cycloalkyl group, an aralkyl group, an alkoxy group, a methylsulfonyl group, an alkoxyalkyl group, a hydroxyalkyl group, a fluoromethoxy group, a mono- or di-alkylamino group, a mono- or di-alkylaminoalkyl group, a carbonylamino group, an oxo group, an oxide group, a carboxyl group, an alkoxycarbonyl group, a phosphine oxide group, a saturated or unsaturated heterocyclic group, a heterocyclic alkyl group and an aromatic hydrocarbon group.

As used herein, the term "halogen atom" is intended to specifically include as chlorine atom, a bromine atom, a fluorine atom and an iodine atom, with a chlorine atom and a fluorine atom being preferred.

As used herein, the term "alkyl group" refers to a linear or branched saturated hydrocarbon group, and specific examples include a methyl group, an ethyl group, a n-propyl group, an isopropyl group, a n-butyl group, an isobutyl group, a sec-butyl group, a tert-butyl group, a pentyl group, a hexyl group, etc.

As used herein, the term "haloalkyl group" refers to a linear or branched saturated hydrocarbon group whose one or more hydrogen atoms are replaced with halogen atoms as defined above, and specific examples include a monofluoromethyl group, a difluoromethyl group, a trifluoromethyl group, a 1-fluoroethyl group, a 2-fluoroethyl group, a 1,1-difluoroethyl group, a 1,2-difluoroethyl group, a 2,2-difluoroethyl group, a 2,2,2-trifluoroethyl group, etc.

As used herein, the term "aralkyl group" refers to an alkyl group whose one hydrogen atom is replaced with an aryl group, and specific examples include a benzyl group (i.e., a phenylmethyl group), a phenethyl group (i.e., a phenylethyl group), a naphthylmethyl group and a naphthylethyl group, etc.

As used herein, the term "alkoxy group" refers to an oxy group having an alkyl group as defined above, and specific examples include a methoxy group, an ethoxy group, a n-propoxy group, an isopropoxy group, a tert-butoxy group, etc.

As used herein, the term "cycloalkyl group" refers to a monocyclic or polycyclic saturated hydrocarbon group, and specific examples include a cyclopropyl group, a cyclobutyl group, a cyclopentyl group, a cyclohexyl group, a cycloheptyl group, etc.

As used herein, the term "mono-C1-C6 alkylamino group" refers to an amino group whose one hydrogen atom is replaced with a linear or branched hydrocarbon group containing 1 to 6 carbon atoms, and specific examples include a methylamino group, an ethylamino group, a n-propylamino group, an isopropylamino group, a n-butylamino group, an isobutylamino group, a sec-butylamino group, a tert-butylamino group, a pentylamino group, a hexylamino group, etc.

As used herein, the term "di-C1-C6 alkylamino group" refers to an amino group whose two hydrogen atoms are each replaced with a linear or branched hydrocarbon group containing 1 to 6 carbon atoms, and specific examples include a dimethylamino group, a diethylamino group, an ethylmethylamino group, etc.

As used herein, the term "mono- or di-alkylaminoatkyl group" refers to an alkyl group as defined above which has at least one mono- or di-alkylamino group, and examples include mono- or di-C1-C6 alkylamino-C1-C6 alkyl groups such as a methylaminomethyl group, a methylaminoethyl group, a ethylaminomethyl group, an ethylaminopropyl group, a dimethylaminomethyl group, etc.

As used hereiu, the term "alkoxyalkv group" refers to an alkyl group as defined above which has at least one alkoxy group as defined above, and examples include C1-C6 alkoxy-C1-C6 alkyl groups such as a methoxymethyl group, an ethoxyethyl group, a methoxyethyl group (e.g., a 2-methoxyethyl group), a methoxypropyl group, etc.

As used herein, the term "phosphine oxide group" refers to a phosphonyl group having at least one oxide group as defined above (e.g., a group represented by —P(=O)R$_2$ (wherein each R represents a halogen atom, an alkyl group or an aryl group)), and examples include a methylphosphine oxide group, a dimethylphosphine oxide group and a diphenylphosphine oxide group.

As used herein, the term "saturated heterocyclic group" refers to a monocyclic or polycyclic fully saturated heterocyclic group having at least one heteroatom preferably 1 to 5, more preferably 1 to 3 heteroatoms) selected from a nitrogen atom, an oxygen atom and a sulfur atom, and specific examples include an azeridinyl group, a pyrrolidinyl group, a piperidinyl group, a piperazinyl group, a hexamethyleneimino group, a morpholino group, a thiomorpholino group, a homopiperazinyl group, an oxetanyl group, a tetrahydrofuranyl group, a tetrahydropyranyl group, 2,6-diazaspiro[3,3]heptane, etc.

As used herein, the term "unsaturated heterocyclic group" refers to a monocyclic or polycyclic fully unsaturated or partially saturated heterocyclic group having at least one heteroatom (preferably 1 to 5, more preferably 1 to 3 heteroatoms) selected from a nitrogen atom, an oxygen atom and a sulfur atom, and specific examples include fully unsaturated heterocyclic groups such as a pyrrolyl group, an imidazolyl group, a pyrazolyl group, a triazolyl group, a tetrazolyl group, a furanyl group, an oxazolyl group, an isoxazolyl group (or an isooxazolyl group), an oxadiazolyl group, a thiophenyl group, a thiazolyl group, an isothiazolyl group, a thiadiazolyl group, a pyridinyl group, a pyrimidinyl group, a pyrazinyl group, a pyridazinyl group, an indolyl group, an isoindolyl group, an indazolyl group, a benzoimidazolyl group, a benzotriazolyl group, an azaindolyl group, a pyrrolopyridinyl group, an imidazopyridinyl group, an imidazopyrazinyl group, a pyrazolopyridinyl group, a triazolopyridinyl group, a pyrrolopyrimidinyl group, an imidazopyrimidinyl group, a pyrazolopyrimidinyl group, a benzofuranyl group, a benzoxazolyl group, a benzothiophenyl group, a benzothiazolyl group, as benzofuranyl group, a quinolyl group, as isoquinolyl group, a quinazolinyl group, a quinoxalyl group, etc., as well as partially saturated heterocyclic groups such as an indolinyl group, a methylenedioxyphenyl group, an ethylenedioxyphenyl group, a dihydrobenzofuranyl group, etc.

As used herein, the term "aromatic hydrocarbon group" refers to a cyclic substituent having unsaturated bonds and consisting of carbons and hydrogens, whose cyclic π electron system contains 4e+2 electrons (wherein e is an integer of 1 or more), and specific examples include a phenyl group, naphthyl group, a tetrahydronaphthyl group, etc.

As used herein, the term "heterocyclic alkyl group" refers to an alkyl group as defined above, which has a saturated or unsaturated heterocyclic ring as defined above, and specific examples include a pyridylmethyl group, a pyrrolidylmethyl group, a morpholinomethyl group, etc.

As used herein, the term "bicyclo ring" refers to a polycyclic (e.g., bicyclic, tricyclic) saturated hydrocarbon, in which at least two (e.g., two or three) saturated hydrocarbon rings each share at least two carbon atoms with their tdiacent ring, and specific examples include bicyclo[3.2.1]octane, bicyclo[3.1.1]heptane, bicyclo[2.2.2]-octane, bicyclo[2.2.1]heptane, bicyclo[2.2.1]hexane, bicyclo[1.1.1]pentane, etc., with bicyclo[2.2.2]octane and bicyclo[2.2.1]heptane being preferred.

As used herein, the term "spiro ring" refers to a bicyclic organic compound having a ring bonded to only one atom, and examples include spiro[4.5]decane, 6-oxa -3-azabicyclo [3.2.1]heptane, etc.

In the compound of the present invention represented by general formula (I), $R^1$ is "a hydrogen atom or a C1-C3 alkyl group."

The "C1-C3 alkyl group" represented by $R^1$ is preferably a methyl group, an ethyl group, a n-propyl group or an isopropyl group, and is more preferably a methyl group.

$R^1$ is preferably a hydrogen atom or a methyl group, and is most preferably hydrogen atom.

As used herein, the expression "CA-CB" appearing in the definitions of the groups is intended to mean that the number of carbon atoms is A to B. For example, the expression "C1-C6 alkyl group" means an alkyl group containing 1 to 6 carbon atoms, while the expression "C6-C10 aromatic hydrocarbon group" means an aromatic hydrocarbon group containing 6 to 10 carbon atoms, Likewise, the expression "A- to B-membered" is intended to mean that the number of ring-constituting atoms (i.e., the number of ring members) is A to B. For example, the expression "4- to 10-membered saturated heterocyclic group" means a saturated heterocyclic group containing 4 to 10 ring members.

In the compound of the present invention represented by general formula (I), the ring A is bicyclo[2.2.1]heptane or bicyclo[2.2.2]octane, and is preferably bicyclo[2.2.1]heptane.

In the compound of the present invention represented by general formula (I), the ring A may be bonded in any form. In the case of bicyclo[2.2]heptane, the following patterns are possible, by way of example. Preferred is (1).

(1)
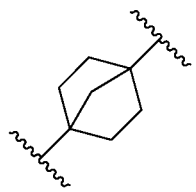

(2)
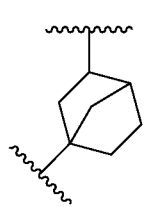

(3)
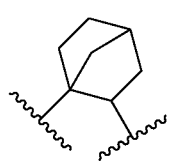

(4)
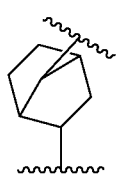

(5)
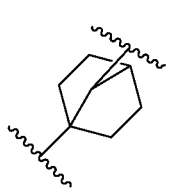

(6)
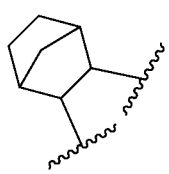

(7)
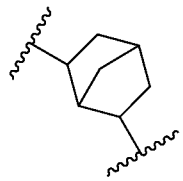

(8)
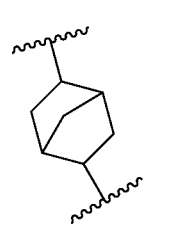

In the case of bicyclo[2.2.2]octane, the following patterns are possible, by way of example. Preferred is (9).

(9)
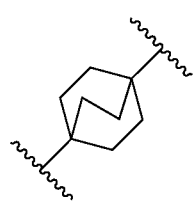

(10)
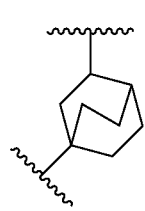

(11)
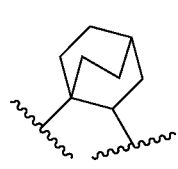

(12)
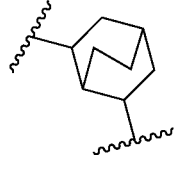

(13)
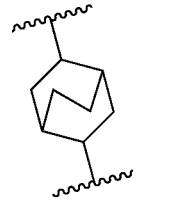

In the compound or the present invention represented by general formula (I), X is $NR^2R^3$, $OR^4$ or an optionally substituted monocyclic or polycyclic saturated or unsaturated heterocyclic group.

A "monocyclic or polycyclic saturated or unsaturated heterocyclic group" in the "optionally substituted monocyclic or polycyclic saturated or unsaturated heterocyclic group" represented by X is preferably a 5- to 7-membered monocyclic saturated or unsaturated heterocyclic group having 1 to 3 heteroatoms selected from a nitrogen atom, an oxygen atom and a sulfur atom. More preferred is a pyridinyl group, a pyrimidinyl group, a piperazinyl group, piperazyl group, a morpholino group, an azetidinyl group, a pyrrolidinyl group, a piperazinyl group, 6-oxa-3-azabicyclo[3.1.1]heptane or 6-oxa-3-azabicyclo[3.2.1]heptane, more preferred is a morpholino group or a piperazinyl group, and more preferred is a morpholino group.

A "substituent" on the "optionally substituted monocyclic or polycyclic saturated or unsaturated heterocyclic group" represented by X is preferably a substituent as defined above. More preferred is an oxo group or a C1-C6 alkyl group, and more preferred is an oxo group or a methyl group.

The "optionally substituted monocyclic or polycyclic saturated or unsaturated heterocyclic group" represented by X is preferably a 5- to 7-membered monocyclic saturated or unsaturated heterocyclic group having 1 to 3 heteroatoms selected from a nitrogen atom, an oxygen atom and a sulfur atom, as exemplified by a pyridinyl group, pyrimidinyl group, a pyrazinyl group, a piperazinyl group, a 1-methyl-2-oxopiperazinyl group, a morpholino group, an azetidinyl group, a pyrrolidinyl group, a piperazinyl group, 6-oxa-3-azabicyclo[3.1.1]heptane, 6-oxa-3-azabicyclo[3.2.1]heptane, or the piperazinyl-based substithent represented by the following formula:

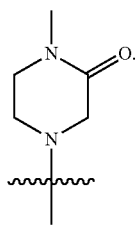 [SMILES: *N1CCN(C)C(=O)C1]

More preferred is a piperazinyl group, a morpholino group or the piperazinyl-based substituent represented by the above formula, and more preferred is a morpholino group.

X is preferably $NR^2R^3$, $OR^4$ or a 5- to 7-membered monocycle saturated or unsaturated heterocyclic group having 1 to 3 heteroatoms selected from a nitrogen atom, an oxygen atom and a sulfur atom. More preferred is $NR^2R^3$ or a 5- to 7-membered monocyclic saturated of unsaturated heterocyclic group having 1 to 3 heteroatoms selected from a nitrogen atom, an oxygen atom and a sulfur atom, more preferred is $NR^2R^3$ or a 5- to 7-membered monocycle saturated heterocyclic group having 1 to 3 heteroatoms selected from a nitrogen atom, an oxygen atom and a sulfur atom, and more preferred is $NR^2R^3$.

In the compound of the present invention represented by general formula (I), $R^2$ is a hydrogen atom or an optionally substituted C1-C6 alkyl group.

A "C1-C6 alkyl group" in the "optionally substituted C1-C6 alkyl group" represented by $R^2$ is preferably a methyl group, an ethyl group, a n-propyl group or an isopropyl group, and is more preferably a methyl group.

A "substituent" on the "optionally substituted C1-C6 alkyl group" represented by $R^2$ is preferably a substituem as defined above, and is more preferably a halogen atom.

The "optionally substituted C1-C6 alkyl group" represented by $R^2$ is preferably a C1-C6 alkyl group, and is more preferably a methyl group, an ethyl group, a n-propyl group or an isopropyl group, most preferably a methyl group.

$R^2$ is preferably a hydrogen atom or a C1-C6 alkyl group, and is more preferably a hydrogen atom or a methyl group, most preferably a hydrogen atom.

In the compound of the present invention represented by general formula (I), $R^3$ is a hydrogen atom, $C(=O)R^5$, $C(=S)R^6$, $S(=O)_2R^7$, an optionally substituted C1-C6 alkyl group, or an optionally substituted C3-C7 cycloalkyl group.

A "C1-C6 alkyl group" in the "optionally substituted C1-C6 alkyl group" represented by $R^3$ is preferably a methyl group, an ethyl group, a n-propyl group or an isopropyl group, and is more preferably a methyl group.

A "substituent" on the "optionally substituted C1-C6 alkyl group" represented by $R^3$ is preferably a substituent as defined above. More preferred is a halogen atom, a cyano group or a 5- to 7-membered monocyclic unsaturated heterocyclic group having 1 to 3 heteroatoms selected from a nitrogen atom, an oxygen atom and a sulfur atom, more preferred is a cyano group or a 5- to 7-membered monocyclic unsaturated heterocyclic group having 1 to 3 heteroatoms selected from a nitrogen atom, an oxygen atom and a sulfur atom, and more preferred is a cyano group or a pyridinyl group.

The "optionally substituted C1-C6 alkyl group" represented by $R^3$ is preferably a C1-C6 alkyl group which may have, as a substituent, a cyano group or a 5- to 7-membered monocyclic unsaturated heterocyclic group having 1 to 3 heteroatoms selected from a nitrogen atom, an oxygen atom and a sulfur atom. More preferred is a methyl group, a cyanomethyl group or a pyridinylmethyl group.

The "optionally substituted C3-C7 cycloalkyl group" represented by $R^3$ is preferably a C3-C7 cycloalkyl group, and is more preferably a cyclopropyl group or a cyclobutyl group.

$R^3$ is preferably $C(=O)R^5$, $C(=S)R^6$ or an optionally substituted C1-C6 alkyl group. More preferred is $C(=O)R^5$; $C(=S)R^6$; or a C1-C6 alkyl group whiCh may have, as a substituent, a cyano group or a 5- to 7-membered monocycle unsaturated heterocyclic group having 1 to 3 heteroatorns selected from a nitrogen atom, an oxygen atom and a sulfur atom, more preferred is $C(=O)R^5$ or $C(=S)R^6$, and most preferred is $C(=O)R^5$.

In the compound of the present invention represented by general formula (I), $R^4$ is a hydrogen atom, an optionally substituted C1-C6 alkyl group, an optionally substituted C3-C7 cycloalkyl group, or an optionally substituted carbonylamino group.

The "optionally substituted C1-C6 alkyl group" represented by $R^4$ is preferably a C1-C6 alkyl group, and is more preferably a methyl group.

The "optionally substituted C3-C7 cycloalky group" represented by $R^4$ is preferably a C3-C7 cycloalkyl group, and is more preferably a cyclopropyl group or a cyclobutyl group.

The "optionally substituted carbonylamino group" represented by $R^4$ is preferably a carbonylamino group which may have a C1-C6 alkyl group, and is more preferably a methylcarbonylamino group or a dimethylcarbonylamino group.

$R^4$ is preferably a hydrogen atom or a C1-C6 alkyl group, and is more preferably a hydrogen atom.

In the compound of the present invention represented by general formula (I), $R^5$ is an optionally substituted C1-C6 alkyl group, an optionally substituted C3-C7 cycloalkyl group, an optionally substituted C1-C6 alkoxy group, an optionally substituted amino group, an optionally substituted 4- to 10 membered monocycle or polycyclic saturated heterocyclic group, an optionally substituted 5- to 10-membered monocyclic or polycyclic unsaturated heterocyclic group, or an optionally substituted 6- to 10-membered monocyclic or polycyclic aromatic hydrocarbon group.

A "C1-C6 alkyl group" in the "optionally substituted C1-C6 alkyl group" represented by $R^5$ is preferably a methyl group.

A "substituent" on the "optionally substituted C1-C6 alkyl group" represented by $R^5$ is preferably a substituent as defined above. More preferred is a halogen atom, a C1-C6 alkoxy group or a C1-C6 mono- or di-alkylamino group; more preferred is a fluorine atom, a methoxy group, an ethoxy group, a monoethylamino group or a dimethylamino group, and most preferred is a fluorine atom.

The "optionally substituted C1-C6 alkyl group" represented by $R^5$ is preferably a C1-C6 alkyl group which may have, as a substituent, a halogen atom, a C1-C6 alkoxy group or a C1-C6 mono- or di-alkylamino group. More preferred is a C1-C6 group which may have, as a substituent, a fluorine atom, a methoxy group, an ethoxy group, a monomethylamino group or a dimethylamino group, more preferred is a C1-C6 alkyl group which may have a fluorine atom, and most preferred is a difluoromethyl group.

The "optionally substituted C3-C7 eyeloalkyl group" represented by $R^5$ is preferably a C3-C7 cycloalkyl group, and is more preferably a cyclopropyl group or a cyclobutyl group.

The "optionally substituted C1-C6 alkoxy group" represented by $R^5$ is preferably a C1-C6 alkoxy group, and is more preferably a methoxy group, an ethoxy group or a pyrazin-2-ylmethoxy group, more preferably ethoxy group or a pyrazin-2-ylmethoxy group.

The "optionally substituted amino group" represented by $R^5$ is preferably a C1-C6 mono- or di-alkylamino group, and is more preferably a C1-C6 monoalkylamino group, more preferably an ethylamino group.

The "optionally substituted 4- to 10-membered monocyclic or polycyclic saturated heterocyclic group" represented by $R^5$ is preferably a 4- to 10-membered monocyclic or polycyclic fully saturated heterocyclic group having 1 to 4 heteroatoms selected from a nitrogen atom, an oxynen atom and a sulfur atom. More preferred is an azetidinyl group, a pyrrolidinyl group or a morpholino group.

A "5- to 10-membered monocyclic or polycyclic unsaturated heterocyclic group" in the "optionally substituted 5- to 10-membered monocyclic or polycyclic unsaturated heterocyclic group" represented by $R^5$ is preferably a 5- to 10-membered monocyclic or polycyclic fully unsaturated or partially saturated heterocyclic group having 1 to 4 heteroatoms selected from a nitrogen atom, an oxygen atom and a sulfur atom. Preferred is a pyridazinyl group, a pyrimidinyl group, an oxazolyl group, an oxadiazolyl group, a pyrazinyl group, a pyridinyl group, an imidazolyl group, a furanyl group, an isoxazolyl group, a triazolopyridinyl group, a triazolyl group, a triazinyl group, a thiazolyl group, a thiadiazolyl group, an imidazopyrarinyl group or a pyrazolyl group, more preferred is an isoxazolyl group, a pyrazolyl group, an oxazolyl group, an oxadiazolyl group, a pyrazinyl group or a pyridazinyl group, and more preferred is a pyrazolyl group, an oxazolyl group, an oxadiazolyl group, a pyrazinyl group or a pyridazinyl group.

In one embodiment of the present invention, a "5- to 10-membered monocyclic or polycyclic unsaturated heterocyclic group" in the "optionally substituted 5- to 10-membered monocyclic or polycyclic unsaturated heterocyclic group" represented by $R^5$ may be an imidazopyridyl group or an imidazopyrazyl group.

A "substituent" on the "optionally sUbstituted 5- to 10-mentbered monocyclic or poly-cyclic unsaturated heterocyclic group" represented by $R^5$ is preferably a substituent as defined above. More preferred is a halogen atom, a cyano group, an oxo group, a C1-C6 alkyl group, a C1-C6 haloalkyl group, a C1-C6 alkoxy-C1-C6 alkyl group, a C1-C6 alkoxy group, a C1-C6 haloalkoxy group, a C1-C6 mono- or di -alkylamino group, a C1-C6 alkylsulfonyl group, a C3-C7 cycloalkyl group or a C6-C10 aromatic hydrocarbon group, more preferred is a fluorine atom, a chlorine atom, a cyano group, an oxo group, a C1-C6 alkyl group, a monofluoromethyl group, a methoxyethyl group, a methoxy group, a monofluoromethoxy group, a dimethylamino group, a methylsulfonyl group, a cyclopropyl group or a phenyl group, more preferred is a C1-C6 alkyl group, and most preferred is a methyl group.

In one embodiment of the present invention, a "substituent" on the "optionally substituted 5- to 10-membered monocyclic polycyclic unsaturated heterocyclic group" represented by $R^5$ may be a hydroxyalkyl group, a mono- or di-alkylaminoalkyl group, a phosphine oxide group or a morpholinomethyl group, and may preferably be a hydroxymethyl group, a methylaminomethyl group, a dimethylaminomethyl group or a morpholinomethyl group.

The "optionally substituted 5- to 10-membered monocyclic or polycyclic unsaturated heterocyclic group" represented by $R^5$ is a 5- to 10-membered monocyclic or polycyclic fully unsaturated or partially saturated heterocyclic group having 1 to 4 heteroatoms selected from a nitrogen atom, an oxygen atom and a sulfur atom, which may have, as to substituent, a group selected from the group consisting of a halogen atom, a cyano group, an oxo group, a C1-C6 alkyl group, a C1-C6 haloalkyl group, a C1-C6 alkoxy-C1-C6 alkyl group, a C1-C6 alkoxy group, a C1-C6 haloalkoxy group, a C1-C6 mono- or di-alkylamino group, C1-C6 alkylsulfonyl group, a C3-C7 cycloalkyl group and a C6-C10 aromatic hydrocarbon group. More preferred is a pyridazinyl group, a pyrimidinyl group, an oxazolyl group, an oxadiazolyl group, a pyrazinyl group, a pyridinyl group, an imidazolyl group, a furanyl group, an isoxazolyl group, a triazolopyridinyl group, a triazolyl group, a triazinyl group, a thiazolyl group, a thiadiazolyl group, an imidazopyrazinyl group or a pyrazolyl group, which may have, as a substituent, a group selected from the group consisting of a halogen atom, a cyano group, an oxo group, a C1-C6 alkyl group, a C1-C6 haloalkyl group, a C1-C6 alkoxy -C1-C6 alkyl group, a C1-C6 alkoxy group, a C1-C6 haloalkoxy group, a C1-C6 mono -or di-alkylamino group, a C1-C6 alkylsullbnyl group, a C3-C7 cycloalkyl group and a C6-C10 aromatic hydrocarbon group, more preferred is a pyridazinyl group, a pyrimidinyl group, an oxazolyl group, ar oxadiazolyl group, a pyrazinyl group, a pridinyl group, an imidazolyl group, a furanyl group, an isoxazolyl group, a triazolopyridinyl group, a triazolyl aroup, as triazinyl group, a thiazolyl group, a thiadiazolyl group, an imidazopyrazinyl group or a pyrazolyl group, which may have a C1-C6 alkyl group, still more preferred is an isoxazolyl group, a pyrazolyl group, an oxazolyl group, an oxadiazolyl group, a pyrazinyl group or a pyridazinyl group, which may have a C1-C6 alkyl group, and more preferred is a pyrazolyl group, an oxazolyl group, an oxadiazolyl group, a pyrazinyl group or a pyridazinyl group, which may have a C1-C6 alkyl group.

In one embodiment of the present invention, the "optionally substituted 5- to 10-membered monocyclic or polycyclic unsaturated heterocyclic group" represented by $R^5$ is a 5- to 10-membered monocyclic or polycyclic fully unsaturated or partially saturated heterocyclic group having 1 to 4 heteroatoms selected from a nitrogen atom, an oxygen atom and a sulfur atom, which may have, as a substituent, a group selected from the group consisting of a halogen atom, a cyano group, an oxo group, a C1-C6 alkyl group, a C1-C6 haloalkyl group, a C1-C6 alkoxy-C1-C6 alkyl group, a C1-C6 alkoxy group, a C1-C6 haloalkoxy group, a C1-C6 mono- or di-alkylamino group, a C1-C6 alkylsulfonyl group, a C3-C7 cycloalkyl group, a hydroxyalkyl group, a mono- or di-alkylaminoalkyl group, a phosphine oxide group, a morpholinomethyl group and a C6-C10 aromatic hydrocarbon group. More preferred is a pyridazinyl group, a pyrimidinyl group, an oxazolyl group, an oxadiazolyl group, a pyrazinyl group, a pyridinyl group, an imidazolyl group, a furanyl group, an isoxazolyl group, a triazolopyridinyl group, a triazotyl group, a triazinyl group, a thiazolyl group, a thiadiazolyl group, an imidazopyrazinyl group, an imidazopyridyl group, an imidazopyrazyl group or a pyrazolyl group, which may have, as a substituent, a group selected from the group consisting of a halogen atom, a cyano group, an oxo group, a C1-C6 alkyl group, a C1-C6 haloalkyl group, a C1-C6 alkoxy-C1-C6 alkyl group, a C1-C6 alkoxy group, a C1-C6 haloalkoxy group, a C1-C6 mono- di-alkylamino group, a C1-C6 alkylsulfonyl group, a C3-C7 cycloalkyl group, a hydroxyalkyl group, a mono -or di-alkylaminoalkyl group, a phosphine oxide group, a morpholinomethyl group and a C6-C10 aromatic hydrocarbon group, more preferred is a pyridazinyl group, a pyrimidinyl group, an oxazolyl group, an oxadiazolyl group, a pyrazinyl group, a pyridinyl group, an imidazolyl group, a furanyl group, an isoxazolyl group, a triazolopyridinyl group, a triazolyl group, a triazinyl group, a thiazolyl group, a thiadiazolyl group, an imidazopyrazinyl group, an imidazopyridyl group, an imidazopyrazyl group or a pyrazolyl group, which may have a C1-C6 alkyl group, still more preferred is an isoxazolyl group, a pyrazolyl group, an oxazolyl group, an oxadiazolyl group, a pyrazinyl group or a pyridazinyl group, which may have a C1-C6 alkyl group, and more preferred may be a pyrazolyl group, an oxazolyl group, an oxadiazolyl group, a pyrazinyl group or a pyridazinyl group, which may have a C1-C6 alkyl group.

In one embodiment of the present invention, the "optionally substituted 5- to 10-membered monocyclic or polycyclic unsaturated heterocyclic group" represented by $R^5$ includes the following structures, by way of example.

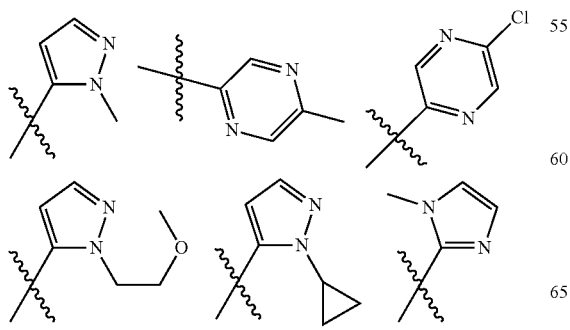

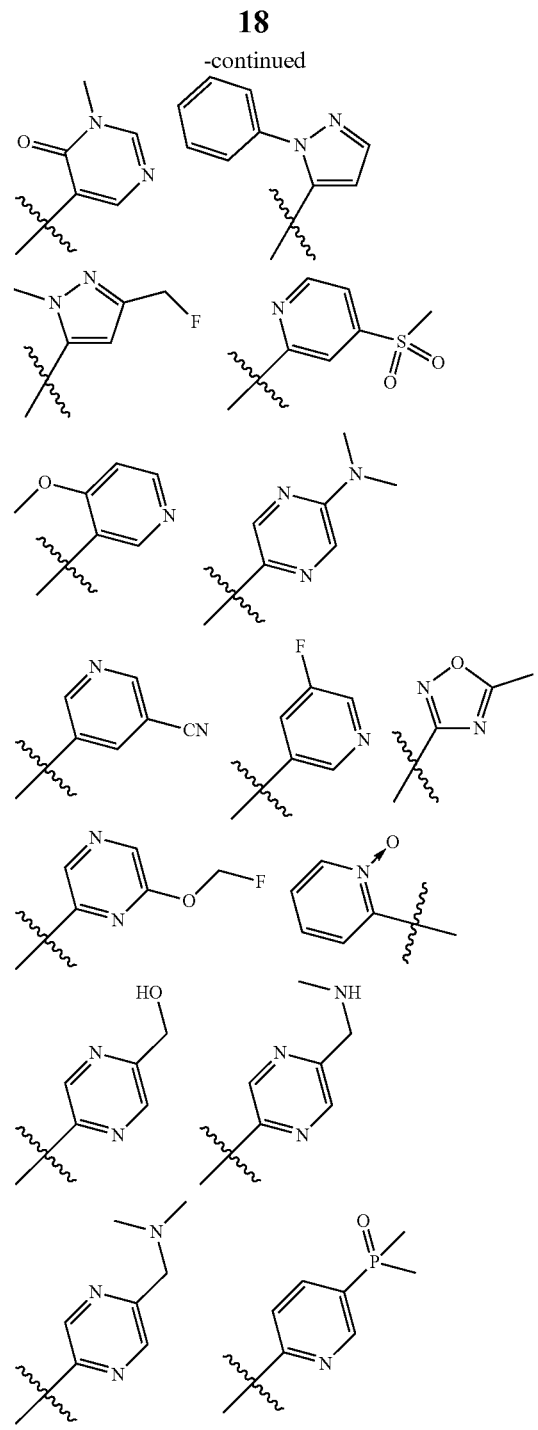

The "optionally substituted 6- to 10-membered monocyclic or polycyclic aromatic hydrocarbon group" represented by $R^5$ is preferably a 6- to 10-membered monocyclic or polycyclic aromatic hydrocarbon group, and is more preferably a phenyl group.

$R^5$ is preferably an optionally substituted C1-C6 alkyl group, an optionally substituted C1-C6 alkoxy group, an optionally substituted amino group, an optionally substituted 5- to 10-membered monocyclic polycyclic unsaturated heterocyclic group or an optionally substituted 6- to 10-membered monocyclic or polycyclic aromatic hydrocarbon group. More preferred is an optionally substituted C1-C6 alkyl group, a C1-C6 alkoxy group, a C1-C6 mono- or di-alkylamino group, an optionally substituted 5- to 10-membered monocyclic or polycyclic unsaturated heterocyclic group or a 6- to 10-membered monocyclic or polycyclic aromatic hydrocarbon group, more preferred is as C1-C6 alkyl group which may have, as a substituent, a halogen atom, a C1-C6 alkoxy group or a C1-C6 mono- or di-alkylamino a C1-C6 alkoxy group; a C1-C6 mono- or di-alkylamino group; a 5- to 10-membered monocyclic or polycyclic fully unsaturated or parially saturated heterocyclic group having 1 to 4 heteroatoms selected from a nitrogen atom, an oxygen atom and a sulfur atom, which may have, as a substituent, a group selected from the group consisting of a halogen atom, a cyano group, an oxo group, a C1-C6 alkyl group, a C1-C6 haloalkyl group, a C1-C6 alkoxy -C1-C6 alkyl group, a C1 -C6 alkoxy group, a C1-C6 haloalkoxy group, a C1-C6 mono- or di-alkylamino group, a C1-C6 alkylsulfonyl group, a C3-C7 cycloalkyl group and a C6-C10 aromatic hydrocarbon group; or a 6- to 10-membered aromatic hydrocarbon group, and more preferred is as C1-C6 alkyl group which may have a halogen atom; or a 5- to 10-membered monocyclic or polycyclic fully unsaturated or partially saturated heterocyclic group having 1 to 4 heteroatoms selected from a nitrogen atom, an oxygen atom and a sulfur atom, which may have a C1-C6 alkyl group.

In one embodiment of the present invention, $R^5$ is an optionally substituted C1-C6 alkyl group, an optionally substituted C1-C6 alkoxy group, an optionally substituted amino group, an optionally substituted 5- to 10-membered monocyclic or polycyclic unsaturated heterocyclic group or an optionally substituted 6- to 10-membered monocyclic or polycyclic aromatic hydrocarbon group. More preferred is an optionally substituted C1-C6 alkyl group, a C1-C6 alkoxy group, a C1-C6 mono- or di -alkylamino group, an optionally substituted 5- to 10-membered monocyclic or polycyclic unsaturated heterocyclic group or a 6- to 10-membered monocyclic or polycyclic aromatic hydrocarbon group, more preferred is a C1-C6 alkyl group which may have, as a substituent, a halogen atom, a C1-C6 alkoxy group or a C1-C6 mono- or di-alkylamino group; a C1-C6 alkoxy group; a C1-C6 mono- or di-alkylamino group; a 5- to 10-membered monocyclic or polycyclic fully unsaturated or partially saturated heterocyclic group or heterocyclic alkyl group having 1 to 4 heteroatoms selected from a nitrogen atom, an oxygen atom and a sulfur atom, which may have, as a substituent, a group selected from the group consisting of a halogen atom, a cyano group, an oxo group, a C1-C6 alkyl group, a C1-C6 haloalkyl group, a C1-C6 alkoxy-C1-C6 alkyl group, C1-C6 hydroxyalkyl group, a C1-C6 alkoxy group, a C1-C6 haloalkoxy group, a C1-C6 mono- or di-alkylamino group, a C1-C6 mono- or di-alkylamino C1-C6 alkyl group, a C1-C6 alkylsulfonyl group, a C3-C7 cycloalkyl group, a phosphine oxide group and a C6-C10 aromatic hydrocarbon group; or a 6- to 10-membered aromatic hydrocarbon group, and more preferred may be a C1-C6 alkyl group which may have a halogen atom; or a 5- to 10-membered mortocyclic or polycyclic fully unsaturated or partially saturated heterocyclic group having 1 to 4 heteroatoms selected from a nitrogen atom, an oxygen atom and a sulfur atom, which may have a C1-C6 alkyl group.

In the compound of the present invention represented by general formula (I), $R^6$ is a hydrogen atom, an optionally substituted C1-C6 alkyl group, an optionally substituted C1-C6 mono- or di-alkylamino group, an optionally substituted C3-C7 cycloalkyl group, or an optionally substituted 4- to 10-membered monocyclic or polycyclic saturated heterocyclic group having 1 to 4 heteroatoms selected from a nitrogen atom, an oxygen atom and a sulfur atom.

The "optionally substituted C1-C6 alkyl group" represented by $R^6$ is preferably a C1-C6 alkyl group, and is more preferably an ethyl group.

The "optionally substituted C1-C6 mono- or di-alkylamino group" represented by $R^6$ is preferably a C1-C6 mono- or di-alkylamino group, and is more prerably C1-C6 monoalkylamino group, and more preferably an ethylamino group.

The "optionally substituted C3-C7 cycloalkyl group" represented by $R^6$ is preferably a C3-C7 cycloalkyl group and is amore preferably a C3-C5 cycloalkyl group, and more preferably a cyclopropyl group or a cyclobutyl group.

A "4- to 10-membered monocyclic or polycyclic saturated heterocyclic group having 1 to 4 heteroatoms selected from a nitrogen atom, an oxygen atom and a sulfur atom" in the "optionally substituted 4- to 10-membered monocyclic or polycyclic saturated heterocyclic group having 1 to 4 heteroatoms selected from a nitrogen atom, an oxygen atom and a sulfur atom" represented by $R^6$ is preferably an azetidinyl group, a pyrrolidinyl group, a piperidinyl group, a piperazinyl group, a hexamethyleneimino group, a morpholino group, a thiomorpholino group, a homopiperazinyl group, an oxetanyl group, of tetrahydrofuranyl group, a tetrahydropyranyl group or 2,6-diazaspiro[3.3]heptane. More preferred is 2,6-diazacyclo[3.3]heptane.

A "substituent" on the "optionally substituted 4- to 10-membered monocyclic or polycyclic saturated heterocyclic group having 1 to 4 heteroatoms selected from a nitrogen atom, an oxygen atom and a sulfur atom" represented by $R^6$ is preferably a substituent as defined above. More preferred is a C1-C6 alkyl group, and more preferred is a methyl group.

The "optionally substituted 4- to 10-membered monocyclic or polycyclic saturated heterocyclic group having 1 to 4 heteroatoms selected from a nitrogen atom, an oxygen atom and a sulfur atom" represented by $R^6$ is preferably a 4- to 10-membered monocyclic or polycyclic saturated heterocyclic group having 1 to 4 heteroatoms selected from a nitrogen atom, an oxygen atom and a sulfur atom, which may have a C1-C6 alkyl group. More preferred is 2-methyl-2,6-diazacyclo[3.3]heptane.

$R^6$ is preferably an optionally substituted C1-C6 mono- or di-alkylamino group or an optionally substituted 4- to 10-membered monocyclic or polycyclic saturated heterocyclic group haying 1 to 4 heteroatoms selected from a nitrogen atom, an oxygen atom and a sulfur atom. More preferred is a C1-C6 mono- or di-alkylamino group or a 4- to 10-membered monocyclic or polycyclic saturated heterocyclic group having 1 to 4 heteroatoms selected from a nitrogen atom, an oxygen atom and a sulfur atom, which may have a C1-C6 alkyl group, and more preferred is an ethyl amino group or 2-methyl -2,6-diazacyclo[3.3]heptane.

In the compound of the present invention represented by general formula (I), $R^7$ is an optionally substituted C1-C6 alkyl group, an optionally substituted C3-C7 cycloalkyl group, an optionally substituted 5- to 0-membered monocyclic or polycyclic saturated or unsaturated heterocyclic group, or an optionally substituted 6- to 10-membered monocyclic or polycyclic aromatic hydrocarbon group.

The "optionally substituted C1-C6 alkyl group" represented by $R^7$ is preferably C1-C6 alkyl group, and is more preferably a methyl group or an ethyl group.

The "optionally substituted C3-C7 cycloalkyl group" represented by $R^7$ is preferably a C3-C7 cycloalkyl group, and is more preferably a cyclopropyl group or a cyclobutyl group.

The "optionally substituted C1-C6 haloalkyl group" represented by $R^7$ is preferably a C1-C6 haloalkyl group, and is more preferably a trifluoroethyl group.

The "optionally substituted 5- to 10-membered monocyclic or polycyclic saturated or unsaturated heterocyclic group" represented by $R^7$ is preferably a 5- to 10-membered monocyclic polycyclic saturated or unsaturated heterocyclic group having 1 to 4 heteroatoms selected from a nitrogen atom, an oxygen atom and a sulfur atom. More preferred is a pyridinyl group or a pyrimidinyl group.

The "optionally substituted 6- to 10-membered monocyclic or polycyclic aromatic hydrocarbon group" represented by $R^7$ is preferably a 6- to 10-membered monocyclic or polycyclic aromatic hydrocarbon group, and is more preferably a phenyl group.

In the compound of the present invention represented by general formula (I), n is an integer of 0 to 3, preferably 0 of 1, and more preferably 0.

One preferred embodiment of the present invention is a compound of general formula (I), wherein
$R^1$ is a hydrogen atom or a C1-C3 all group;
X is $NR^2R^3$, $OR^4$ or a 5- to 7-membered monocyclic saturated or unsaturated heterocyclic group having 1 to 3 heteroatoms selected from a nitrogen atom, an oxygen atom and a sulfur atom;
$R^2$ is a hydrogen atom or a C1-C6 alkyl group;
$R^3$ is a hydrogen atom, $C(=O)R^5$, $C(=S)R^6$ or a C1-C6 alkyl group (which may have, as a substituent, ar cyano group or a 5- to 7-membered monocyclic unsaturated heterocyclic group having 1 to 3 heteroatoms selected from a nitrogen atom, an oxygen atom and a sulfur atom);
$R^4$ is a hydrogen atom;
$R^5$ is an optionally substituted C1-C6 alkyl group, a C1-C6 alkoxy group, C1-C6 mono- or di-alkylamino group, an optionally substituted 5- to 10-membered monocyclic or polycyclic unsaturated heterocyclic group, or a 6- to 10-membered monocyclic or polycyclic aromatic hydrocarbon group;
$R^6$ is a C1-C6 mono- or di-alkylamino group, or a 4- to 10-membered monocyclic or polycyclic saturated heterocyclic group having 1 to 4 heteroatoms selected from a nitrogen atom, an oxygen atom and a sulfur atom, which may have a C1-C6 alkyl group;
the ring A is bicyclo[2.2.1]heptane or bicyclo[2.2.2]octane; and
n 0 or 1;
or a pharmaceutically acceptable salt thereof.

A more preferred embodiment of the present invention is a compound of general formula (I), wherein
$R^1$ is a hydrogen atom;
X is $NR^2R^3$ or a 5- to 7-membered monocyclic saturated or unsaturated heterocyclic group having 1 to 3 heteroatoms selected from a nitrogen atom, an oxygen atom and a sulfur atom;
$R^2$ is a hydrogen atom;
$R^3$ $C(=O)R^5$;

$R^5$ is an optionally substituted C1-C6 alkyl group, a C1-C6 alkoxy group, a C1-C6 mono- or di-alkylamino group, an optionally substituted 5- to 10-membered monocyclic or polycyclic unsaturaled heterocyclic group, or a 6- to 10-membered monocyclic or polycyclic aromatic hydrocarbon group;
the ring A is bicyclo[2.2.1]heptane or bicyclo[2.2.2]octane; and
n is 0 or 1;
or a pharmaceutically acceptable salt thereof.

A more preferred embodiment of the present invention is a compound of general formula (I), wherein
$R^1$ is a hydrogen atom;
X is $NR^2R^3$ or a 5- to 7-membered monocyclic saturated heterocyclic group having 1 to 3 heteroatoms selected from a nitrogen atom, an oxygen atom and a sulfur atom;
$R^2$ is a hydrogen atom;
$R^3$ is $C(=O)R^5$;
$R^5$ is a C1-C6 alkyl group which may have a halogen atom, or a 5- to 10-membered monocyclic or polycyclic fully unsaturated or partially saturated heterocyclic group which may have a C1-C6 alkyl group;
the ring A is bicyclo[2.2.1]heptane; and
n is 0;
or a pharmaceutically acceptable salt thereof.

Specific examples of the compound of the present invention may include the compounds prepared in the Example section described later, but are not limited thereto.

One embodiment of the present invention is a compound selected from (1) to (8) shown below, or a pharmaceutically acceptable salt thereof. These compounds particularly have high pharmacological activity, show long-lasting high blood levels, and have good oral absorption.

(1) 6-ethynyl-7-(4-morpholinobicyclo[2.2.1]heptan-1-yl)-5-(quinolin-3-yl)-7H -pyrrolo[2,3-d]pyrimidine-4-amine (2) N-(4-(4-amino-6-ethynyl-5-(quinolin-3-yl)-7H-pyrrolo[2,3-d]pyrimidin-7-yl)bicyclo[2.2.1]heptan-1-yl)-1-methyl-1H-pyrazole-5-carboxamide (3) N-(4-(4-amino-6-ethynyl-5-(quinolin-3-yl)-7H-pyrrolo[2,3-d]pyrimidin-7-yl)bicyclo[2.2.1]heptan-1-yl)-2,2-difluoroacetamide (4) N-(4-(4-amino-6-ethynyl-5-(quinolin-3-yl)-7H-pyrrolo[2,3-d]pyrimidin-7-yl)bicyclo[2.2.1]heptan-1-yl)-5-methyl-1,2,4-oxadiazole-3-carboxamide (5) N-(4-(4-amino-6-ethynyl-5-(quinolin-3-yl)-7H-pyrrolo[2,3-d]pyrimidin-7-yl)bicyclo[2.2.1]heptan-1-yl)-5-methylpyrazine-2-carboxamide (6) N-(4-(4-amino-6-ethynyl-5-(quinolin-3-yl)-7H-pyrrolo[2,3-d]pyrimidin-7-yl)bicyclo[2.2.1]heptan-1-yl) oxazole-2-carboxamide (7) N-(4-(4-amino-6-ethynyl-5-(quinolin-3-yl)-7H-pyrrolo[2,3-d]pyrimidin-7-yl)bicyclo[2.2.1]heptan-1-yl) pyrazine-2-carboxamide (8) N-(4-(4-amino-6-ethynyl-5-(quinolin-3-yl)-7H-pyrrolo[2,3-d]pyrimidin-7-yl)bicyclo[2.2.1]heptan-1-yl) pyridazine-3-carboxamide (9) N-(4-(4-amino-6-ethynyl-5-(quinolin-3-yl)-7H-pyrrolo[2,3-d]pyrimidin-7-yl)bicyclo[2.2.1]heptan-1-yl) pyrimidine-5-carboxamide

(10) N-(4-(4-amino-6-ethynyl-5-(quinolin-3-yl)-7H-pyrrolo[2,3-d]pyrimidin-7-yl)bicyclo[2.2.1]heptan-1-yl)-1-cyclopropyl-1H-pyrazole-5-carboxamide

(11) N-(4-(4-amino-6-ethynyl-5-(quinolin-3-yl)-7H-pyrrolo[2,3-d]pyrimidin-7-yl)bicyclo[2.2.1]heptan-1-yl) isoxazole-5-carboxamide <Preparation Processes for the Compound Represented by Formula (I)>

Preparation processes for the compound of the present invention will then be described below.

The compound of the present invention represented by formula (I) may be prepared, for example, by the preparation processes shown below or the processes shown in the Example section, etc. However, preparation processes for the compound of the present invention represented by formula (I) are not limited to these reaction examples. The product obtained in each step may be isolated and purified by any known separation or purification means (e.g., concentration, vacuum concentration, crystallization, solvent extraction, reprecipitation, chromatography) or may be provided for the next step without being isolated and purified. Moreover, in the preparation processes shown below, introduction of a protective group or deprotection may be conducted as needed, regardless of the presence or absence of the description thereof, and the order of steps may be changed as appropriate.

[Preparation Process 1]

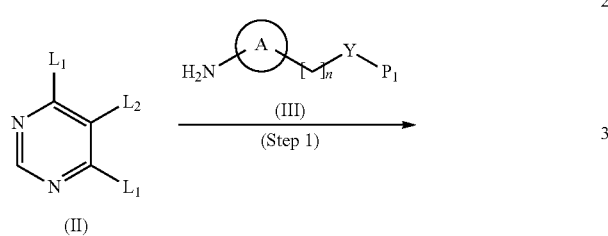

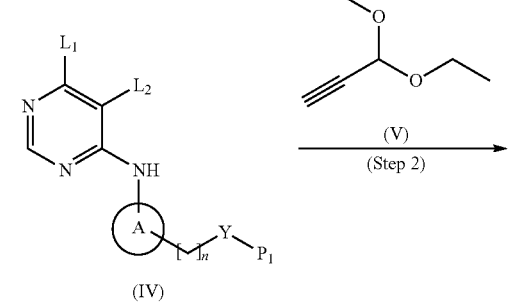

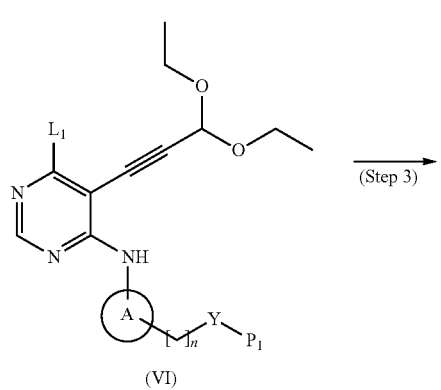

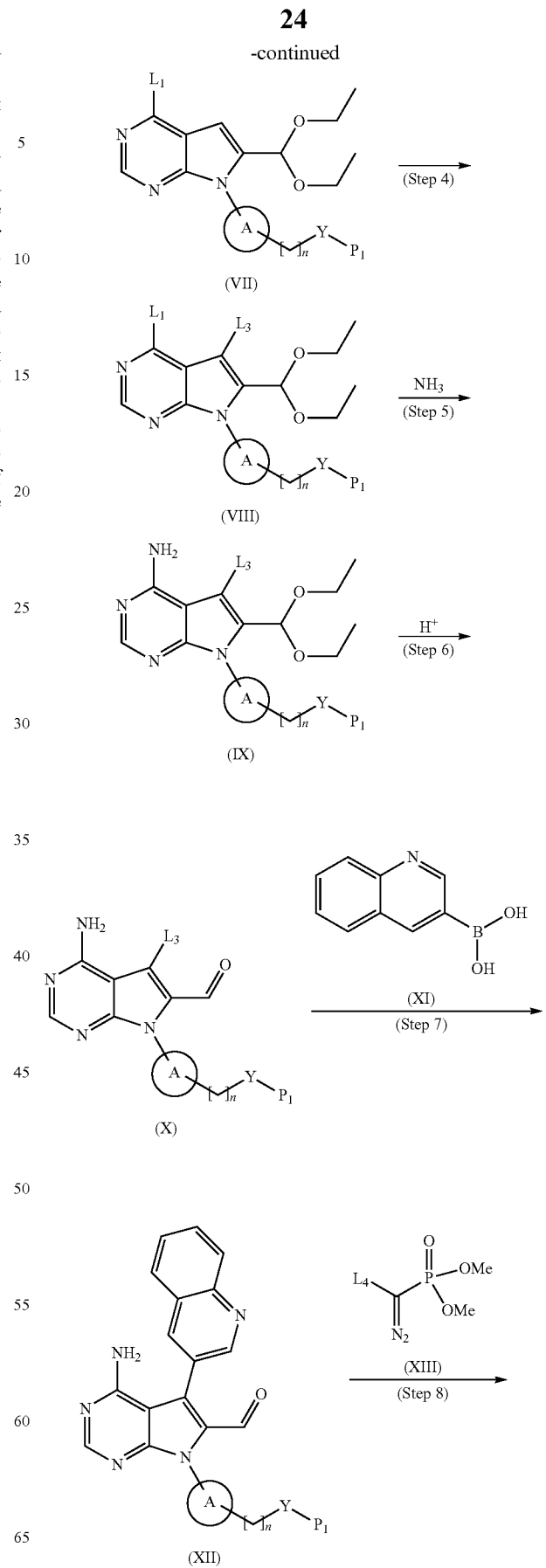

-continued

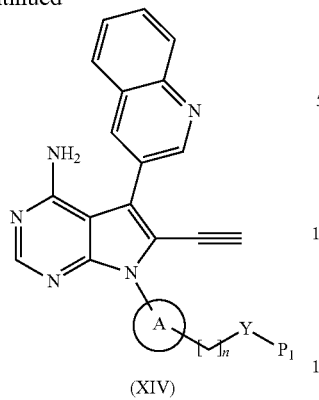

(XIV)

wherein Y represents NH or O, $P_1$ represents a hydrogen atom or a protective group for an amino group, $L_1$, $L_2$, $L_3$ and $L_4$ each represent a leaving group, and the ring A and n are as defined above.

(Step 1)

This step is configured to react a compound represented by general formula (II) with a compound represented by general formula in the presence of a base to thereby prepare a compound represented by general formula (IV).

In general formula (II), the leaving group represented by $L_1$ is a fluorine atom or a chlorine atom. Likewise, the leaving aroup represented by $L_2$ is an iodine atom or a bromine atom. The compounds represented by general formulae (II) and (III) may be commercially available products or may be prepared according to known procedures.

The compound represented by general formula (III) may be used in an amount of 1 to 10 moles, preferably 1 to 3 moles, relative to 1 mole of the compound represented by general formula (II).

Examples of a base available for use in this step include an organic base (e.g., triethylamine, diisopropylethylamine, pyridine) or an inorganic base (e.g., sodium bicarbonate, sodium carbonate, potassium carbonate, cesium carbonate, sodium hydroxide, potassium phosphate, potassium tert-butyrate).

The amount of such a base to be used is usually 1 mole to excess moles, preferably 1 to 3 moles, relative to 1 mole of the compound represented by general formula (II).

The reaction solvent is not limited in any way as long as it is inert to the reaction, and preferred examples include tetrahydrofuran, 1,4-dioxane, 1,2-dimethoxyethane, dimethyl sulfoxide, dimethylformamide, N-methylpyrrolidone, etc., or mixed solvents thereof.

The reaction temperature is usually 0° C. to 200° C., and preferably 50° C. to 120° C.

The reaction time is usually 5 minutes to 7 days, and preferably 30 minutes to 24 hours.

(Step 2)

This step is configured to cause Sonogashira reaction between the compound represented by formula (IV) and a compound represented by formula (V) to thereby prepare a compound represented by formula (VI).

The Sonogashira reaction may be carried out according to generally known procedures (e.g., as described in Chemical Reviews, Vol. 107, p. 874 (2007)) or similar procedures, for example, may be carried out in the presence of a transition metal catalyst and a base in a solvent not adversely affecting the reaction.

Examples of a transition metal catalyst available for use include palladium catalysts (e.g., palladium acetate, palladium chloride, tetrakis(triphenylphosphine)-palladium, dichlorobis(triphenylphosphine)palladium, dichloro[1,1'-bis (diphenyl -phosphino)ferrocene]palladium, tris(dibenzylideneacetone)dipalladium(0)), copper catalysts (e.g., copper bromide, copper iodide) and so on, which may be used either alone or in combination.

The amount of such a transition metal catalyst available for use is suitably within the range of 0.001 to 1 mole, relative to 1 mole of the compound represented by formula (IV).

If necessary, a ligand for palladium may be used, as exemplified by triphenylphosphine, tri(2-furyl)phosphine, 1,1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, 2-di-tert-butylphosphino-3, 4,5,6-tetramethyl-2',4',6'-tri-i-propylbiphenyl, etc.

The reaction solvent available for use is not limited in any way as long as it is, inert to the reaction, and examples include tetrahydrofuran, 1,4-dioxane, 1,2-dimethoxyethane, N,N-dimethylformamide, N,N-dimethylacetamide, N-methyl-2-pyrrolidone, benzene, toluene, acetonitrile, dimethyl sulfoxide, water, or mixed solvents thereof.

Examples of a base available for use in this step include an organic base (e.g., triethylatnine, diisopropylethylamine, pyridine, 4-dimethylaminopyridine) or an inorganic base (e.g., sodium bicarbonate, sodium carbonate, potassium carbonate, cesium carbonate, sodium hydroxide, sodium hydride, potassium phosphate, sodium phosphate, potassium tert-butyrate).

The reaction time is usually 5 minutes to 7 days, and preferably 30 minutes to 24 hours.

The reaction temperature is usually 25° C. to 200° C. and preferably 30° C. to 100° C.

(Step 3)

This step is configured to react the compound represented by general formula (VI) in the presence of a base to thereby prepare a compound represented by general formula (VII).

Examples of a base available for use in this step include an organic base (e.g., diisopropylethylamine, pyridine, tetrabutylammonium fluoride) or an inorganic base (e.g., sodium bicarbonate, sodium carbonate, potassium carbonate, cesium carbonate, sodium hydroxide, sodium hydride, potassium phosphate, sodium phosphate, potassium tert-butyrate).

The reaction solvent available for use may be exemplified by tetrahydrofuran, 1,4-dioxano, 1,2-dimethoxyethane, N,N-dimethylformamide, N,N-dimethylacetamide, N-methyl-2-pyrrolidone, benzene, toluene, acetonitrile, dimethyl sulfoxide, water, or mixed solvents thereof.

The reaction time is usually 5 minutes to 7 days, and preferably 30 minutes to 24 hours.

The reaction temperature is usually 25° C. to 200° C., and preferably 50° C. to 100° C.

(Step 4)

This step is configured to halogenate the compound represented by formula (VII) in the presence or absence of a base to thereby prepare a compound represented by formula (VIII).

In general formula (VIII), the leaving group represented by $L_3$ is a chlorine atom, a bromine atom or an iodine atom.

This step may be carried out using N-chlorosuccinimide, N-bromosuccinimide, N-iodosuccinimide, bromine, and iodine, etc.

The solvent is not limited in any way as long as it is inert to the reaction, but the reaction may be carried out in an appropriate solvent inert to the reaction, as exemplified by acetonitrile, ethyl acetate, tetrahydrofuran, methanol, ethanol, N,N -dimethylformamide, N,N-dimethylacetamide, N-methyl-2-pyrrolidone, etc.

Examples of a base available for use include an organic base (e.g., diisopropylethylamine, pyridine, tetrabutylammonium fluoride) or sodium bicarbonate, sodium carbonate, potassium carbonate, cesium carbonate, sodium hydroxide, sodium hydride, potassium phosphate, sodium phosphate, potassium tert-butyrate, etc.

The reaction temperature is usually 0° C. to 100° C., and preferably room temperature to reflux temperature.

The reaction time is usually 10 minutes to 3 days, and preferably 30 minutes to 24 hours.

(Step 5)

This step is configured to react the compound represented by general formula (VIII) with ammonia or a salt thereof to thereby prepare a compound represented by general formula (IX).

The amount of ammonia or a salt thereof to be used in this step is usually equimolar to excess moles, relative to 1 mole of the compound represented by general formdla (VIII).

The reaction solvent is not limited in any way as long as it is inert to the reaction, and preferred examples include water, methanol, ethanol, isopropanol, tetrahydrofuran, 1,4-dioxane, 1,2-dimethoxyethane, dimethylformamide, N-methylpyrrolidone, dimethyl sulfoxide, etc., or mixed solvents thereof.

The reaction temperature is usually 0° C. to 200° C., and preferably 70° C. to 120° C.

The reaction time is usually 5 minutes to 7 days, and preferably 1 hour to 24 hours.

(Step 6)

This step is configured to prepare a compound represented by structural formula (X) from the compound represented by structural formula (IX) under acidic conditions.

Examples of an acid include hydrochloric acid, acetic acid, trifluoroacetic acid, sulfuric acid, methanesulfortic acid, tosylic acid, etc, The amount of such an acid to be used is 1 mole to excess moles, preferably 1 mole to 100 moles, relative to 1 mole of the compound represented by structural formula (IX).

Any solvent may be used in the reaction as long as it does not adversely affect the reaction, as exemplified by water, methanol, ethanol, isopropanol, tetrahydrofuran, 1,4-dioxane, 1,2-dimethoxyethane, dimethylformamide, N-methylpyrrolidone, dimethyl sulfoxide, etc., or mixtures thereof.

The reaction temperature is usually 0° C. to 200° C., and preferably 25° C. to 80° C.

The reaction time is usually 5 minutes to 7 days, and preferably 1 hour to 24 hours.

(Step 7)

This step is configured to cause coupling reaction between the compound represented by general formula (X) and 3-quinolineboronic acid to thereby prepare a compound represented by structural formula (XII).

This step may be carried out according to generally known procedures (e.g., Chemical Reviews, Vol. 95, p. 2457, 1995), for example, may be carried out in the presence of a transition metal catalyst and a base in a solvent not adversely affecting the reaction.

The amount of 3-quinolineboronic acid to be used is 1 to 10 moles, preferably 1 to 3 moles, relative to 1 mole of the compound represented by general formula (X).

Examples of a transition metal catalyst available for use include palladium catalysts (e.g., palladium acetate, palladium chloride, tetrakis(triphenylphosphine) -palladium, 1,1'-bis(diphenylphosphino)ferrocene-palladium(II) dichloride), nickel catalysts (e.g., nickel chloride), etc. If required, a ligand (e.g., triphenylphosphine, tri -tert-butylphosphine) may be added, and a metal oxide (e.g., copper oxide, silver oxide) or the like may be used as a co-catalyst.

The amount of such a transition metal catalyst to be used will vary depending on the type of catalyst, but it is usually 0.0001 to 1 mole, preferably 0.01 to 0.5 moles, relative to 1 mole of the compound represented by general formula (X). The amount or such a ligand to be used is usually 0.0001 to 4 moles, preferably 0.01 to 2 moles, relative to 1 mole of the compound represented by general formula (X), while the amount of such a co-catalyst to be used is usually 0.0001 to 4 moles, preferably 0.01 to 2 moles, relative to 1 mole of the compound represented by general formula (X).

Examples of a base include organic amine compounds (e.g., trimethylamine, triethylamine, diisopropylethylamine), alkali metal salts (e.g., sodium bicarbonate, sodium carbonate, potassium carbonate, cesium carbonate, potassium phosphate, sodium hydroxide), metal hydrides (e.g., potassium hydride, sodium hydride), alkali metal alkoxides (e.g., sodium methoxide, sodium ethoxide, potassium tert-butoxide), etc.

The amount of such a base to be used is usually 0.1 to 10 moles, preferably 1 to 5 moles, relative to 1 mole of the compound represented by general formula (X).

Any solvent may be used as long as it does not adversely affect the reaction, and examples include hydrocarbon-based solvents (e.g., benzene, toluene, xylene), halogenated hydrocarbon-based solvents (e.g., chloroform, 1,2 -dichloroethane), nitrile -based solvents (e.g., acetonitrile), ether-based solvents (e.g., 1,2-dimethoxyethane, tetrahydrofuran, 1,4-dioxane), alcohol-based solvents (e.g., methanol, ethanol), aprotic polar solvents (e.g., dimethylformamide, dimethyl sulfoxide), water, or mixtures thereof.

The reaction temperature is usually 0° C. to 200° C., and preferably 60° C. to 120° C.

The reaction time is usually 5 minutes to 7 days, and preferably 1 hour to 24 hours.

(Step 8)

This step is configured to react the compound represented by formula ((XII) with a compound represented by formula (XIII) to thereby prepare a compound represented by formula (XIV).

In general formula (XIII), the leaving group represented by $L_4$ is a hydrogen atom or an acetyl group.

This step may be carried out according to generally known procedures (e.g., Synthetic Communications, Vol. 19, p. 561, 1989), for example, may be carried out in the presence of a base in a solvent not adversely affecting the reaction.

Examples of a base include alkali metal salts (e.g., sodium bicarbonate, sodium carbonate, potassium carbonate, cesium carbonate, potassium phosphate, sodium hydroxide), metal hydrides (e.g., potassium hydride, sodium hydride), alkali metal alkoxides (e.g., sodium methoxide, sodium ethoxide, potassium tert-butoxide), etc.

Any solvent may be used as long as it does not adversely affect the reaction, and examples include hydrocarbon-based solvents (e.g., benzene, toluene, xylene), nitrile-based solvents (e.g., acetonitrile), ether-based solvents (e.g., 1,2-dimethoxyethane, tetrahydrofuran, 1,4-dioxane), alcohol-based solvents (e.g., methanol, ethanol), aprotic polar solvents (e.g., dimethylformamide, dimethyl sulfoxide), water, or mixtures thereof.

The reaction temperature is usually −100° C. to 100° C., and preferably −78° C. to 50° C.

The reaction time is usually 5 minutes to 7 days, and preferably 1 hour to 24 hours.

[Preparation Process 2]

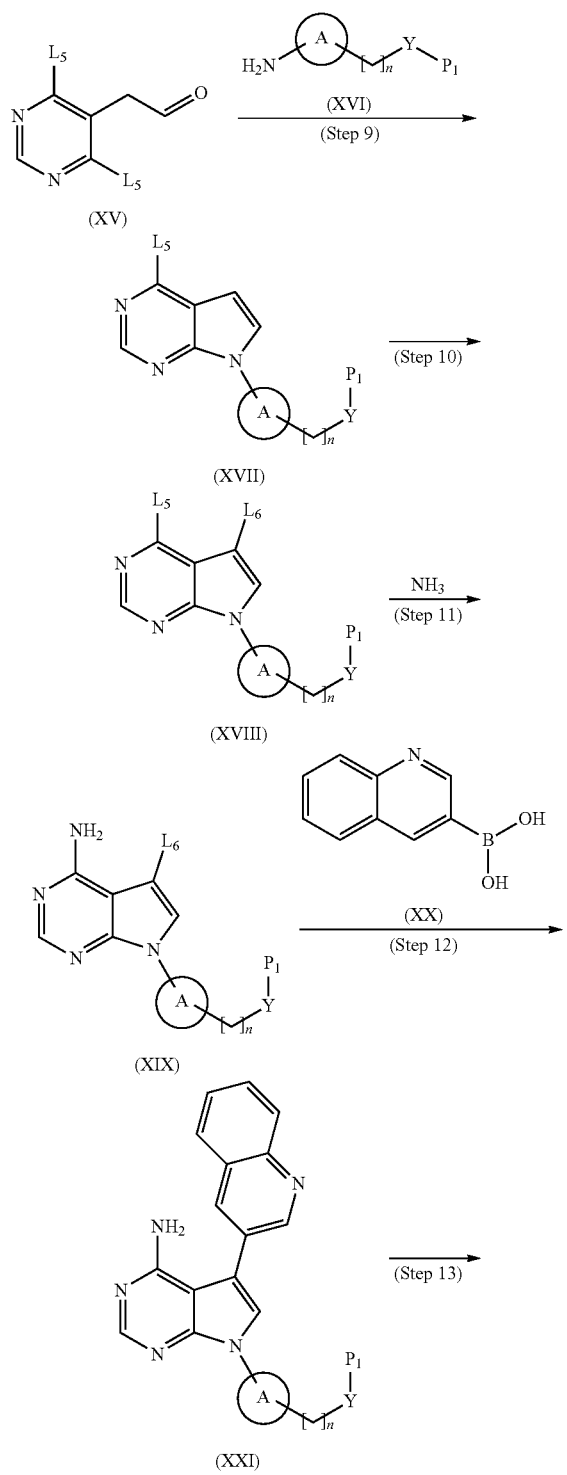

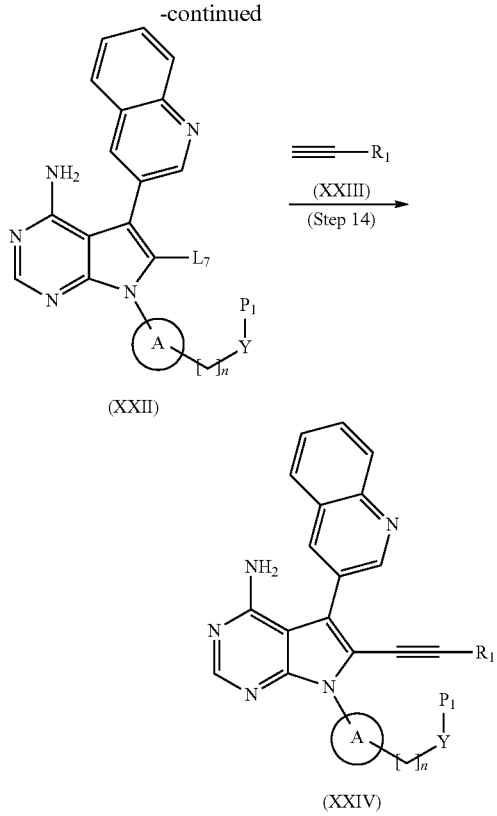

wherein Y represents NH or O, $P_1$ represents a hydrogen atom or a protective group for an amino group, $L_5$, $L_6$, and $L_7$ each represent a leaving group, and $R_1$, the ring A and n are as defined above.

(Step 9)

This step is configured to react a compound represented by general formula (XV) with a compound represented by general formula (XVI) in the presence of a base to thereby prepare a compound represented by general formula (XVII).

In general formula (XV), the leaving group represented by $L_5$ is a fluorine atom or a chlorine atom. The compounds represented by general formulae (XV) and (XVI) may be commercially available products or may be prepared according to known procedures.

The compound represented by general formula (XVI) may be used in an amount of 1 to 10 moles, preferably 1 to 3 moles, relative to 1 mole of the compound represented by general formula (XV).

Examples of a base available for use in this step include an organic base (e.g., triethylamine, diisopropylethylamine, pyridine) or an inorganic base (e.g., sodium bicarbonate, sodium carbonate, potassium carbonate, cesium carbonate, sodium hydroxide, potassium phosphate, potassium tert-butyrate).

The amount of such a base to be used is usually 1 mole to excess moles, preferably 1 to 3 moles, relative to 1 mole of the compound represented by general formula (XV).

The reaction solvent is not limited in any way as long as it is inert to the reaction, and preferred examples include tetrahydrofuran, 1,4-dioxane, 1,2-dimethoxyethane, dimethyl sulfoxide, dimethylformamide, N-methylpyrrolidone, etc., methanol, ethanol, isopropanol, or mixed solvents thereof.

The reaction temperature is usually 0° C. to 200° C., and preferably 50° C. to 120° C.

The reaction time is usually 5 minutes to 7 days, and preferably 30 minutes to 24 hours.

(Step 10)

This step is configured to halogenate the compound represented by formula (XVII) in the presence or absence of a base to thereby prepare a compound represented by formula (XVIII).

In general formula (XVIII), the leaving group represented by $L_6$ is a chlorine atom, a bromine atom or an iodine atom.

This step may be carried out using N-chlorosuccinimide, N-bromosuccinimide, N-iodosuccinimide, bromine, and iodine, etc.

The solvent is not limited in any way as long as it is inert to the reaction, but the reaction may be carried out in an appropriate solvent inert to the reaction, as exemplified by acetonitrile, ethyl acetate, tetrahydrofuran, methanol, ethanol, dimethylformamide, dimethylacemide, N-methylpyrroidone, etc.

Examples of a base available for use include an organic base (e.g., diisopropylethylamine, pyridine, tetrabutylammonium fluoride) or sodium bicarbonate, sodium carbonate, potassium carbonate, cesium carbonate, sodium hydroxide, sodium hydride, potassium phosphate, sodium phosphate, potassium tert-butyrate, etc.

The reaction temperature is usually 0° C. to 100° C., and preferably room temperature to reflux temperature.

The reaction time is usually 10 minutes to 3 days, and preferably 30 minutes to 24 hours.

(Step 11)

This step is configured to react the compound represented by general formula (XVIII) with ammonia or a salt thereof to thereby prepare a compound represented by general formula (XIX).

The amount of ammonia or a salt thereof to be used in this step is usually equimolar to excess moles, relative to 1 mole of the compound represented by general formula (XVIII).

The reaction solvent is not limited in any way as long as it is inert to the reaction, and preferred examples include water, methanol, ethanol, isopropanol, tetrahydrofuran, 1,4-dioxane, 1,2-dimethoxyethane, dimethylformamide, N-methylpyrrolidone, dimethyl sulfoxide, etc., or mixed solvents thereof.

The reaction temperature is usually 0° C. to 200° C., and preferably 70° C. to 120° C.

The reaction time is usually 5 minutes to 7 days, and preferably 1 hour to 24 hours.

(Step 12)

This step is configured to cause coupling, reaction between the compound represented by general formula (XIX) and 3-quinolineboronic acid (general formula (XX)) to thereby prepare a compound represented by structural formula (XXI).

This step may be carried out according to generally known procedures (e.g., Chemical Reviews, Vol. 95, p. 2457, 1995), for example, may be carried out in the presence of a transition metal catalyst and a base in a solvent not adversely affecting the reaction.

The amount of 3-quinolineboronic acid to be used is 1 to 10 moles, preferably 1 to 3 moles, relative to 1 mole of the compound represented by general formula (XIX).

Examples of a transition metal catalyst available for use include palladium catalysts (e.g., palladium acetate, palladium chloride, tetrakis(triphenylphosphine) -palladium, 1,1'-bis(diphenylphosphino)ferrocene-palladium(II) dichloride, chloro(2-dicyclohexylphosphino-2',4',6'-triisopropyl-1,1'-biphenyl)[2-(2'-amino-1,1'-biphenyl)]palladium(II)), nickel catalysts (e.g., nickel chloride), etc. If required, a ligand (e.g., triphenylphosphine, tri-tert-butylphosphine) may be added, and a metal oxide (e.g., copper oxide, silver oxide) or the like may be used as a co-catalyst.

The amount of such a transition metal catalyst to be used will vary depending on the type of catalyst, but it is usually 0.0001 to 1 mole, preferably 0.01 to 0.5 moles, relative to 1 mole of the compound represented by general formula (XIX). The amount of such a ligand to be used is usually 0.0001 to 4 moles, preferably 0.01 to 2 moles, relative to 1 mole of the compound represented by general formula (XIX), while the amount of such a co-catalyst to be used is usually 0.0001 to 4 moles, preferably 0.01 to 2 moles, relative to 1 mole of the compound represented by general formula (XIX).

Examples of a base include oraanic amine compounds (e.g., trimethylamine, triethylamine, diisopropylethylamine), alkali metal salts (e.g., sodium bicarbonate, sodium carbonate, potassium carbonate, cesium carbonate, potassium phosphate, sodium hydroxide), metal hydrides (e.g., potassium hydride, sodium hydride), alkali metal alkoxides (e.g., sodium methoxide, sodium etboxide, potassium tert-butoxide), etc.

The amount of such a base to be used is usually 0.1 to 10 moles, preferably 1 to 5 moles, relative to 1 mole of the compound represented by general formula (XIX).

Any solvent may be used as tom as it does not adversely affect the reaction, and examples include hydrocarbon-based solvents (e.g., benzene, toluene, xylene), halogenated hydrocarbon-based solvents (e.g., chloroform, 1,2-dichloroethane), nitrile -based solvents (e.g., acetonitrile), ether-based solvents (e.g., 1,2-dimethoxyethane, tetrahydrofuran, 1,4-dioxane), alcohol-based solvents (e.g., methanol, ethanol), aprotic polar solvents (e.g., dimethylformamide, dimethyl sulfoxide), water, or mixtures thereof.

The reaction temperature is usually 0° C. to 200° C., and preferably 60° C. to 120° C.

The reaction time is usually 5 minutes to 7 days, and preferably 1 hour to 24 hours.

(Step 13)

This step is configured to halogenate the compound represented by formula (XXI) in the presence or absence of a base to thereby prepare a compound represented by formula (XXII).

In general formula (XXII), the leaving group represented by $L_7$ is a chlorine atom, a bromine atom or an iodine atom.

This step may be carried out using N-chlorosuccinimide, N-bromosuccinimide, N-iodosuccinimide, bromine, and iodine, etc.

The solvent is not limited in any way as long as it is inert to the reaction, but the reaction may be carried out in an appropriate solvent inert to the reaction, as exemplified by acetonitrile, ethyl acetate, tetrahydrofuran, methanol, ethanol, dimethylformamide, dimehtylacetamide, N-methylpyrrolidone, etc.

Examples of a base available for use include an organic base (e.g., diisopropylethylamine, pyridine, tetrabutylammonium fluoride) or sodium bicarbonate, sodium carbonate, potassium carbonate, cesium carbonate, sodium hydroxide, sodium hydride, potassium phosphate, sodium phosphate, potassium tert-butyrate, etc.

The reaction temperature is usually 0° C. to 100° C., and preferably room temperature to reflux temperature.

The reaction time is usually 10 minutes to 3 days, and preferably 30 minutes to 24 hours.

(Step 14)

This step is configured to cause Sonogashira reaction between the compound represented by formula (XXII) and a compound represented by formula (XXIII) to thereby prepare a compound represented by formula (XXIV).

The Sonogashira reaction may be carried out according to generally known procedures (e.g., as described in Chemical Reviews, Vol. 107, p. 874 (2007)) or similar procedures, for example, may be carried out in the presence of a transition metal catalyst and a base in a solvent not adversely affecting the reaction.

Examples of a transition metal catalyst available for use include palladium catalysts (e.g., palladium acetate, palladium chloride, tetrakis(triphenylphosphine) -palladium, dichlorobis(triphenylphosphine)palladium, dichloro[1,1'-diphenyl -phosphino)ferrocene]palladium, tris(dibenzylideneacetone)dippalladium(0)), copper catalysts (e.g., copper bromide, copper iodide) and so on, which may be used either alone or in combination.

The amount of such a transition metal catalyst available for use is suitably within the range of 0.001 to 1 mole, relative to 1 mole of the compound represented by formdla (XXII).

If necessary, a ligand for palladium may be used, as exemplified by triphenylphosphine, tri(2-furyl)phosphine, 1,1'-bis(diphenylphosphino)ferrocene, 4,5-bis(diphenylphosphino)-9,9'-dimethylxanthene, 2-dicyclohexylphosphino-2',4',6'-triisopropylbiphenyl, 2-dicyclohexylphosphino-2',6'-dimethyoxybiphenyl, 2-di-tert -butylphosphino-3,4,5,6-tetramethyl-2',4',6'-tri-i-propylbiphenyl, etc.

The reaction solvent available for use is not limited in any way as long as it is inert to the reaction, and examples include tetrahydrofuran, 1,4-dioxane, 1,2-dimethoxyethane, N,N-dimethylformamide, N,N-dimethylacetamide, N-methyl-2-pyrrolidone, benzene, toluene, acetonitrile, dimethyl sulfoxide, water, or mixed solvents thereof.

Examples of a base available for use in this step include an organic base (e.g., triethylamine, diisopropylethylamine, pyridine, 4-dimethylaminopyridine) or an inorganic base (e.g., sodium bicarbonate, sodium carbonate, potassium carbonate, cesium carbonate, sodium hydroxide, sodium hydride, potassium phosphate, sodium phosphate, potassium tert-butyrate).

The reaction tune is usually 5 minutes to 7 days, and preferably 30 minutes to 24 hours.

The reaction temperature is usually 25° C. to 200° C., and preferably 30° C. to 100° C.

[Preparation Process 3]

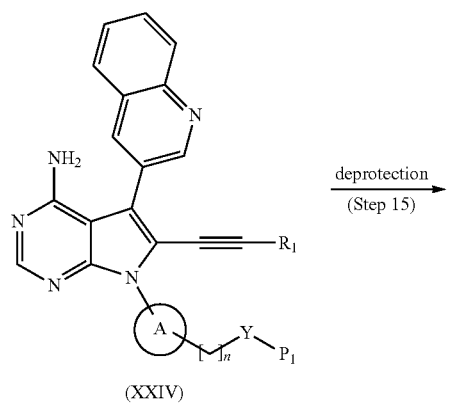

(XXIV)

deprotection
(Step 15)

-continued

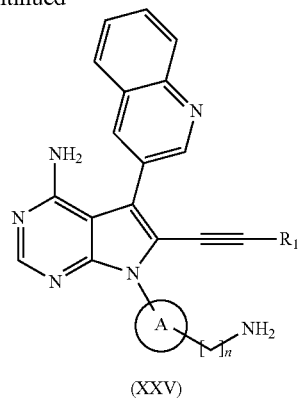

(XXV)

wherein Y represents NH, $P_1$ represents a protective group for an amino group, and the ring A, $R_1$ and n are as defined above.

(Step 15)

This step is configured to deprotect the amino group protection the compound represented by formula (XXIV) to thereby prepare a compound represented by formula (XXV).

Deprotection may be carried out according to generally known procedures (e.g., as described in Protective Groups in Organic Synthesis, T. W. Greene, John Wiley & Sons (1981)) or similar procedures.

When a tert-butoxycarbonyl group is used as a protective group, a deprotection reagent may be exemplified by hydrochloric acid, sulfuric acid, methanesulfonic acid, trifluoroacetic acid, etc. The amount of such a reagent to be used is preferably 1 to 100 moles, relative to 1 mole of compound (XXIV).

Any solvent may be used in the reaction as long as it does not adversely affect the reaction, and examples include water, methanol, ethanol, methylene chloride, chloroform, etc., or mixed solvents thereof.

The reaction temperature is usually 0° C. to 200° C. and preferably 0° C. to 0° C.

The reaction time is usually 5 minutes to 7 days, and preferably 1 hour to 48 hours.

[Preparation Process 4]

(Step 16)

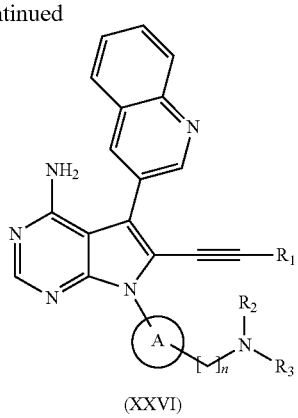

(XXVI)

wherein the ring A, $R_1$, $R_2$, $R_3$ and n are as defined above.

(Step 16)

This step is configured to cause acylation reaction of the compound represented by general formula (XXV) with a carboxylic acid, an acid halide, an acid anhydride, an isocyanate, an isothiocyanate or an amine to prepare the compo d of the present invention represented by general formula (XXVI).

The above acylating reagent is used in an amount of 0.5 to 10 moles, preferably 1 to 3 moles, relative to 1 mole of the compound represented by general formula (XXV). It should be noted that such an acylating reagent may be a commercially available product or may be prepared according to known procedures.

The reaction solvent is not limited in any way as long as it is inert to the reaction, and preferred examples include toluene, benzene, methylene chloride, chloroform, tetrahydrofuran, 1,4-dioxane, N,N-dimethylformamide, dimethylacetamide, N-methylpyrrolidin-2-one, dimethyl sulfoxide, etc., or mixed solvents thereof.

The reaction temperature is usually −78° C. to 200° C., and preferably 0° C. to 70° C.

The reaction time is usually 5 minutes to 3 days, and preferably 5 minutes to 10 hours.

In the reaction, a condensing agent may be used as needed, and examples of a condensing agent include diphenylphosphotyl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)-carbodiimide, 1-ethyl-3-(3-dimethylaminopropyl)carbodiimide in combination with 1-hdroxybenzotriazole, 2-chloro-1,3-dimethylimidazolinium chloride, O-(7-azabenzotriazo-1-yl)-N,N,N',N'-tetramethylhexauronium hexafluorophosphate, carbonyldiimidazole, etc.

Moreover, in the above reaction, a base may be added as needed. Examples of a base include an organic base (e.g., triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, butyllithium) or an inorganic base (e.g., sodium bicarbonate, sodium carbonate,, potassium carbonate, cesium carbonate, sodium hydroxide, sodium hydride). The amount of such a base to be added is 1 to 100 moles, preferably 1 to 10 moles, relative to 1 mole of the compound represented by general fommla (XXV).

Alternatively, in this step, the compound represented by general formula (XXV) may be reacted with an alkyl halide in the presence of a base to prepare the compound represented by general fonnula (XXVI).

The alkyl halide is used in an amount of 0.5 to 10 moles, preferably 1 to 3 moles, relative to 1 mole of the compound represented by gene al formula (XXV). It should be noted that such an alkyl halide may be a commercially available product or may be prepared according to known procedures.

The reaction solvent is not limited in any way as long as it is inert to the reaction, and preferred examples include toluene, benzene, methylene chloride, chloroform, tetrahydrofuran, 1,4-dioxane, N,N-dimethylformamide, dimethylacetamide N-methylpyrrolidin-2-one, dimethyl sulfoxide, etc., or mixed solvents thereof.

Examples of a base include an organic base (e.g., triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, butyllithium) or an inorganic base (e.g., sodium bicarbonate, sodium carbonate, potassium carbonate, cesium carbonate, sodium hydroxide, sodium hydride). The amount of such a base to be added is 1 to 100 moles, preferably 1 to 10 moles, relative to 1 mole of the compound represented by general formula (XXV).

The reaction temperature is usually −78° C. to 200° C., and preferably 50° C. to 100° C.

The reaction tune is usually 5 minutes to 3 days, and preferably 5 minutes to 10 hours.

Alternatively, in this step, the compound represented by general formula (XXV) and an aldehyde reagent may be subjected to reductive amination reaction in the presence of a reducing agent to thereby prepare the compound represented by general formula (XXVI).

The aldehyde reagent is used in an amount of 0.5 to 10 moles, preferably 1 to 3 moles, relative to 1 mole of the compound represented by general formula (XXV). It should be noted that such an aldehyde reagent may be a commercially available product or may be prepared according to known procedures.

The reducing agent is not limited in any way, and examples include metal hydride complexes, as exemplified by 0.1 moles to a large excess of sodium borohydride, sodium cyanoborohydride, hydrogenated triacetoxyborohydride, etc.

In the reaction, additives may be added as needed, and examples include acids, bases, inorganic or organic salts, as exemplified by 0.01 moles to a large excess of trifluoroacetic acid, formic acid, acetic acid, hydrochloric acid, potassium carbonate, sodium hydroxide, lithium hydroxide, sodium sulfate, magnesium sulfate, tetraisopropyl orthotitanate, zinc chloride, etc.

The reaction solvent is not limited in any way as long as it is inert to the reaction, and preferred examples include toluene, methylene chloride, chloroform, tetrahydrofuran, 1,4-dioxane, N,N-dimethylformamide, dimethylacetamide, N-methylpyrrolidin-2-one, dimethyl sulfoxide, methanol, ethanol, 2-propanol, tert-butyl alcohol, etc., or mixed solvents thereof.

The reaction temperature is usually −78° C. to 200° C., and preferably 0° C. to 60° C.

The reaction time is usually 5 minutes to 3 days, and preferably 5 minutes to 10 hours.

If the compound of the present invention has optical isomers, stereoisomers, rotational isomers, tautomers and other isomers, all of these isomers and mixtures thereof also fill within the compound of the present invention, unless otherwise specified. For example, if the compound of the present invention has optical isomers, the racemic mixture and optical isomers resolved therefrom also fall within the compound of the present invention, unless otherwise specified.

A salt of the compound of the present invention is intended to mean a pharmaceutically acceptable salt, as exemplified by a base addition salt or an acid addition salt.

The compound of the present invention or a salt thereof may be in either amorphous or crystalline form, and the crystalline form may be a single crystalline form or a polymorphic mixture, both of which fall within the compound of the present invention or a salt thereof. Such crystalline forms may be prepared by being crystallized with the application of known crystallization techniques. The compound of the present invention or a salt thereof may be either a solvate (e.g., a hydrate) or a non-solvate, both of which fall within the compound of the present invention or a salt thereof. The compound of the present invention or a salt thereof also encompasses those labeled with isotopes (e.g., $^3$H, $^{14}$C, $^{35}$S, $^{125}$I), etc.

For pharmaceutical use of the compound of the present invention ora salt thereof, a pharmaceutically acceptable carrier may be incorporated as needed, and various dosage forms can be selected as appropriate for prophylactic or therapeutic purposes. Such dosage forms may be exemplified by oral formulations, injections, suppositories, ointments, patches, etc., and oral formulations are preferably selected. These dosage forms may each be prepared by formulation techniques which are known to and conventionally used by those skilled in the art.

One embodiment of the present invention provides an antitumor agent comprising the compound of the present invention or a pharmaceutically acceptable salt thereof as an active ingredient. In one embodiment of the present invention, the antitumor agent is an antitumor agent for oral administration. Moreover, one embodiment of the present invention provides a method for the prevention and/or treatment of tumor, which comprises administering an effective amount of the compound of the present invention or a pharmaceutically acceptable salt thereof to a subject in need thereof. Moreover, one embodiment of the present invention provides a method for the prevention and/or treatment of tumor, which comprises orally administering an effective amount of the compound of the present invention or a pharmaceutically acceptable salt thereof to a subject in need thereof. Moreover, one embodiment of the present invention provides the use of the compound of the present invention or a pharmaceutically acceptable salt thereof for the manufacture of an antitumor agent. Moreover, one embodiment of the present invention provides the use of the compound of the present invention or a pharmaceutically acceptable salt thereof for the manufacture of an antitumor agent for oral administration. Moreover, one embodiment of the present invention provides the compound of the present invention or a pharmaceutically acceptable salt thereof for use in the prevention and/or treatment of tumor. Moreover, one embodiment of the present invention provides the compound of the present invention or a pharmaceutically acceptable salt thereof for use by oral administration in the prevention and/or treatment of tumor.

As used herein, the term "effective amount" of the compound of the present invention refers to the amount (therapeutically effective amount) of the compound of the present invention, which is required to cause biological or medical responses (e.g., reduction or inhibition of enzyme and/or protein activity) in a subject or which is required to ameliorate symptoms, alleviate conditions, slow or delay the progress of a disease, or prevent a disease, etc.

As used herein, the term "subject" encompasses mammals and non-mammals. Examples of mammals include, but are not limited to, humans, chimpanzees, anthropoids, monkeys, cows, horses, sheep, goats, pigs, rabbits, dogs, cats, rats, mice, guinea pigs, hedgehogs, kangaroos, moles, wild boars, bears, tigers, lions and so on. Examples of non-mammals include, but are not limited to, birds, fishes, reptiles and so on. In one embodiment, the subject is a human, and may be a human who has been diagnosed as being in need of treatment for the symptoms, conditions or diseases disclosed herein.

One embodiment of the present invention provides a pharmaceutical composition comprisine the compound of the present invention or a salt thereof. A pharmaceutical composition according to one embodiment of the present invention comprises the compound of the present invention or a pharmaceutically acceptable salt thereof, and a pharmaceutically acceptable carrier. Moreover, one embodiment of the present invention provides the use of the compound of the present invention or a salt thereof for the manufacture of a pharmaceutical composition. Another one embodiment of the present invention provides the compound of the present invention or a salt thereof for pharmaceutical use.

For pharmaceutical use of the compound of the present invention or a salt thereof, a pharmaceutically acceptable carrier may be incorporated as needed, and various dosage forms can be selected as appropriate for prophylactic or therapeutic purposes. Such dosage rams may be exemplified by oral formulations, injections, suppositories, ointments, patches, etc., and oral formulations are preferably selected. These dosage forms may each be prepared by formulation techniques which are known to and conventionally used by those skilled in the art.

Examples of a pharmaceutically acceptable carrier available for use include various organic or inorganic carrier substances conventionally used as formulation materials, winch may be incorporated as excipients, binders, disintegrants, lubricants, coating agents and/or coloring agents in solid formulations, or as solvents, solubilizers, suspending agents, isotonizing agents, buffering agents and/or soothing agents in liquid formulations, etc. Moreover, formulation additives may also be used as needed, as exemplified by antiseptics, antioxidants, sweeteners, stabilizers, etc.

In the case of preparing oral solid formulations, the compound of the present invention may be mixed with an excipient and optionally with a binder, a disintegrant, a lubricant, a coloring agent, a corrective, etc., and then formulated in a standard manner to prepare tablets, coated tablets, granules, powders, capsules, etc.

In the case of preparing injections, the compound of the present invention may be mixed with a pH adjuster, a buffering agent, a stabilizer, an isotonizing agent, a local anesthetic agent, etc., and then formulated in a standard manner to prepare injections for subcutaneous, intramuscular and intravenous use.

The amount of the compound of the present invention to be incorporated into the above dosage unit forms will vary depending on, e.g., the symptom of a subject to be applied thereby and each dosage form. However, in general, it is preferably 0.05 to 1000 mg for oral formulations. 0.01 to 500 mg for injections, and 1 to 1000 mg for suppositories, per dosage unit form.

Moreover, the daily dose of formulations in the above dosage forms will vary depending on, e.g., the symptom, body weight, age and/or sex of a subject, and cannot be determined simply. However, the daily dose for adults (body weight: 50 kg) may usually be 0.05 to 5000 mg, preferably 0.1 to 1000 mg, calculated as the compound of the present invention.

The tumor intended in the present invention is not limited in any way, and examples include head and neck cancer, digestive organ cancer (esophageal cancer, gastric cancer, duodenal cancer, liver cancer, biliary tract cancer (e.g., gallbladder and bile duct cancer), pancreatic cancer, large bowel cancer (e.g., colorectal cancer, colon cancer, rectal cancer, anal cancer)), lung cancer (non-small cell lung cancer, small cell lung cancer, mesothehoma (e.g,. pleural mesothelioma, peritoneal mesothelioma, pericardial mesothelioma, testicular mesothelicima)), breast cancer, genital cancer (e.g., ovarian cancer, vulvar cancer, uterine cancer (e.g., uterine cervical cancer, uterine body cancer, endometrial cancer)), urinary organ cancer (e.g., renal cancer, bladder cancer, prostate cancer, testicular tumor, urothelial cancer, renal pelvis cancer, urethral cancer), hematopoietic tumor (e.g., leukemia, malignant lymphoma, multiple myeloma), bone and soft tumor, rhabdomyosarcoma, skin cancer, brain tumor, malignant neurilemmoma, neuroendocrine tumor, thyroid cancer, etc. Preferred are head rand neck cancer, breast cancer, large bowel cancer, esophageal cancer, pancreatic cancer, lung cancer, ovarian cancer, renal cancer, bladder cancer, skin cancer and brain tumor, and particularly preferred is lung cancer. It should be noted that the cancer intended here includes not only its primary focus, but also cancer metastasized to other organs (e.g., the liver). Further, the compound of the present invention or a salt thereof has significant inhibitory activity against mutated EGFR. Examples of such mutated EGFR include drug-resistant mutated EGFR and highly susceptible mutated EGFR. For this reason, the compound of the present invention or a salt thereof is also useful as an antitumor agent for the above malignant tumors having mutated EGFR.

The compound according to one embodiment of the present invention or a salt thereof has significant EGFR inhibitory activity and, in particular, has significant inhibitory activity against EGFR (Del19/C797S), EGFR (L858R/C797S), EGFR (Del19/T790M/C797S) or EGFR (L858R/T790M/C797S) and is useful as an antitumor agent. The compound according to one embodiment of the present invention or a salt thereof also has significant selectivity for mutated EGFR and is advantageous in terms of fewer side effects due to wild-type EGFR and other kinases.

As used herein, the term "wild-type EGFR" is represented, for example, by the amino acid sequence of GenBank Accession No. NP_005219.2.

As used herein, the term "exon 19" refers to a region at positions 729 to 823 in the amino acid sequence of wild-type EGFR (e.g., GenBank Accession No. NP_005219.2).

As used herein, the term "Del19" to a mutation with a deletion of one or more amino acids in the exon 19 region of wild-type EGFR. In addition to a deletion in this region, this mutation may comprise an insertion of one or more any amino acids. Examples of such an exon 19 deletion mutation include a mutation with a deletion of 5 amino acids covering from glatamic acid at position 746 to alanine at position 750 in the exon 19 region (Del E746-A750 (or also referred to as d746-750)), a mutation with a deletion of 7 amino acids covering from leucine at position 747 to proline at position 753 in the exon 19 region and an insertion of serine (Del 747-P753insS), a mutation with a deletion of 5 amino acids covering from leucine at position 747 to threonine at position 751 in the exon 19 region (Del L747-T751), a mutation with a deletion of 4 amino acids covering from leucine at position 747 to alanine at position 750 in the exon 19 region and an insertion of proline (Del 747-A750insP), etc. Preferred is a mutation with a deletion of 5 amino acids covering from glutamic acid at position 746 to alanine at position 750 in the exon 19 region (Del E746-A750).

EXAMPLES

The present invention will be further described in more detail by way of the following examples and test examples, which are not intended to limit the present invention.

The various reagents used in the Example section were commercially available products, unless otherwise specified. For silica gel column chromatography and basic silica gel column chromatography, prepacked columns available from Shoko Scientific Co., Ltd. (Japan) or Biotage were used.

Reversed-phase preparative HPLC column chromatography was done under the conditions shown below. The injection volume and gradient were determined as appropriate.

Column: CAPCELL PAK C18 MGIII (OSAKA SODA), 30×50 mm, 5 μm
UV detection: 254 nm
Column flow rate: 40 mL/min
Mobile phase: water/acetonitrile (0.1% formic acid)
Injection volume: 0.1 to 1.0 mL
Gradient: water/acetonitrile 10% →90% (7 minutes).

NMR spectra were measured with a spectrometer of model AL400 (400 MHz; JEOL), Mercury 400 (400 MHz; Agilent Technology), AVANCE NEO (400 MHz; Bruker) or AVANCE III HD (500 MHz; Bruker) using tetramethylsilane as an internal standard in the case of containing tetramethylsilane in a denterated solvent or using an NMR solvent as an internal standard in the other cases, and all δ values were expressed in ppm.

Likewise, LCMS spectra were measured with a SQD detector (Waters) under the two conditions shown below, and [M+H]+ values were shown.
MS detection: ESI positive
UV detection: 254 and 210 nm
Column flow rate: 0.5 mL/min
Mobile phase: water/acetonitrile (0.1% formic acid)
Injection volume: 1 μL
Column: Acquits BEH, 2.1×50 mm, 1.7 μm

| Gradient: | |
|---|---|
| Time (min) | Water/Acetonitrile (0.1% formic acid) |
| 0 | 95 5 |
| 0.1 | 95 5 |
| 2.1 | 5 95 |
| 3.0 | STOP |

The meanings of abbreviations are shown below.
s: singlet
d: doublet
t: triplet
q: quartet
dd: double doublet
m: multiplet
br: broad
brs: broad singlet
DMSO-d6: deuterated dimethyl sulfoxide CDCl3: deuterated chloroform
THF: tetrahydrofuran
DMF: N,N-dimethylformamide
DMA: N,N-dimethylacetamide
DME: 1,2-dimethoxyethane
DMSO: dimethyl sulfoxide
HATU: O-(7-azabenzotriazol-1-yl)-N,N,N',N'-tetramethylhexauronium hexafluorophosphate
DIPEA: diisopropylethylamine
TBAF: tetrabutylammonium fluoride
NMP: N-methylpyrrolidin-2-one
DMPU: N,N-dimethylpropyleneurea
WSC: 1-(3-dimethylaminopropyl)-3-ethylcarbodiimide hydrochloride
HOBT: 1-hydroxybenzotriazole
NBS: N-bromosuccinimide

[Preparation Example 1]

Preparation of 7-(4-aminobicyclo[2.2.1]heptan-1-yl)-6-ethynyl-5-(quinolin-3-yl)-7H -pyrrolo[2,3-d]pyrimidine-4-amine (Step 1)
A mixture of 4,6dichloro-5-iodopyrimidine (0.38 g), tert-butyl (4-aminobicyclo[2.2.1]heptan-1-yl)carbamate (0.30 g), DIPEA (0.69 and THF (3 ml) wa stirred at 70° C. for overnight. The reaction mixture was cooled to room temperature and then concentrated. The resulting residue was purified by silica gel column chromatography to obtain tert-butyl (4-((6-chloro-5-iodopyrimidin-4-yl)amino)bicyclo[2.2.1]heptan-1-yl)carbamate (Preparation Example (1-1)).

(Step 2)
A mixture of the compound of Preparation Example (1-1) (390 mg), tri(2-furyl)phosphine (39 mg), tris(dibenzylideneacetone)dipalladium(0) (38 mg), copper(I) iodide (32 mg), propargyl aldehyde diethyl acetal (0.24 ml), DIPEA (0.22 ml) and DMF (5.9 ml) was stirred at 70° C. for 3 hours, The reaction mixture was cooled to room temperature, diluted with ethyl acetate, and then washed with water and saturated brine. The organic layer was dried over anhydrous magnesium sulfate, then filtered, and the filtrate was concentrated. The resulting residue was purified by silica gel column chromatography to obtain tert-butyl (4-((6-chloro-5-(3,3-diethoxypropyn-1-yl)pyrimidin-4-yl)amino)bicyclo [2.2.1]heptan-1-yl)carbamate (Preparation Example (1-2)).

(Step 3)
A mixture of the compound of Preparation Example (1-2) (325 mg), TBAF (1 M in THF, 0.7 ml) and THF (3.5 ml) was stirred at 70° C. for 1 hour. The reaction mixture was cooled to room temperature and then concentrated, and the resulting residue was purified by silica gel column chromatography to obtain (4-(4-chloro-6-(diethoxymethyl)-7H-pyrrolo[2,3-d]pyrimidin-7-yl)bicyclo[2.2.1]heptan-1-yl)carbamate (Preparation Example (1-3)).

(Step 4)
To a mixture of the compound of Preparation Example (1-3) (329 mg) and DMF (3.3 ml), NBS (72 mg) was added at room temperature, followed by stirring for 1 hour. The reaction mixture was diluted with saturated aqueous sodium sulfite, and then extracted with ethyl acetate. The organic layer was washed with water and saturated brine, dried over anhydrous magnesium sulfate and then filtered, and the filtrate was concentrated. The resulting residue was purified by silica gel column chromatography to obtain tert-butyl (4-(5-bromo-4-chloro-6-(diethoxymethyl)-7H -pyrrolo[2,3-d]pyrimidin-7-yl)bicyclo[2.2.1]heptan-1-yl)carbamate (Preparation Example (1 -4)).

(Step 5)
A mixture of the compound of Preparation Example (1-4) (358 mg), DME (2 ml) and aqueous ammonia (2 ml) was placed into a pressure reaction vessel and stirred at 90° C. for 12 hours. The reaction mixture was cooled to room temperature and extracted with ethyl acetate, and the organic layer was then concentrated. To the resulting residue, THF (1.8 nil), acetic acid (1.8 ml) and water (0.4 ml) were added, and then stirred at 45° C. for 16 hours. After concentration, the reaction mixture was neutralized with saturated aqueous sodium bicarbonate, and then extracted with ethyl acetate. The organic layer was dried over anhydrous magnesium sulfate and then filtered, and the filtrate was concentrated. The resulting residue was purified by silica gel column chromatography to obtain tert-butyl (4-(4-amino-5-bromo-6-formyl-7H -pyrrolo[2,3-d]pyrimidin-7-yl)bicyclo[2.2.1] heptan-1-yl)carbamate (Preparation Example (1-5)).

(Step (6)
A mixture of the compound of Preparation Example (1-5) (4.1 g), 3-quinolineboronic acid (1.8 g), tetrakis(triphenylphosphine)palladium(0) (406 (mg), sodium carbonate (2.1 g), DME (4 ml) and water (21 ml) was heated at reflux under a nitrogen atmosphere for 2 hours. The reaction mixture was cooled to room temperature, and extracted with ethyl acetate. The organic layer was dried over anhydrous magnesium sulfate and then filtered, and the filtrate was concentrated. The resulting residue was purified by silica gel column chromatography to obtain tert-butyl (4-(4-amino-6-formyl-5-(quinolin-3-yl)-7H-pyrrolo[2,3-d]pyrimidin-7-yl) bicyclo -[2.2.1]heptan-1-yl)carbamate (Preparation Example (1-6)).

(Step 7)
A mixture of the compound of Preparation Example (1-6) (3.9 g), dimethyl (1-diazo-2-oxopropyl)phosphonate (4.8 ml), potassium carbonate (3.3 g) and methanol (60 ml) was stirred for overnight at room temperature. The reaction mixture was diluted with water and extracted with ethyl acetate. The organic layer was dried over anhydrous magnesium sulfate, and then filtered, and the filtrate was concentrated. The resulting residue was purified by silica gel column chromatography to obtain tert-butyl (4-(4-amino-6-ethynyl-5-(quinolin-3-yl)-7H-pyrrolo[2,3-d]pyrimidin-7-yl) bicyclo -[2.2.1]heptan-1-yl)carbamate (Preparation Example (1-7)).

(Step 8)
To a solution of the compound of Preparation Example (1-7) in dichloromethane (40 ml), trifluaroacetic acid (40 ml) was added, followed by stirring at room temperature for 10 minutes. The reaction mixture was diluted with water, neutralized with aqueous sodium hydroxide, and then extracted with ethyl acetate for three times. The organic layers were washed with saturated brine, dried over anhydrous magnesium sulPate and then filtered, and the filtrate was concentrated. The resulting residue was purified by basic silica gel column chromatography to obtain the above titled compound (7-(4-aminobicyclo[2.2.1]heptan-1-yl)-6-ethynyl-5-(quinolin-3-yl)-7H-pyrrolo[2,3-d]pyrimidin-4-amine).

[Preparation Example 2]

Preparation of (7-(4-aminobicyclo[2.2.2]octan-1-yl)-6-ethynyl-5-(quinolin-3-yl)-7H -pyrrolo[2,3-d]pyrimidin-4-amine The same procedures as shown in Preparation Example 1 (Steps 1 to 8) were repeated to obtain the above tided compound (7-(4-aminobicyclo[2.2.2]octan-1-yl)-6ethynyl-5-(quinolin-3-yl)-)-7H-pyrrolo[2,3-d]pyrimidin-4-amine), except that tert-butyl (4-aminobicyclo[2.2.1]heptan-1-yl)carbamate used in Step 1 of Preparation Example 1 was replaced with tert-butyl (4-aminobicyclo[2.2.2]octan-1-yl)carbamate.

[Preparation Example 3]

Preparation of tert-butyl (4-(4-amino-6-bromo-5-(quinolin-3-yl)-7H-pyrrolo[2,3-d]pyrimidin-7-yl)bicyclo[2.2.1]heptan-1-yl)carbamate (Step 1)
A mixture of 2-(4,6-dichloropyrimidin-5-yl)acetaldehyde (4.6 g), tert-butyl (4-aminobicyclo[2.2.1]heptan-1-yl)carbamate (5.0 g), DIPEA (7.7 ml) and acetonitrile (50 ml) vas stirred at 100° C. for 2 hours. The reaction mixture was cooled to room temperature and then concentrated. After the reaction mixture was diluted with ethyl acetate (50 ml) and ,ater (10 ml), insoluble materials were filtered off. The organic layer was washed sequentially with saturated brine, aqueous ammonium chloride and saturated brine dried over anhydrous magnesium sulfate and then concentrated to obtain crude tert-butyl (4-(4-chloro-7H-pyrrolo[2,3-d]pyrimidin-7-yl)bicyclo[2.2.1]heptan-1-yl)carbamate (Preparation Example (3-1)).

(Step 2)
To a solution of the compound of Preparation Example (3-1) in NMP (50 ml), NBS (4.3 g) was added at 0° C., followed by stirring at room temperature for 30 minutes. To the reaction mixture, saturated aqueous sodium sulfite (5 ml) and water (100 ml) were gradually added, followed by stirring for 10 minutes. The resulting solid was collected by filtration and washed with water to obtain tert-butyl (4-(5-bromo-4-chloro -7H-pyrrolo[2,3-d]pyrimidin-7-yl)bicyclo[2.2.1]heptan-1-yl)carbamate (Preparation Example (3-2)).

(Step 3)
A mixture of the compound of Preparation Example (3-2) (11.1 g), DME (110 ml) and aqueous ammonia (55 ml) was placed into a pressure reaction vessel and stirred at 100° C. for 16 hours. The reaction mixture was cooled to room temperature, and then water (150 ml) was added thereto, followed by stirring for 30 minutes. The resulting solid was collected by filtration and washed with water to obtain tert-butyl (4-(4-amino -5-bromo-7H-pyrrolo[2,3-d]pyrimidin-7-yl)bicyclo[2.2.1]heptane-1-yl)carbamate (Preparation Example (3-3)).

(Step 4)
A mixture of the compound of Preparation Example (3-3) (4.3 g). 3-quinolineboronic acid (2.1 g), chioro(2-dicyclohexylphosphino-2',4',6'-triisopropyl -1,1-biphenyl)[2-(2'-amino-1,1'-biphenyl)]palladium(II) (240 mg), sodium carbonate (2.2 g), THF (44 ml) and water (22 ml) was heated at reflux under a nitrogen atmosphere for 2 hours. The reaction mixture was cooled to room temperature, and then ethyl acetate (44 ml) and saturated aqueous sodium bicarbonate (10 ml) were added thereto, followed by stirring for overnight. After the organic layer was separated, the aqueous layer was extracted with ethyl acetate. The combined organic layers were dried over anhydrous magnesium sulfate and then filtered, and the filtrate was concentrated. The resulting residue was purified by silica gel column chromatography. The resulting solid was suspended in acetonitrile (25 ml), refluxed for 5 hours, and then cooled to 0° C. The solid was collected by filtration and washed with acetonitrile to obtain tert-butyl (4-(4-amino-5-(quinolin-3-yl)-7H-pyrrolo[2,3-d]pyrimidin-7-yl)bicyclo[2.2.1]heptan-1-yl)carbamate (Preparation Example (3-4)).

(Step 5)
To a solution of the compound of Preparation Example (3-4) (60 mg) in THF (2 ml), NBS (25 mg) was added at 0° C., followed by stirring for 15 minutes. The reaction mixture was diluted with 5% aqueous sodium sulfite and saturated aqueous sodium bicarbonate, and then extracted with ethyl acetate. The organic layer was washed with water and saturated brine, dried over anhydrous sodium tmlfate and then concentrated. The resulting residue was purified by silica gel column chromatography to obtain tert-butyl (4-(4-amino-6-bromo-5-(quinolin-3-yl)-7H-pyrrolo[2,3-d]pyrimidin -7-yl)bicyclo[2.2.1]heptan-1-yl)carbamate (Preparation Example (3-5)).

[Example 1]

N-(4-(4-Amino-6-ethynyl-5-(quinolin-3-yl)-7H-pyrrolo[2,3-d]pyrimidin-7-yl)bicyclo -[2.2.1]heptan-1-yl)benzamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (10 mg) in THF (1 ml), DIPEA (0.013 ml) was added and benzoyl chloride (0.006 ml) was then added. After stirring at room temperature for 30 minutes, the reaction mixture was concentrated. The resulting residue skins purified by silica gel column chromatography to obtain the above titled compound.

[Example 2]

N-(4-(4-Amino-6-ethynyl-5-(quinolin-3-yl)-7H-pyrrolo[2,3-d]pyrimidin-7-yl)bicyclo -[2.2.1]heptan-1-yl)pyrimidine-5-carboxamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (7 mg) in THF (1 ml ), DIPEA (0.013 ml) and pyrimidine-5-carboxylic acid (24 mg) were added, and HATU (10 mg) was then added. After stirring at room temperature for 30 minutes, the reaction mixture was concentrated. The resulting residue was purified by reversed -phase preparative HPLC (water/acetonitrile (0.1% -formic acid)) to obtain the above titled compound.

[Example 3]

N-(4-(4-Amino-6-ethynyl-5-(quinolin-3-yl)-7H-pyrrolo[2,3-d]pyrimidin-7-yl)bicyclo -[2.2.1]heptan-1-yl)pyridazine-4-carboxamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (7 mg) in THF (1 ml), DIPEA (0.013 ml) and pyridazine-4-carboxylic acid (24 mg) were added, and HATU (10 mg) was then added. After stirring at room temperature for 30 minutes, the reaction mixture was concentrated. The resulting residue was purified by silica gel column chromatography to obtain the above titled compound.

[Example 4]

2-((4-(4-Amino-6-ethynyl-5-(quinolin-3-yl)-7H-pyrrolo[2,3-d]pyrimidin-7-yl)bicyclo-[2.2.1]heptan-1-yl)amino)acetonitrile To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (10 mg) in a mixture of THF (1 ml) and acetonitrile (1 ml), DIPEA (0.013 ml) and bromoacetonitrile (0.003 ml) were added. After stirring at room temperature for 1 hour and then stirring at 50° C. for overnight, the reaction mixture was concentrated. The resulting residue was purified by silica gel column chromatography to obtain the above titled compound.

[Example 5]

4-(4-(4-Amino-6-ethynyl-5-(quinolin-3-yl)-7H-pyr-rolo[2,3-d]pyrimidin-7-yl)bicyclo-[2.2.1]heptan-1-yl)-1-methylpiperazin-2-one (Step 1) To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (20 mg) in dichloromethane (0.5 ml), triethylamine (0.011 ml) and methyl bromoacetate (0.005 ml) were added. After stirring at room temperature for overnight, the reaction mixture was diluted with water and extracted with ethyl acetate. The organic layer was dried over anhydrous magnesium sulfate and then filtered, and the filtrate was concentrated. The resulting residue was purified by basic silica gel column chromatography to obtain methyl (4-(4-amino-6-ethynyl-5-(quinolin-3-yl)-7H-pyrrolo[2,3-d]pyrimidin-7-yl)-bicyclo [2.2.1]heptan-1-yl)glycinate.

(Step 2) To a solution of methyl (4-(4-amino-6-ethynyl-5-(quinolin-3-yl)-7H-pyrrolo[2,3-d]pyrimidin-7-yl)-bicyclo[2.2.1]heptan-1-yl)glycinate obtained in Step 1 above in methanol (0.2 ml), tert-butyl methyl(2-oxoethyl)carbamate (0.01 ml) was added, and a solution of 0.5 M sodium cyanoborohydride an 0.25 M zinc chloride in methanol (0.3 ml) was then added under stirring conditions, followed stirring at 60° C. for overnight. A solution of 0.5 M sodium cyanobarohydride and 0.25 M zinc chloride in methanol (0.3 ml) was added again to the reaction mixture, was then further stirred for 1 day. After cooling to room temperature, trifluoroacetic acid (0.5 ml) was added and the reaction mixture was stirred for 3 days. The reaction mixture was concentrated, neutralized with saturated aqueous sodium bicarbonate, and then extracted with chloroform. The organic layer was dried over anhydrous magnesium sulfate and then concentrated. The resulting residue was purified by basic silica gel column chromatography to obtain the above titled compound.

[Example 6]

N-(4-(4-Amino-6-ethynyl-5-(quinoiln-3-yl)-7H-pyr-rolo[2,3-d]pyrimidin-7-yl)bicyclo-[2.2.2]octan-1-yl)-1-methyl-1H-pyrazole-5-carboxamide The same procedures as shown in Example 1 were repeated to obtain the above titled compound, except that 7-(4-aminobicyclo[2.2.1]heptan-1-yl)-6-ethynyl-5-(quinolin-3-yl)-7H-pyrrolo[2,3-d]pyrimidine-4-amine and benzoyl chloride used in Example 1 were replaced with 7-(1-amino-4-bicyclo[2.2.2]octanyl)-6-ethynyl-5-(quinolin-3-yl)pyrrolo [2,3-d]pyrimidine-4-amine and 1-methyl-1H-pyrazole-5-carbonyl chloride, respectively.

[Example 7]

4-(4-Amino-6-ethynyl-5-(quinoiln-3-yl)-7H-pyrrolo[2,3-d]pyrimidin-7-yl)bicyclo-[2.2.2]octan-1-ol The same procedures as shown in Preparation Example 1 (Steps 1 to 7) were repeated to obtain the above titled compound, except that tert-butyl (4-aminobicyclo[2.2.1] heptan-1-yl)carbamate used in Preparation Example 1 (Step 1) was replaced with 4-aminobicyclo[2.2.2]octan-1-ol.

[Example 8]

6-Ethynyl-7-(4-((pyridin-3-ylmethyl)amino)bicyclo [2.2.2]octan-1-yl)-5-(quinolin-3-yl)-7H-pyrrolo[2,3-d]pyrimidine-4-amine To a solution of 7-(4-aminobicyclo[2.2.2]octan-1-yl)-6-ethynyl-5-(quinolin-3-yl)-7H-pyrrolo[2,3-d]pyrimidine-4-amine obtained in Preparation Example 2 (10 mg) in THF (0.5 ml), potassium carbonate (17 mg), DIPEA (0.02 ml) and 3-(chloromethyl)-pyridine hydrochloride (20 mg) were added. The reaction mixture was stirred at 80° C. for 2 days. After cooling to room temperature, the mixture was purified by basic silica gel column chromatography to obtain the above tided compound.

[Example 9]

6-Ethynyl-7-(4-morpholinobicyclo[2.2.1]heptan-1-yl)-5-(quinolin-3-yl)-7H-pyrrolo[2,3-d]pyrimidine-4-amine A mixture of 7-(4-aminobicyclo[2.2.1]heptan-1-yl)-6-ethynyl-5-(quinolin-3-yl)-7H-pyrrolo[2,3-d]pyrimidine-4-amine (40 mg), DIPEA (0.11 ml), 1-bromo-2-(2-bromoethoxy)ethane (0.26 ml) and DMF (5 ml) was stirred at 80° C. for overnight. The reaction mixture was diluted with water and extracted with ethyl acetate. The organic layer was dried over anhydrous magnesium sulfate and then filtered, and the filtrate was concentrated. The resulting residue was purified by silica gel column chromatography and then concentrated. The residue was washed with ethyl acetate to obtain the above titled compound.

[Example 10]

4-(4-Amino-6-ethynyl-5-(quinoiln-3-yl)-7H-pyrrolo [2,3-d]pyrimidin-7-yl)bicyclo-[2.2.1]heptan-1-yl) methanol The same procedures as shown in Preparation Example 1 (Steps 1 to 7) were repeated to obtain the above titled compound, except that tert-butyl (4-aminobicyclo[2.2.1] heptan-1-yl)carbamate used in Preparation Example 1 (Step 1) was replaced with (4-aminobicyclo[2.2.1]heptan-1-yl) methanol.

[Example 11]

7-(4-(Dimethylamino)bicyclo[2.2.1]heptan-1-yl)-6-ethynyl-5-(quinolin-3-yl)-7H-pyrrolo[2,3-d]pyrimidine-4-amine To a solution of 7-(4-aminobicyclo[2.2.1]heptan-1-yl)-6-ethynyl-5-(quinolin-3-yl)-7H-pyrrolo[2,3-d]pyrimidine-4- amine obtained in Preparation Example 1 (10 mg) in a mixture of methanol (0.5 ml) and THF (0.5 ml), 37% aqueous formaldehyde (0.01 ml) was added, and a separately prepared methanol (0.1ml) solution of 0.5 M sodium cyanoborohydride and 0.25 M zinc chloride was then added. After stirring at room temperature for 30 minutes, the reaction mixture was concentrated. The resulting residue was purified by silica gel column chromatography to obtain the above titled compound.

[Example 12]

Ethyl (4-(4-amino-6-ethynyl-5-(quinolin-3-yl)-7H-pyrrolo[2,3-d]pyrimidin-7-yl) -bicyclo[2.2.1]heptan-1-yl)carbamate The same procedures as shown in Example 1 were repeated to obtain the above titled compound, except that benzoyl chloride used in Example 1 was replaced with ethyl chloroformate.

[Example 13]

N-((4-(4-Amino-6-ethynyl-5-(quinolin-3-yl)-7H-pyrrolo[2,3-d]pyrimidin-7-yl)bicyclo -[2.2.1]heptan-1-yl)methyl)-1-methyl-1H-pyrazole-5-carboxamide (Step 1) To a solution of (4-(4-amino-6-ethynyl-5-(quinolin-3-yl)-7H-pyrrolo[2,3-d]pyrimidin-7-yl)bicyclo[2.2.1]heptan-1-yl)methanol obtained in Example 10 (200 mg) in a mixture of dichloromethane (4.9 ml) and THF (4.9 ml), methanesulfonyl chloride (0.076 ml) and triethylamine (0.272 ml) were added under an ice bath. After stirring at room temperature for 1.5 hours, the reaction mixture was diluted with water and extracted with ethyl acetate. The organic layer was dried over anhydrous magnesium sulfate and then filtered, and the filtrate was concentrated. The resulting residue was purified by silica gel column chromatography and then concentrated. The residue was washed with ethyl acetate to obtain (4-(4-amino-6-ethynyl-5-(quinolin-3-yl)-7H -pyrrolo[2,3-d]pyrimidin-7-yl)bicyclo[2.2.1]heptan-1-yl)methyl methanesulfonate.

(Step 2) A mixture of (4-(4-amino-6-ethynyl-5-(quinolin-3-yl)-7H-pyrrolo[2,3-d]pyrimidin-7-yl)bicyclo[2.2.1]heptan-1-yl)methyl methanesulfonate (139 mg), sodium azide (55 mg) and DMSO (5.7 ml) was stirred at 80° C. or 24 hours and then stirred at 60° C. for overnight. The reaction mixture was diluted with water and filtered, and the residue was washed with water. To a solution of the resulting residue in THF (5.6 ml), triphenylphosphine (0.089 mg) was added, followed by stirring at 40° C. for overnight. After addition of water (0.10 ml), the reaction mixture was stirred at 40° C. for 6 hours and then concentrated. The resulting residue was purified by basic silica gel column chromatography to obtain 7-(4-(aminomethyl)bicyclo[2.2.1]heptan-1-yl)-6-ethynyl-5-(quinolin-3-yl)-7H-pyrrolo[2,3-d]pyrimidine-4-amine.

(Step 3) To a solution of 7-(4-(aminomethyl)bicyclo[2.2.1]heptan-1-yl)-6-ethynyl-5-(quinolin-3-yl)-7H-pyrrolo[2,3-d]pyrimidine-4-amine (5 mg), 1-methyl-1H-pyrazole-5-carboxylic acid (1.7 mg) and HATU (6.9 mg) in DMSO (0.5 ml), DIPEA (0.0064 ml) was added, followed by stirring at room temperature for 1 hour. The reaction mixture was purified by reversed-phase HPLC to obtain the above titled compound.

[Example 14]

N-((4-(4-Amino-6-ethynyl-5-(quinolin-3-yl)-7H-pyrrolo[2,3-d]pyrimidin-7-yl)bicyclo -[2.2.1]heptan-1-yl)methyl)-5-methylpyrazine-2-carboxamide The same procedures as shown in Example 13 (Step 3) were repeated to obtain the above titled compound, except that 1-methyl-1H-pyrazole-5-carboxylic acid used in Example 13 (Step 3) was replaced with 5-methylpyrazine-2-carboxylic acid.

[Example 15]

N-((4-(4-Amino-6-ethynyl-5-(quinolin-3-yl)-7H-pyrrolo[2,3-d]pyrimidin-7-yl)bicyclo -[2.2.1]heptan-1-yl)methyl)-5-chloropyrazine-2-carboxamide To a solution of 7-(4-(aminobicyclo[2.2.1]heptan-1-yl)-6-ethynyl-5-(quinolin-3-yl)-7H-pyrrolo[2,3-d]pyrimidine-4-amine obtained in Preparation Example 1 (5 mg) in DMF (1 ml), DIPEA (0.004 ml) and 5-chloropyrazine-2-carboxylic acid (5 mg) were added, and WSC (4 mg) and HOBT (3 mg) were then added. After stirring at 50° C. for 2 hours, the reaction mixture was purified by reversed-phase preparative HPLC (water/acetonitrile (0.1% formic acid)) to obtain the above titled compound.

[Example 16]

N-(4-(4-Amino-6-ethynyl-5-(quinolin-3-yl)-7H-pyrrolo[2,3-d]pyrimidin-7-yl)bicyclo -[2.2.1]heptan-1-yl)-[1.2.4]triazolo[1,5-a]pyrimidin-6-carboxamide To a solution of 7-(4-(aminobicyclo[2.2.1]heptan-1-yl)-6-ethynyl-5-(quinolin-3-yl)-7H-pyrrolo[2,3-d]pyrimidine-4-amine obtained in Preparation Example 1 (4 mg) in THF (1 ml) DMF (0.05 ml), DIPEA (0.006 ml) and [1,2,4]triazolol[1,5-a]pyridine-6-carboxylic acid (1.7 mg) were added, and HATU (6 mg) was then added. After stirring at room temperature for 2 hours, the reaction mixture was concentrated. The resulting residue was purified by silica gel column chromatography to obtain the above titled compound.

[Example 17]

N-(4-(4-Amino-6-ethynyl-5-(quinolin-3-yl)-7H-pyrrolo[2,3-d]pyrimidin-7-yl)bicyclo -[2.2.1]heptan-1-yl)-1-(2-methoxyethyl)-1H-pyrazole-5-carboxamide The sameprocedures as shown in Example 2 were repeated to obtain the above titled compound, except that THF and pyrimidine-5-carboxylic acid used in Example 2 were replaced with DMSO and 1-(2-methoxyethyl)-1H-pyrazole-5-carboxylic acid, respectively.

[Example 18]

N-(4-(4-Amino-6-ethynyl-5-(quinolin-3-yl)-7H-pyrrolo[2,3-d]pyrimidin-7-yl)bicyclo -[2.2.1]heptan-1-yl)-1,2,3-thiadiazole-5-carboxamide The same procedures as shown in Example 17 were repeated to obtain the above titled compound, except that 1-(2-methoxyethyl)-1H-pyrazole-5-carboxylic acid used in Example 17 was replaced with 1,2,3-thiadiazole-5-carboxylic acid.

[Example 19]

N-(4-(4-Amino-6-ethynyl-5-(quinolin-3-yl)-7H-pyrrolo[2,3-d]pyrimidin-7-yl)bicyclo -[2.2.1]heptan-1-yl)-1,2,4-triazine-3-carboxamide The same procedures as shown in Example 13 (Step 3) were repeated to obtain the above titled compound, except that 7-(4-(aminomethyl)bicyclo[2.2.1]heptan-1-yl)-6-ethynyl-5-(quinolin-3-yl)-7H-pyrrolo[2,3-d]pyrimidine-4-amine and 5-methylpyrazine -2-carboxylic acid used in Example 13 (Step 3) were replaced with 7-(4-(aminobicyclo -[2.2.1]heptan-1-yl)-6-ethynyl-5-(quinolin-3-yl)-7H-pyrrolo[2,3-d]pyrimidine-4-amine and sodium 1,2,4-triazine-3-carboxylate, respectively.

[Example 20]

N-(4-(4-Amino-6-ethynyl-5-(quinolin-3-yl)-7H-pyrrolo[2,3-d]pyrimidin-7-yl)bicyclo -[2.2.1]heptan-1-yl)-1-cyclopropyl-1H-pyrazole-5-carboxamide The same procedures as shown in Example 17 were repealed to obtain the above tided compound, except that 1-(2-methoxyethyl)-1H-pyrazole-5-carboxylic acid used in Example 17 was replaced with 1-cyclopropyl-1H-pyrazole5-carboxylic acid.

[Example 21]

N-(4-(4-Amino-6-ethynyl-5-(quinolin-3-yl)-7H-pyrrolo[2,3-d]pyrimidin-7-yl)bicyclo -[2.2.1]heptan-1-yl)-1H-pyrazole-1-carboxamide To a solution of 7-(4-(aminobicyclo[2.2.1]heptan-1-yl)-6-ethynyl-5-(quinolin-3-yl)-7H-pyrrolo[2,3-d]pyrimidine-4-amine obtained in Preparation Example 1 (9.5 mg) in DMF (0.4 ml), carbonyldiimidazole (8 mg) was added, followed by stirring at room tempera fore for 1 hour. After addition of pyrazole (5 mg) and stirring for overnight at room temperature, the reaction mixture was diluted with water and extracted with ethyl acetate. The organic layer was dried over anhydrous magnesium sulfate and then filtered, and the filtrate was concentrated. The resulting residue was purified by silica gel column chromatography to obtain the above titled compound.

[Example 22]

N-(4-(4-Amino-6-ethynyl-5-(quinolin-3-yl)-7H-pyrrolo[2,3-d]pyrimidin-7-yl)bicyclo -[2.2.1]heptan-1-yl)-1-methyl-1H-1,2,3-triazole-5-carboxamide The same procedures as shown in Example 17 were repeated to obtain the above titled compound, except that 1-(2-methoxyethyl)-1H-pyrazole-5-carboxylic acid used in Example 17 was replaced with 1-methyl-1H-1,2,3-triazole5-carboxylic acid.

[Example 23]

N-(4-(4-Amino-6-ethynyl-5-(quinolin-3-yl)-7H-pyrrolo[2,3-d]pyrimidin-7-yl)bicyclo -[2.2.1]heptan-1-yl)-1-methyl-1H-imidazole-2-carboxamide The same procedures as shown in Example 17 were repeated to obtain the above titled compound, except that 1-(2-methoxyethyl)-1H-pyrazole-5-carboxylic acid used in Example 17 was replaced with 1-methyl-1H-imidazole-2-carboxylic acid.

[Example 24]

N-(4-(4-Amino-6-ethynyl-5-(quinolin-3-yl)-7H-pyrrolo[2,3-d]pyrimidin-7-yl)bicyclo -[2.2.1]heptan-1-yl)-1-methyl-1H-pyrazole-5-carboxamide The same procedures as shown in Example 1 were repeated to obtain the above titled compound, except that benzoyl chloride used in Example 1 was replaced with 1-methyl-1H-pyrazole-5-carbonyl chloride.

[Example 25]

N-(4-(4-Amino-6-ethynyl-5-(quinolin-3-yl)-7H-pyrrolo[2,3-d]pyrimidin-7-yl)bicyclo -[2.2.1]heptan-1-yl)-1-methyl-6-oxo-1,6-dihydropyrimidine-5-carboxamide The same procedures as shown in Example 17 were repeated to obtain the above titled compound, except that 1-(2-methoxyethyl)-1H-pyrazole-5-carboxylic acid used in Example 17 was replaced with 1-methyl-6-oxo-1,6-dihydropyrimidine-5-carboxylic acid.

[Example 26]

N-(4-(4-Amino-6-ethynyl-5-(quinolin-3-yl)-7H-pyrrolo[2,3-d]pyrimidin-7-yl)bicyclo -[2.2.1]heptan-1-yl)-1-phenyl-1H-pyrazole-5-carboxamide The same procedures as shown in Example 17 were repeated to obtain the above titled compound, except that 1-(2-methoxyethyl)-1H-pyrazole-5-carboxylic acid used in Example 17 was replaced with 1-phenyl-1H-pyrazole-5-carboxylic acid.

[Example 27]

N-(4-(4-Amino-6-ethynyl-5-(quinolin-3-yl)-7H-pyrrolo[2,3-d]pyrimidin-7-yl)bicyclo -[2.2.1]heptan-1-yl)-2,2-difluoroacetamide To a solution of 7-(4-(aminobicyclo[2.2.1]heptan-1-yl)-6-ethynyl-5-(quinolin-3-yl)-7H-pyrrolo[2,3-d]pyrimidine-4-amine (25 mg) in dichloromethane (2 ml), a solution of 2,2-difluoroacetic anhydride (0.0079 ml) in dichloromethane (0.5 ml) was added under an ice bath, followed by stirring for 1 hour under an ice bath. The reaction mixture was purified by silica gel column chromatography to obtain the above titled compound.

[Example 28]

N-(4-(4-Amino-6-ethynyl-5-(quinolin-3-yl)-7H-pyrrolo[2,3-d]pyrimidin-7-yl)bicyclo -[2.2.1]heptan-1-yl)-2-methoxyacetamide The same procedures as shown in Example 13 (Step 3) were repeated to obtain the above titled compound, except that 7-(4-(aminomethyl)bicyclo[2.2.1]heptan-1-yl)-6-ethynyl-5-(quinolin-3-yl)-7H-pyrrolo[2,3-d]pyrimidine-4-amine and 5-methylpyrazine -2-carboxylic acid used in Example 13 (Step 3) were replaced with 7-(4-aminobicyclo -[2.2.1] heptane-1-yl)6-ethynyl-5-(quinolin-3-yl)-7H-pyrrolo[2,3-d] pyrimidine-4-amine and 2-methoxyacetic acid, respectively.

[Example 29]

N-(4-(4-Amino-6-ethynyl-5-(quinolin-3-yl)-7H-pyrrolo[2,3-d]pyrimidin-7-yl)bicyclo -[2.2.1]heptan-1-yl)-3-(fluoromethyl)-1-methyl-1H-pyrazole-5-carboxamide (Step 1) To a suspension of potassium tert-butoxide (6.1 g) in THF (50 ml), a mixed solution of 2-acetylfuran (3.0 g) and diethyl oxalate (8.0 g) in 1,2-dimethyoxyethane (50 ml) was added. After stirring at room temperature for 2 hours, the solvent was distilled off under reduced pressure, and 1 M hydrochloric acid (20 ml) was then added. After extraction with ethyl acetate, the organic layer was washed with water and then concentrated to obtain ethyl 4-(furan-2-yl)-2,4-dioxobutanoate.

(Step 2) To a solution of ethyl 4-(furan-2-yl)-2,4-dioxobutanoate obtained in Step 1 (2.4 g) in 1,1,1,3,3,3-hexafluoroisopropanol (25 ml), methylhydrazine (1.1 ml) was added, followed by stirring at room temperature. After completion of the reaction, the reaction mixture was concentrated, and the resulting residue was purified by silica gel column chromatography to obtain ethyl 5-(furan-2-yl)-1-methyl-1H-pyrazole-3-carboxylate.

(Step 3) To a suspension of lithium aluminum hydride (0.5 g) in THF (10 ml), ethyl 5-(furan-2-yl)-1-methyl-1H-pyrazole-3-carboxylate (1.5 g) was added under an ice bath. The reaction mixture was stirred at 60° C. After completion of the reaction, the reaction mixture was cooled to room temperature, and then saturated aqueous sodium sulfate (5 ml) was added thereto. The residue was filtered, and the filtrate was concentrated and then purified by silica gel column chromatography to obtain (5-(furan -2-yl)-1-methyl-1H-pyrazol-3-yl)methanol.

(Step 4) To a solution of (5-(furan-2-yl)-1-methyl-1H-pyrazol-3-yl)methanol (0.16 g) in dichloromethane (2 ml), bis(2-methoxyethyl)amino sulfate fluoride (0.34 ml) was added under an ice bath. After stirring at room temperature for 1 hour saturated aqueous sodium bicarbonate (1 ml) was added and the reaction mixture was extracted with ethyl acetate, and then the organic layer was washed with water. After the organic layer was concentrated, the resulting residue was purified by silica gel column chromatography to obtain 3-(fluoromethyl)-5-(furan-2-yl)-1-methyl-1H-pyrazole.

(Step 5) To a solution of 3-(fluoromethyl)-5-(furan-2-yl)-1-methyl-1H-pyrazole (62 mg) in a mixture of acetonitrile (2 ml), carbon tetrachloride (2 ml) and water (3 ml), sodium periodate (0.73 g) and ruthenium(III) chloride hydrate (5 mg) were added, followed by stirring at room temperature. After completion of the reaction, the residue was filtered and the filtrate was concentrated to obtain 5-(fluoromethyl)-2-methyl -pyrazole-3-carboxylic acid.

(Step 6) To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (5 mg) in THF (2 ml), DMF (0.02 ml), DIPEA (0.007 ml) and 5-(fluoromethyl)-2-methyl -pyrazole-3-carboxylic acid 2.0 mg) were added, and HATU (7 mg) was then added. After stirring at room temperature for 2 hours, the reaction mixture was concentrated. The resulting residue was purified by silica gel column chromatography to obtain the above titled compound.

[Example 30]

N-(4-(4-Amino-6-ethynyl-5-(quinolin-3-yl)-7H-pyrrolo[2,3-d]pyrimidin-7-yl)bicyclo -[2.2.1]heptan-1-yl)-4-(methylsulfonyl)picolinamide (Step 1) A mixture of methyl 4-chloropicolinate (343 mg), sodium methanesulfinate (204 mg), copper(I) chloride (19.8 mg), quinoline (26 mg) and NMP (3 ml) was stirred at 140° C. for 5.5 hours under microwave irradiation. After the reaction mixture was diluted with water and ethyl acetate, insoluble materials were filtered off and the filtrate was extracted with ethyl acetate. The organic layer was concentrated, and the residue was purified by silica gel column chromatogyaphy to obtain methyl 4-(methylsulfonyl)picolinate.

(Step 2) To a solution of methyl 4-(methylsulfonyl)picolinate (113 mg) in THF (1.3 ml), 0.2 N aqueous sodium hydroxide (2.6 ml) was added, followed by stirring at room temperature for 30 minutes. The reaction mixture was concentrated to obtain sodium 4-(methylsulfonyl)picolinate.

(Step 3) The same procedures as shown in a Example 13 (Step 3) were repeated to obtain the above titled compound, except that 7-(4-(aminomethyl)bicyclolo[2.2.1]heptan-1-yl)-6-ethynyl-5-(quinolin-3-yl)-7H-pyrrolo[2,3-d]pyrimidine-4-amine and 5-methylpyrazine -2-carboxylic acid used in Example 13 (Step 3) were replaced with 7-(4-aminobicyclo -[2.2.1]heptan-1-yl)-6-ethynyl-5-(quinolin-3-yl)-7H-pyrrolo[2,3-d]pyrimidine-4-amine and sodium 4-(methylsulfonyl)picolinate, respectively.

[Example 31]

N-(4-(4-Amino-6-ethynyl-5-(quinolin-3-yl)-7H-pyrrolo[2,3-d]pyrimidin-7-yl)bicyclo -[2.2.1]heptan-1-yl)-4-methoxynicotinamide The same procedures as shown in Example 29 (Step 6) were repeated to obtain the above titled compound, except that 5-(fluoromethyl)-2-methyl-pyrazole-3-carboxylic acid used in Example 29 was replaced with 4-methoxynicotinic acid.

[Example 32]

N-(4-(4-Amino-6-ethynyl-5-(quinolin-3-yl)-7H-pyrrolo[2,3-d]pyrimidin-7-yl)bicyclo -[2.2.1]heptan-1-yl)-5-(dimethylamino)pyrazine-2-carboxamide The same procedures as shown in Example 17 were repeated to obtain the above titled compound, except that 1-(2-methoxyethyl)-1H-pyrazole-5-carboxylic acid used in Example 17 was replaced with 5-(dimethylamino)pyrazine-2-carboxylic acid.

[Example 33]

N-(4-(4-Amino-6-(propyn-1-yl)-5-(quinolin-3-yl)-7H-pyrrolo[2,3-d]pyrimidin-7-yl) -bicyclo[2.2.1]heptan-1-yl)-1-methyl-1H-pyrazole-5-carboxamide (Step 1) To a solution of tert-butyl (4-(4-amino-6-bromo-5-(quinolin-3-yl)-7H -pyrrolo[2,3-d]pyrimidin-7-yl)bicyclo[2.2.1]heptan-1-yl)carbamate obtained in Preparation Example 3 (40 mg) in DMSO (2 ml), bis(triphenylphosphine)palladium(II) dichloride (10 mg), copper(I) iodide (6 mg), DIPEA (0.02 ml) and propyne in DMF (1 M, 0.15 ml) were added, followed by stirring at 80° C. for overnight under a nitrogen atmosphere. The reaction mixture was purified by reversed-phase preparative HPLC (water/acetonitrile (0.1% formic acid)) to obtain tert-butyl (4-(4-amino-6-(propyn-1-yl) -5-(quinolin-3-yl)-7H-pyrrolo[2,3-d]pyrimidin-7-yl)bicyclo[2.2.1]heptan-1-yl)carbamate.

(Step 2) The same procedures as shown in Preparation Example 1 (Step 8) were repeated to obtain 7-(4-aminobicyclo[2.2.1]heptan-1-yl)-6-(propyn-1-yl)-5-(quinolin-3-yl)-7H-pyrrolo[2,3-d]pyrimidine-4-amine, except that tert-butyl (4-(4-amino-6-ethynyl -5-(quinolin-3-yl)-7H-pyrrolo[2,3-d]pyrimidin-7-yl)bicyclo[2.2.1]heptan-1-yl)carbamate used in Preparation Example 1 (Step 8) was replaced with tert-butyl (4-(4-amino-6-(propyn-1-yl)-5-(quinolin-3-yl)-7H-pyrrolo[2,3-d]pyrimidin-7-yl)bicyclo[2.2.1]heptan -1-yl)carbamate obtained in Step 1 above.

(Step 3) The same procedures as shown in Example 15 were repeated to obtain the above titled compound, except that 7-(4-aminobicyclo[2.2.1]heptan-1-yl)-6-ethynyl-5-(quinolin-3-yl)-7H-pyrrolo[2,3-d]pyrimidine-4-amine and 5-chloropyrazine-2-carboxylic acid used in Example 15 were replaced with 7-(4aminobicyclo[2.2.1]-heptan-1-yl)-6-(propyn-1-yl)-5-(quinolin-3-yl)-7H-pyrrolo[2,3-d]pyrimidine-4-amine obtained in Step 2 above and 1-methyl-1H-pyrazole-5-carboxylic acid, respectively.

[Example 34]

N-(4-(4-Amino-6-ethynyl-5-(quinolin-3-yl)-7H-pyrrolo[2,3-d]pyrimidin-7-yl)-bicyclo -[2.2.1]heptan-1-yl)-5-cyanonicotinamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (5 mg) in DMF (1 ml), DIPEA (0.004 ml) and 5-cyanopyridine-3-carboxylic acid (5 mg) were added, and WSC (4 mg) and HOBT (3 mg) were then added. After stirring at 50° C. for 2 hours, the reaction mixture was purified by reversed-phase preparative HPLC (water/acetonitrile (0.1% formic acid)) to obtain the above titled compound.

[Example 35]

N-(4-(4-Amino-6-ethynyl-5-(quinolin-3-yl)-7H-pyrrolo[2,3-d]pyrimidin-7-yl)-bicyclo -[2.2.1]heptan-1-yl)-5-fluoronicotinamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (5 mg) in DMSO (1 ml), DIPEA (0.004 ml) and 5-fluoropyridine-3-carboxylic acid (5 mg) were added, and WSC (4 mg) and HOBT (3 mg) were then added. After stirring at 50° C. for 1 hour, the reaction mixture was purified by reversed-phase preparative HPLC (water/acetonitrile (0.1% formic acid)) to obtain the above titled compound.

[Example 36]

N-(4-(4-Amino-6-ethynyl-5-(quinolin-3-yl)-7H-pyrrolo[2,3-d]pyrimidin-7-yl)-bicyclo -[2.2.1]heptan-1-yl)-5-methyl-1,2,4-oxadiazole-3-carboxamide The same procedures as shown in Example 17 were repeated to obtain the above titled compound, except that 1-(2-methoxyethyl)-1H-pyrazole-5 -carboxylic acid used in Example 17 was replaced with lithium 5-methyl-1,2,4-oxadiazole-3-carboxylate.

[Example 37]

N-(4-(4-Amino-6-ethynyl-5-(quinolin-3-yl)-7H-pyrrolo[2,3-d]pyrimidin-7-yl)-bicyclo -[2.2.1]heptan-1-yl)-5-methylpyrazine-2-carboxamide The same procedures as shown in Example 29 (Step 6) were repeated to obtain the above titled compound, except that 5-(fluoromethyl)-2-methyl-pyrazole-3-carboxylic acid used in Example 29 was replaced with 5-methylpyrazine-2-carboxylic acid.

[Example 38]

N-(4-(4-Amino-6-ethynyl-5-(quinolin-3-yl)-7H-pyrrolo[2,3-d]pyrimidin-7-yl)-bicyclo -[2.2.1]heptan-1-yl)-6-(fluoromethoxy)pyrazine-2-carboxamide (Step 1) A mixture of 6-bromopyrazin-2-ol (221 mg), fluoromethyl 4-methylbenzenesulfonate (200 mg), cesium carbonate (383 mg) and DMPU (1.6 ml) was stirred at 70° C. for 4 hours. The reaction mixture was cooled to room temperature, and then diluted with water and extracted with ethyl acetate. The organic layer was dried over anhydrous magnesium sulfate and then. filtered, and the filtrate vas concentrated. The resulting residue was purified by silica gel column chromatography to obtain 2-bromo-6-(fluoromethoxy)pyrazine.

(Step 2) A solution of 2-bromo-6-(fluoromethoxy)pyrazine (179 mg) in a mixture of DMA (1.5 ml) and methanol (3 ml) was placed into a pressure tube, and then sodium acetate (124 mg) and [1,1'-bis(diphenylphosphino)ferrocene]palladium(II) dichloride dichloromethane adduct (28 mg) were added thereto, followed by stirring at 50° C. for 18 hours under a carbon monoxide atmosphere. The reaction mixture was cooled to room temperature, and then diluted with water and ethyl acetate. Insoluble materials were filtered off and the filtrate was extracted with ethyl acetate. The organic layer was washed with aqueous sodium chloride, dried over anhydrous magnesium sulfate and then filtered, and the filtrate was concentrated. The resulting residue was purified by silica gel column chromatography to obtain methyl 6-(fluoromethoxy)pyrazine-2-carboxylate.

(Step 3) The same procedures as shown in Example 30 (Step 2) were repeated to obtain sodium 6-(fluoromethoxy)pyrazine-2-carboxylate, except that methyl 4-(methyl sulfonyl)picolinate used in Example 30 (Step 2) was replaced with methyl 6-(fluoromethoxy)pyrazine-2-carboxylate.

(Step 4) The same procedures as shown in Example 13 (Step 3) were repeated to obtain the above titled compound, except that 7-(4-aminomethyl)bicyclo[2.2.1]heptan-1-yl)-6- ethynyl-5-(quinolin-3-yl)-7H-pyrrolo[2,3-d]pyrimidine-4-amine and 5-methylpyrazine -2-carboxylic acid used in Example 13 (Step 3) were replaced with 7-(4-amino -bicyclo [2.2.1]heptan-1-yl)-6-ethynyl-5-(quinolin-3-yl)-7H-pyrrolo [2,3-d]pyrimidine-4-amine and sodium 6-(fluoromethoxy) pyrazine-2-carboxylate, respectively.

[Example 39]

N-(4-(4-Amino-6-ethynyl-5-(quinolin-3-yl)-7H-pyrrolo[2,3-d]pyrimidin-7-yl)-bicyclo -[2.2.1]heptan-1-yl)acetamide The same procedures as shown in Example 1 were repeated to obtain the above titled compound, except that benzoyl chloride used in Example 1 was replaced with acetic anhydride.

[Example 40]

7-(4-((Dimethylamino)methyl)bicyclo[2.2.1]heptan-1-yl)-6-ethynyl-5-(quinolin-3-yl) -7H-pyrrolo[2,3-d]pyrimidine-4-amine (Step 1) A mixture or (4-(4-amino-6-ethynyl-5-(quinolin-3-yl)-7H-pyrrolo[2,3-d]pyrimidin-7-yl)-bicyclo-[2.2.1]heptan-1-yl)methanol obtained in Example 10 (30 mg), Dess-Martin periodinane (47 mg) and dichloromethane (2.9 ml) was stirred at room temperature for 10 minutes. The reaction mixture was diluted with aqueous sodium thiosulfate and saturated aqueous sodium bicarbonate, and then extracted with ethyl acetate. The organic layer was washed with aqueous sodium chloride, dried over anhydrous magnesium sulfate and then filtered, and the filtrate was concentrated. The resulting residue was purified by silica gel column chromatography to obtain 4-(4-amino-6-ethynyl-5-(quinolin-3-yl)-7H-pyrrolo[2,3-d]pyrimidin-7-yl)bicyclo[2.2.1]-heptane-1-carbaldehyde.
(Step 2) To a solution of 4-(4-amino-6-ethynyl-5-(quinolin-3-yl)-7H-pyrrolo[2,3-d]pyrimidin-7-yl)bicyclo[2.2.1] heptane-1-carbaldehyde (5 mg) in methanol (0.5 ml), 2 M dimethylamine in THF (0.012 ml) was added. The reaction mixture was stirred at room temperature for 30 minutes, and a solution of 0.5 M sodium cyanoborohydride and 0.25 M zinc chloride in methanol (0.07 ml) was then added thereto. After the reaction mixture was stirred at 40° C. for 30 minutes, the reaction mixture was purified by basic silica gel column chromatography and then concentrated. The resulting residue was purified by reversed-phase HPLC to obtain the above titled compound.

[Example 41]

N-4-(4-Amino-6-ethynyl-5-(quinolin-3-yl)-7H-pyrrolo[2,3-d]pyrimidin-7-yl)bicyclo -[2.2.1]heptane-1-yl)furan-2-carboxamide The same procedures as shown in Example 1 were repeated to obtain the above titled compound, except that benzoyl chloride used in Example 1 was replaced with 2-furancarbonyl chloride.

[Example 42]

N-4-(4-Amino-6-ethynyl-5-(quinolin-3-yl)-7H-pyrrolo[2,3-d]pyrimidin-7-yl)bicyclo -[2.2.1]heptane-1-yl)imidazo[1,2-a]pyrazine-8-carboxamide The same procedures as shown in Example 1 were repeated to obtain above titled compound, except that 1-(2-methoxyethyl)-1H-pyrazole-5-carboxylic acid used in Example 17 was replaced with imidazo[1,2-a]pyrazine-8-carboxylic acid.

[Example 43]

N-4-(4-Amino-6-ethynyl-5-(quinolin-3-yl)-7H-pyrrolo[2,3-d]pyrimidin-7-yl)bicyclo -[2.2.1]heptane-1-yl)isonicotinamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (9 mg) in THF (0.5 ml), DIPEA (0.008 ml) and isomcotinic acid (42 mg) were added, and HATU (13 mg) was then added. After stirring at room temperature for 30 minutes, dichloromethane (0.5 ml) was added, and the reaction mixture was stirred for overnight and then concentrated. The resulting residue was purified by reversed-phase prepara HPLC (water/acetonitrile (0.1% formic acid)) to obtain the above titled compound.

[Example 44]

N-4-(4-Amino-6-ethynyl-5-(quinolin-3-yl)-7H-pyrrolo[2,3-d]pyrimidin-7-yl)bicyclo -[2.2.1]heptane-1-yl)isoxazole-5-carboxamide The same procedures as shown in Example 1 were repeated to obtain the above titled compound, except that benzoyl chloride used in Example 1 vaas replaced with isoxazole-5-carbonyl chloride.

[Example 45]

N-4-(4-Amino-6-ethynyl-5-(quinolin-3-yl)-7H-pyrrolo[2,3-d]pyrimidin-7-yl)bicyclo -[2.2.1]heptane-1-yl)nicotinamide The same procedures as shown in Example 43 were repeated to obtain the above titled compound, except that isonicotinic acid used in Example 43 was replaced with nicotinic acid.

[Example 46]

N-4-(4-Amino-6-ethynyl-5-(quinolin-3-yl)-7H-pyrrolo[2,3-d]pyrimidin-7-yl)bicyclo -[2.2.1]heptane-1-yl)oxazole-2-carboxamide The same procedures as shown in Example 17 were repeated to obtain the ahoy titled compound, except that 1-(2-methoxyethyl)-1H-pyrazole-5-carboxylic acid used in Example 17 was replaced with oxazole-2-carboxylic acid.

[Example 47]

N-4-(4-Amino-6-ethynyl-5-(quinolin-3-yl)-7H-pyrrolo[2,3-d]pyrimidin-7-yl)bicyclo -[2.2.1]heptane-1-yl)oxazole-5-carboxamide The same procedures as shown in Example 17 were repeated to obtain the above tided compound, except that 1-(2-methoxyethyl)-1H-pyrazole-5-carboxylic acid used in Example 17 was replaced with oxazole-5-carboxylic acid.

[Example 48]

N-4-(4-Amino-6-ethynyl-5-(quinolin-3-yl)-7H-pyrrolo[2,3-d]pyrimidin-7-yl)bicyclo -[2.2.1]heptane-1-yl)pyrazine-2-carboxamide The same procedures as shown in Example 2 were repeated to obtain th ove titled compound, except that pyrimidine-5-carboxylic acid used in Example 2 was replaced with 2-pyrazinecarboxylic acid.

[Example 49]

N-4-(4-Amino-6-ethynyl-5-(quinolin-3-yl)-7H-pyrrolo[2,3-d]pyrimidin-7-yl)bicyclo -[2.2.1]heptane-1-yl)pyridazine-3-carboxamide The same procedures as shown in Example 17 repeated to obtain the above titled compound, except that 1-(2-methoxyethyl)-1H-pyrazole-5-carboxylic acid used in Example 17 was replaced with pyridazine-3-carboxylic acid.

[Example 50]

1-4-(4-Amino-6-ethynyl-5-(quinolin-3-yl)-7H-pyrrolo[2,3-d]pyrimidin-7-yl)bicyclo -[2.2.1]heptane-1-yl)-3-ethylurea The same procedures as shown in Example 1 were repeated to obtain the above titled compound, except that benzoyl chloride used in Example 1 was replaced with ethyl isocyanate.

[Example 51]

N-4-(4-Amino-6-ethynyl-5-(quinolin-3-yl)-7H-pyrrolo[2,3-d]pyrimidin-7-yl)bicyclo -[2.2.1]heptane-1-yl)pyrimidine-2-carboxamide A solution of 7-(4-aminobicyclo[2.2.1]heptan-1-yl)-6-ethynyl-5-(quinolin-3-yl)-7H-pyrrolo[2,3-d]pyrimidine-4-amine (10 mg), pyrimidine-2-carboxylic acid (2.5 mg), HATU (14.5 mg) and DIPEA (0.013 ml) in a mixture of THF (1 ml) and DMF (0.01 ml) was stirred at room temperature for 3 hours. The reaction mixture was purified by silica gel column chromatography to obtain the above titled compound.

[Example 52]

1-4-(4-Amino-6-ethynyl-5-(quinolin-3-yl)-7H-pyrrolo[2,3-d]pyrimidin-7-yl)bicyclo -[2.2.1]heptane-1-yl)-3-ethylthiourea The same procedures as shown in Example 1 were repeated to obtain the above titled compound, except that bei oyl chloride used in Example 1 was replaced with ethyl isothiocyanate.

[Example 53]

N-4-(4-Amino-6-ethynyl-5-(quinolin-3-yl)-7H-pyrrolo[2,3-d]pyrimidin-7-yl)bicyclo -[2.2.1]heptane-1-yl)thiazole-2-carboxamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (5 mg) in DMF (1 ml), DIPEA (0.004 ml) and thiazole-2-carboxylic acid (5 mg) were added, and WSC (4 mg) and HOBT (3 mg) were then added. After stirring at 50° C. for 1 hour, the reaction mixture was purified by reversed-phase preparative HPLC (water/acetonitrile (0.1% formic acid)) to obtain the above titled compound.

[Example 54]

6-Ethynyl-7-(4-(((2-fluoroethyl)amino)methyl)bicyclo[2.2.1]heptan-1-yl)-5-(quinolin-3-yl)-7H-pyrrolo [2,3-d]pyrimidine-4-amine A solution of 4-(4-amino-6-ethynyl-5-(quinolin-3-yl)-7H-pyrrolo[2,3-d]-pyrimidine-7-yl)bicyclo[2.2.1]heptan-1-carbaldehyde obtained in Example 40 (Step 1) (7.7 mg), 2-fluoroethylamine hydrochloride (3.8 mg) and DIPEA (0.066 ml) in a mixture of methanol (0.5 ml) and THF (0.5 ml) was stirred at room temperature for 30 minutes. To the reaction mixture, a solution of 0.5 M sodium cyanoborohydride and 0.25 M zinc chloride in methanol (0.1 ml) was added. After the reaction mixture was stirred at room temperature for 30 minutes, the reaction mixture was purified by basic silica gel column chromatography and then concentrated. The resulting residue was purified by reversed-phase HPLC to obtain the above titled compound.

[Example 55]

N-4-(4-Amino-6-ethynyl-5-(quinolin-3-yl)-7H-pyrrolo[2,3-d]pyrimidin-7-yl)bicyclo -[2.2.2]octan-1-yl)-2-(dimethylamino)acetamide To a solution of 7-(4-aminobicyclo[2.2.2]octan-1-yl)-6-ethynyl-5-(quinolin-3-yl)-7H-pyrrolo[2,3-d]pyrimidine-4-amine obtained in Preparation Example 2 (5 mg) in DMF (1 ml), DIPEA (0.004 ml) and N,N-dimethylglycine (0.003 ml) were added, and WSC (4 mg) and HOBT (3 mg) were then added. After stirring at 60° C. for 2 hours, the reaction mixture was purified by reversed-phase preparative HPLC (water/acetonitrile (0.1% formic acid)) to obtain the above titled compound.

[Example 56]

N-4-(4-Amino-6-ethynyl-5-(quinolin-3-yl)-7H-pyrrolo[2,3-d]pyrimidin-7-yl)bicyclo -[2.2.2]octan-1-yl)-6-methyl-2,6-diazaspiro[3.3]heptane-2-carbothioamide To a solution of 7-(4-aminobicyclo[2.2.2]octan-1-yl)-6-ethynyl-5-(quinolin-3-yl)-7H-pyrrolo[2,3-d]pyrimidine-4-amine obtained in Preparation Example 2 (10 mg) in DMF (1 ml), DIPEA (0.013 ml) and 1,1'-thiocarbonyldiimidazole (9 mg) were added, followed by stirring at room temperature for 30 minutes. After 2-methyl-2,6-diazaspiro[3.3]heptane dihydrochlaride (9 mg) was further added, the reaction mixture was stirred at 60° C. for 4 hours. The reaction mixture was purified by reversed-phase preparative HPLC (water/acetonitrile (0.1% formic acid)) to obtain the above titled compound.

[Example 57]

N-[4-(4-Amino-6-ethynyl-5-quinolin-3-yl)-7H-pyrrolo[2,3-d]pyrimidin-7-yl)-1-bicyclo -[2.2.1]heptan-1-yl]-N,5-dimethylpyrazine-2-carboxamide (Step 1) A mixture of N-(4-(4-amino-6-ethynyl-5-(quinolin-3-yl)-7H-pyrrolo[2,3-d]pyrimidin-7-yl)bicyclo[2.2.1]

heptan-1-yl)-5-methylpyrazine-2-carboxamide obtained in Example 37 (100 mg) and N,N-dimethylformamide dimethyl acetal (1 ml) was stirred at 60° C. for 3 hours. The reaction mixture was cooled to room temperature, and then diisopropyl ether (1 ml) was added thereto, followed by stirring at room temperature for 1 hour. The resulting solid was collected by filtration and washed with diisopropyl ether to obtain crude (E)-N-(4-(4-(((dimethylamino)methylene) amino)-6-ethynyl-5-(quinolin-3-yl)-7H-pyrrolo[2,3-d]pyrimidin-7-yl)bicyclo[2.2.1]heptan-1-yl)-5-methylpyrazine-2-carboxamide.

(Step 2) To a mixture of crude (E)-N-(4-(4-(((dimethylamino)methylene)amino)-6-ethynyl-5-(quinolin-3-yl)-7H-pyrrolo[2,3-d]pyrimidin-7-yl)bicyclo[2.2.1]heptan-1-yl)-5-methylpyrazine-2-carboxamide obtained in Step 1 above (10 mg) and THF (1 ml), iodomethane (0.02 ml) and an excessive amount of sodium hydride were added, followed by stirring at room temperature for 15 minutes. DMF (0.2 ml) was added to the reaction mixture, which was then further stirred for 30 minutes. The reaction mixture was concentrated and purified by reversed-phase preparative HPLC (water/acetonitrile (0.1% formic acid)) to obtain the above titled compound.

[Example 58]

N-[4-(4-Amino-6-ethynyl-5-quinolin-3-ylpyrrolo[2,3-d]pyrimidin-7-yl)-1-bicyclo -[2.2.1]heptan-1-yl]-N-methyloxazole-2-carboxamide (Step 1) The same procedures as shown in Example 57 (Step 1) were repeated to obtain crude (E)-N-(4-(4-(((dimethylamino)methylene)amino)-6-ethynyl-5-(quinolin-3-yl)-7H -pyrrolo[2,3-d]pyrimidin-7-yl)bicyclo[2.2.1]heptan-1-yl)oxazole-2-carboxamide, except that N-(4-(4-amino-6-ethynyl-5-(quinolin-3-yl)-7H-pyrrolo[2,3-d]pyrimidin-7-yl) -bicyclo[2.2.1]heptan-1-yl)-5-methylpyrazine-2-carboxamide used in Example 57 was replaced with N-(4-(4-amino-6-ethynyl-5-(quinolin-3-yl)-7H-pyrrolo[2,3-d]pyrimidin -7-yl)bicyclo[2.2.1]heptan-1-yl)oxazole-2-carboxamide obtained in Example 46.

(Step 2) To a mixture of crude (E)-N-(4-(4-(((dimethylamino)methylene)amino)-6-ethynyl-5-(quinolin-3-yl)-7H-pyrrolo[2,3-d]pyrimidin-7-yl)bicyclo[2.2.1]heptan-1-yl)oxazole-2-carboxamide obtained in Step 1 above (7 mg) and THF (2 ml), iodomethane (0.02 ml) and an excessive amount of sodium hydride were added, followed by stirring at room temperature for 15 minutes and then stirring at 50° C. for 20 minutes. The reaction mixture was diluted with water and ethyl acetate, and the organic layer was washed with water and saturated brine and then dried over anhydrous sodium sulfate, followed by filtration and concentration. The resulting residue was purified by silica gel column chromatography to obtain (E)-N-(4-(4-(((dimethylamino) methylene)amino)-6-ethynyl-5-(quinolin-3-yl)-7H-pyrrolo [2,3-d]-pyrimidin-7-yl)bicyclo[2.2.1]heptan-1-yl)-N-methyloxazole-2-carboxamide.

(Step 3) A mixture of (E)-N-(4-(4-(((dimethylamino) methylene)amino)-6-ethynyl-5-(quinolin-3-yl)-7H-pyrrolo [2,3-d]pyrimidin-7-yl)bicyclo[2.2.1]heptan-1-yl)-N -methyloxazole-2-carboxamide obtained in Step 2 above (7 mg) and 7 M ammonia in methanol (1 ml) was stirred for overnight at room temperature and then stirred at 60° C. for 4 hours. The reaction mixture was concentrated and purified by reversed-phase preparative HPLC (water/acetonitrile (0.1% formic acid)) to obtain the above titled compound.

[Example 59]

Pyrazin-2-ylmethyl (4-(4-amino-6-ethynyl-5-(quinolin-3-yl)-7H-pyrrolo[2,3-d]-pyrimidin-7-yl)bicyclo [2.2.1]heptane-1-yl)carbamate To a solution of pyrazin-2-ylmethanol (100 mg) in THF (1 ml), 1,1'-carbonyldiimidazole (147 mg) was added, followed by stirring at room temperature for 2 hours. To the reaction mixture, 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (15 mg) was added, followed by stirring at 40° C. for 12 hours. The reaction mixture was concentrated, and the resulting residue was purified by reversed-phase HPLC to obtain the above titled compound.

[Example 60]

2-((4-(4-Amino-6-ethynyl-5-(quinolin-3-yl)-7H-pyrrolo[2,3-d]pyrimidin-7-yl)bicyclo -[2.2.1]heptane-1-yl)carbamoyl)pyridine 1-oxide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (20 mg) in. DMSO (1 ml), DIPEA (0.013 ml) and picolinic acid N-oxide (7 mg) were added, and WSC (15 mg) and HOBT (12 mg) were then added. After stirring at room temperature for 22 hours, the reaction mixture was purified by reversed-phase preparative HPLC to obtain the above titled compound.

[Example 61]

N-(4-(4-Amino-6-ethynyl-5-(quinolin-3-yl)-7H-pyrrolo[2,3-d]pyrimidin-7-yl)bicyclo -[2.2.1]heptan-1-yl)morpholine-4-carboxamide To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (7.5 mg) in THF (1 ml), DIPEA (0.03 ml) and tert-butyl 4-(chlorocarbonyl) piperazine-1-carboxylate (4.7 mg) were added, followed by stirring at room temperature for 10 minutes. The reaction mixture was concentrated and then purified by reversed-phase preparative HPLC to obtain the above titled compound.

[Example 62]

(S)-N-(4-(4-Amino-6-ethynyl-5-(quinolin-3-yl)-7H-pyrrolo[2,3-d]pyrimidin-7-yl) -bicyclo[2.2.1]heptan-1-yl)morpholine-2-carboxamide (Step 1) To a solution of 7-(4-aminobicyclo[2.2.1]heptan-1-yl)-6-ethynyl-5-(quinolin-3-yl)-7H-pyrrolo[2,3-d]pyrimidine-4-amine obtained in Preparation Example 1 (60 mg) in DMSO (2 ml), DIPEA (0.04 ml), (S)-4-(tert-butoxycarbonyl)morpholine-2-carboxylic acid (33 mg) and HATU (69 mg) were added, followed by stirring at room temperature for 30 minutes. The reaction mixture was diluted with water and extracted with ethyl acetate. The organic layer was washed with saturated brine, dried over anhydrous magnesium sulfate and then concentrated. The resulting residue was purified b silica gel column chromatography to obtain tert-butyl (S)-2-((4-(4-amino-6-ethynyl-5-(quinolin-3-yl)-7H-pyrrolo[2,3-d]pyrimidin-7-yl)bicyclo[2.2.1]heptan-1-yl) -carbamoyl)morpholine-4-carboxylate.

(Step 2) To tert-butyl (S)-2-((4-(4-amino-6-ethynyl-5-(quinolin-3-yl)-7H-pyrrolo[2,3-d]pyrimidin-7-yl)bicyclo[2.2.1]heptan-1-yl)carbamoyl)morpholine-4-carboxylate obtained in Step 1 above (87 mg), chloroform (1 ml) and trifluoroacetic acid (0.5 ml) were added, followed by stirring at room temperature for 30 minutes. The reaction mixture was concentrated and purified by basic silica gel column chromatography to obtain the titled compound.

[Example 63]

(S)-N-(4-(4-Amino-6-ethynyl-5-(quinolin-3-yl)-7H-pyrrolo[2,3-d]pyrimidin-7-yl) -bicyclo[2.2.1]heptan-1-yl)-4-methylmorpholine-2-carboxamide To a mixture of (S)-N-(4-(4-amino-6-ethynyl-5-(quinolin-3-yl)-7H -pyrrolo[2,3-d]pyrimidin-7-yl)bicyclo[2.2.1]heptan-1-yl)-4-methylmorpholine-2-carboxamide obtained in Example 63 (72 mg), THF (2 ml) and 37% aqueous formaldehyde (0.05 ml), a solution of 0.5 M sodium cyanoborohydride and 0.25 M zinc chloride in methanol (0.5 ml) was added, followed by stirring at room temperature for 15 minutes. The reaction mixture was diluted with water and extracted with chloroform. The organic layer was dried over anhydrous magnesium sulfate and then concentrated, The resulting residue was purified by basic silica gel column chromatography to obtain the titled compound.

[Example 64]

N-(4-(4-Amino-6-ethynyl-5-(quinolin-3-yl)-7H-pyrrolo[2,3-d]pyrimidin-7-yl)bicyclo -[2.2.1]heptan-1-yl)imidazo[1,2-a]pyridine-3-carboxamide The same procedures as shown in Example 16 were repeated to obtain the above titled compound, except that [1,2,4]triazolo[1,5-a]pyridine-6-carboxylic acid used in Example 16 was replaced with imidazo[1.2-a]pyridine-3-carboxylic acid.

[Example 65]

N-(4-(4-Amino-6-ethynyl-5-(quinolin-3-yl)-7H-pyrrolo[2,3-d]pyrimidin-7-yl)bicyclo -[2.2.1]heptan-1-yl)imidazo[1,2-a]pyridine-3-carboxamide The same procedures as shown in Example 13 (Step 3) were repeated to obtain the above titled compound, except that 1-methyl-1H-pyrazole-5-carboxylic acid used in Example 13 (Step 3) was replaced with imidazo[1,2-a]pyridine-3-carboxylic acid.

[Example 66]

N-(4-(4-Amino-6-ethynyl-5-(quinolin-3-yl)-7H-pyrrolo[2,3-d]pyrimidin-7-yl)bicyclo -[2.2.1]heptan-1-yl)-5-(hydroxymethyl)pyrazine-2-carboxamide (Step 1) To a solution of methyl 5-formylpyrazinecarboxylate (0.2 g) in methanol (1.0 ml), molecular sieve 3A (0.1 g), methyl orthoformate (0.26 ml) and paratoluenesulfonic acid monohydrate (0.23 g) were added, followed by stirring at 70° C. for overnight. The reaction mixture was concentrated, and the residue was purified by silica gel column chromatography to obtain methyl 5-(dimethoxymethyl)pyrazinecarboxylate.

(Step 2) To a solution of methyl 5-(dimethoxymethyl) pyrazinecarboxylate obtained in Step 1 above (0.26 g) in a mixed solvent of THF (1.2 ml) and methanol (1.2 ml), 0.5 M aqueous sodium hydroxide (2.4 ml) was added at 0° C., followed by stirring for 1 hour. The reaction mixture was concentrated to obtain sodium 5-(dimethoxymethyl) -pyrazinecarboxylate.

(Step 3) To a solution of 7-(4-aminobicyclo[2.2.1]heptan-1-yl)-6-ethynyl-5-(quinolin-3yl)-7H-pyrrolo[2,3-d]pyrimiame-4-amine obtained in Preparation Example 1 (200 mg) in DMSO (5.1 ml), DIPEA (0.26 ml), sodium 5-(dimethoxymethyl)pyrazinecarboxylate obtained in Step 2 above (0.11 g) and HATU (0.29 g) were added, followed by stirring at room temperature for 1 hour. The reaction mixture was mixed with water (10 ml) and stirred at room temperature for 1 hour, and the solid was then collected by filtration. The resulting solid was suspended in a mixed solvent of ethyl acetate (4 ml) and methanol (4 ml), and stirred at room temperature for 1 hour. The solid was collected by filtration and washed with methanol to obtain N-(4-(4-amino-6-ethynyl-5-(quinolin-3-yl)-7H-pyrrolo[2,3-d]pyrimidin-7-yl)bicyclo[2.2.1]heptan-1-yl)5- (dimethoxymethyl)pyrazine-2-carboxamide.

(Step 4) To a solution of N-(4-(4-amino-6-ethynyl-5-(quinolin-3-yl)-7H-pyrrolo[2,3-d]-pyrimidin-7-yl)bicyclo [2.2.1]heptan-1-yl)-5-(dimethoxymethyl)pyrazine-2-carboxamide obtained in Step 3 above (0.33 g) in THF (3.3 ml), trifluoroacetic acid (3.3 ml) and water (1.6 ml) were added, followed by stirring at 60° C. for overnight. The reaction mixture was neutralized with aqueous sodium hydroxide and extracted with ethyl acetate-THF (1:1). The organic layer was washed with saturated brine, dried over anhydrous magnesium sulfate and then concentrated to obtain crude N-(4-(4-amino-6-ethynyl-5-(quinolin-3-yl)-7H-pyrrolo[2,3-d]pyrimidin-7-yl)bicyclo[2.2.1]heptan-1-yl) -5-formylpyrazine-2-carboxamide.

(Step 5) To a solution of crude N-(4-(4-amino-6-ethynyl-5-(quinolin-3-yl)-7H-pyrrolo -[2,3-d]pyrimidin-7-yl)bicyclo[2.2.1]heptan-1-yl)-5-formylpyrazine-2-carboxamide obtained in Step 4 above (10 mg) in a mixture of THF (1 ml) and methanol (1 ml), sodium borohydride (1.4 mg) was added, followed by stirring at room temperature for 1 hour. The reaction mixture was concentrated, and the residue was purified by reversed-phase preparative HPLC to obtain the above titled compound.

[Example 67]

N-(4-(4-Amino-6-ethynyl-5-(quinolin-3-yl)-7H-pyrrolo[2,3-d]pyrimidin-7-yl)bicyclo -[2.2.1]heptan-1-yl)-5-((methylamino)methyl)pyrazine-2-carboxamide To a solution of crude N-(4-4-amino-6-ethynyl-5-(quinolin-3-yl)-7H-pyrrolo -[2,3-d]pyrimidin-7 -yl)bicyclo[2.2.1] heptan-1-yl)-5-formylpyrazine-2-carboxamide obtained in Example 66 (Step 4) (10 mg) in a mixture of THF (0.5 ml) and methanol (0.5 ml), 2 M methylamine in methanol (0.03 ml) was added, followed by stirring at room temperature for 30 minutes. To the reaction mixture, a solution of 0.5 M sodium cyanoborohydride and 0.25 M zinc chloride in methanol (0.1 ml) was added, followed by stirring at room temperature for 1.5 hours. To the reaction mixture, 2 M methylamine in methanol (0.03 ml) was further added and, after 30 minutes, a solution of 0.5 M sodium cyanoborohydride and 0.25 M zinc chloride in methanol (0.1 ml) was then added, followed by stifling at room temperature for 1 hour. The reaction mixture was concentrated and then purified by reversed-phase preparative HPLC to obtain the above titled compound.

[Example 68]

N-(4-(4-Amino-6-ethynyl-5-(quinolin-3-yl)-7H-pyrrolo[2,3-d]pyrimidin-7-yl)bicyclo -[2.2.1]heptan-1-yl)-5-((dimethylamino)methyl)pyrazine-2-carboxamide The same procedures as shown in Example 67 were repeated to obtain the above titled compound, except that 2 M methylamine in methanol solution used in Example 67 was replaced with dimethylamine hydrochloride, and DIPEA (0.06 ml) was further added.

[Example 69]

N-(4-(4-Amino-6-ethynyl-5-(quinolin-3-yl)-7H-pyrrolo[2,3-d]pyrimidin-7-yl)bicyclo -[2.2.1]heptan-1-yl)-5-(morpholinomethyl)pyrazine-2-carboxamide The same procedures as shown in Example 67 were repealed to obtain the above titled compound, except that 2 M methylamine in methanol solution used in Example 67 was replaced with morpholine.

[Example 70]

N-(4-(4-Amino-6-ethynyl-5-(quinolin-3-yl)-7H-pyrrolo[2,3-d]pyrimidin-7-yl)bicyclo -[2.2.1]heptan-1-yl)-5-(dimethylphosphoryl)picolinamide (Step 1) To a solution of methyl 6-bromonicotinate (0.05 g) in 1,4-dioxane (1 ml), tripotassium phosphate (0.15 g), dimethylphosphine oxide (0.036 ml) and nickel(II) 1,3-bis(diphenylphosphino)propane chloride (0.013 g) were added, followed by stirring at 120° C. for 12 hours under a nitrogen atmosphere. The reaction mixture was concentrated, and the residue was purified by silica gel column chromatography to obtain methyl 5-(dimethylphosphoryl)picolinate.

(Step 2) To a solution of methyl 5-(dimethylphosphoryl) picolinate obtained in Step 1 above (0.019 to in a mixture of THF (0.5 ml) and methanol (0.5 ml), 1 N aqueous sodium hydroxide (0.5 ml) was added, followed by stirring at room temperature for 2 hours, The reaction mixture was mixed with 1 N hydrochloric acid (0.5 ml) and concentrated to obtain crude 5-(dimethylphosphoryl)picolinic acid.

(Step 3) The same procedures as shown in Example 13 (Step 3) were repeated to obtain the above titled compound, except that 1-methyl-1H-pyrazole-5-carboxylic acid used in Example 13 (Step 3) was replaced with crude 5-(dimethylphosphoryl)picolinic acid obtained in Step 2 above.

The chemical structural formulae and physical property data of the compounds obtained in Examples 1 to 70 are shown in Table 1 below.

TABLE 1

| Compound No. | Structural formula | NMR | ESI-MS [M + H]+ |
|---|---|---|---|
| 1 | 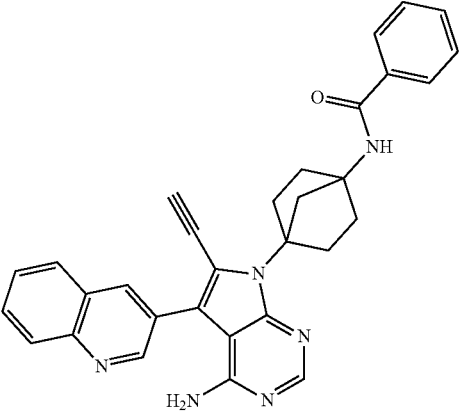 [SMILES: C#Cc1c(-c2cnc3ccccc3c2)c2c(N)ncnc2n1C12CCC(NC(=O)c3ccccc3)(CC1)C2] | 1H-NMR (DMSO-D6) δ: 8.97 (1H, d, J = 2.2 Hz), 8.61 (1H, br s), 8.40 (1H, d, J = 1.8 Hz), 8.20 (1H, s), 8.08-8.03 (2H, m), 7.90-7.87 (2H, m), 7.82-7.77 (1H, m), 7.66-7.62 (1H, m), 7.53-7.43 (3H, m), 6.30 (2H, br s), 4.65 (1H, s), 3.08 (2H, br s), 2.88-2.82 (2H, m), 2.16-2.02 (6H, m). | 499 |

TABLE 1-continued
| Compound No. | Structural formula | NMR | ESI-MS [M + H]+ |
|---|---|---|---|
| 2 | 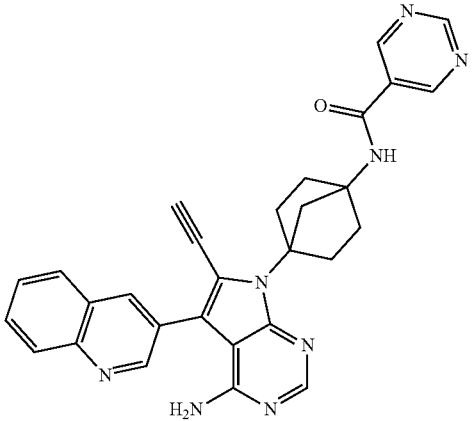 [SMILES: C#Cc1c(-c2cnc3ccccc3c2)c2c(N)ncnc2n1C12CCC(NC(=O)c3cncnc3)(CC1)C2] | 1H-NMR (DMSO-D6) δ: 9.30 (1H, s), 9.19 (2H, s), 9.05 (1H, br s), 8.97 (1H, d, J = 2.2 Hz), 8.40 (1H, d, J = 1.8 Hz), 8.20 (1H, s), 8.07-8.03 (2H, m), 7.82-7.77 (1H, m), 7.66-7.62 (1H, m), 6.31 (2H, br s), 4.66 (1H, s), 3.10 (2H, br s), 2.88-2.83 (2H, m), 2.14-2.04 (6H, m). | 501 |
| 3 | 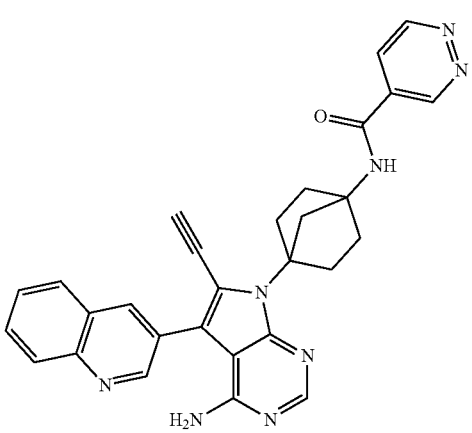 [SMILES: C#Cc1c(-c2cnc3ccccc3c2)c2c(N)ncnc2n1C12CCC(NC(=O)c3ccnnc3)(CC1)C2] | 1H-NMR (DMSO-D6) δ 9.57 (1H, br s), 9.42 (1H, d, J = 5.1 Hz), 9.19 (1H, s), 8.97 (1H, d, J = 1.8 Hz), 8.41-8.39 (1H, m), 8.20 (1H, s), 8.08-8.03 (3H, m), 7.81-7.77 (1H, m), 7.67-7.62 (1H, m), 6.31 (2H, br s), 4.66 (1H, s), 3.10 (2H, br s), 2.88-2.82 (2H, m), 2.14-2.04 (6H, m). | 501 |
| 4 | 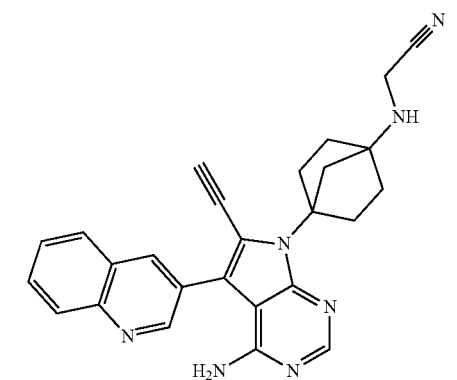 [SMILES: C#Cc1c(-c2cnc3ccccc3c2)c2c(N)ncnc2n1C12CCC(NCC#N)(CC1)C2] | 1H-NMR (DMSO-D6) δ: 8.96 (1H, d, J = 2.2 Hz), 8.38 (1H, d, J = 1.8 Hz), 8.18 (1H, s), 8.07-8.02 (2H, m), 7.81-7.77 (1H, m), 7.66-7.62 (1H, m), 6.27 (2H, br s), 4.59 (1H, s), 3.67 (2H, d, J = 6.8 Hz), 3.06 (1H, t, J = 6.8 Hz), 2.84-2.78 (2H, m), 2.65 (2H, s), 2.01-1.94 (2H, m), 1.86-1.79 (2H, m), 1.64-1.57 (2H, m). | 434 |

TABLE 1-continued

| Compound No. | Structural formula | NMR | ESI-MS [M + H]⁺ |
|---|---|---|---|
| 5 | | 1H-NMR (DMSO-D6) δ: 8.95 (1H, d, J = 2.3 Hz), 8.38 (1H, d, J = 2.3 Hz), 8.19 (1H, s), 8.07-8.05 (1H, m), 8.04-8.02 (1H, m), 7.81-7.77 (1H, m), 7.65-7.62 (1H, m), 6.27 (2H, br s), 4.63 (1H, s), 3.27 (2H, t, J = 5.4 Hz), 3.15 (2H, s), 2.85-2.80 (5H, m), 2.78 (2H, t, J = 5.4 Hz), 2.70 (2H, br s), 2.08-2.01 (2H, m), 1.85-1.78 (2H, m), 1.68-1.62 (2H, m). | 492 |
| 6 | | 1H-NMR (DMSO-D6) δ: 8.92 (1H, d, J = 2.2 Hz), 8.37-8.34 (1H, m), 8.17 (1H, s), 8.06-7.99 (2H, m), 7.81-7.74 (2H, m), 7.65-7.59 (1H, m), 7.39 (1H, d, J = 1.8 Hz), 6.83 (1H, d, J = 1.8 Hz), 6.20 (2H, br s), 4.66 (1H, s), 3.98 (3H, s), 2.79-2.70 (6H, m), 2.19-2.09 (6H, m). | 517 |
| 7 | | 1H-NMR (CDCl3) δ: 9.09 (1H, s), 8.20-8.16 (3H, m), 7.91-7.88 (1H, m), 7.84-7.80 (1H, m), 7.68-7.63 (1H, m), 3.50 (1H, s), 2.91-2.79 (6H, m), 1.98-1.88 (6H, m). | 410 |
| 8 | | 1H-NMR (DMSO-D6) δ: 8.93 (1H, d, J = 1.8 Hz), 8.53-8.51 (1H, m), 8.43-8.36 (2H, m), 8.18 (1H, s), 8.07-8.01 (2H, m), 7.81-7.72 (2H, m), 7.65-7.61 (1H, m), 7.34-7.29 (1H, m), 6.21 (2H, br s), 4.63 (1H, s), 3.67 (2H, s), 2.75-2.70 (6H, m), 1.79-1.74 (6H, m). | 500 |

TABLE 1-continued

| Compound No. | Structural formula | NMR | ESI-MS [M + H]+ |
|---|---|---|---|
| 9 | | 1H-NMR (DMSO-D6) δ: 8.96 (1H, d, J = 2.3 Hz), 8.39 (1H, d, J = 2.1 Hz), 8.19 (1H, s), 8.09-8.02 (2H, m), 7.82-7.78 (1H, m), 7.67-7.63 (1H, m), 6.27 (2H, brs), 4.63 (1H, s), 3.62-3.60 (4H, m), 2.86-2.81 (2H, m), 2.68 (2H, s), 2.56-2.54 (4H, m), 2.09-2.01 (2H, m), 1.86-1.81 (2H, m), 1.66-1.62 (2H, m). | 465 |
| 10 | | 1H-NMR (DMSO-D6) δ: 8.97 (1H, m), 8.40-8.39 (1H, m), 8.19 (1H, s), 8.08-8.03 (2H, m), 7.81-7.78 (1H, m), 7.66-7.62 (1H, m), 6.25 (2H, brs), 4.65-4.62 (2H, m), 3.51 (2H, d, J = 4 Hz), 2.81-2.77 (2H, m), 2.51-2.49 (2H, m), 1.95-1.90 (2H, m), 1.76-1.71 (2H, m), 1.43-1.40 (2H, m). | 410 |
| 11 | | 1H-NMR (DMSO-D6) δ: 8.93 (1H, d, J = 2.2 Hz), 8.38-8.34 (1H, m), 8.17 (1H, s), 8.07-7.98 (2H, m), 7.81-7.74 (1H, m), 7.65-7.58 (1H, m), 6.24 (2H, br s), 4.61 (1H, s), 2.87-2.77 (2H, m), 2.63 (2H, s), 2.21 (6H, s), 2.06-1.93 (2H, m), 1.83-1.73 (2H, m), 1.63-1.52 (2H, m). | 423 |
| 12 | | 1H-NMR (DMSO-D6) δ: 8.96 (1H, d, J = 2.2 Hz), 8.38 (1H, d, J = 1.5 Hz), 8.18 (1H, s), 8.07-8.02 (2H, m), 7.81-7.77 (1H, m), 7.66-7.62 (1H, m), 7.48 (1H, br s), 6.28 (2H, br s), 4.63 (1H, s), 3.98 (2H, q, J = 7.0 Hz), 2.88 (2H, br s), 2.82-2.76 (2H, m), 2.07-1.96 (4H, m), 1.79-1.73 (2H, m), 1.17 (3H, t, J = 7.0 Hz). | 467 |

TABLE 1-continued
| Compound No. | Structural formula | NMR | ESI-MS [M + H]+ |
|---|---|---|---|
| 13 | 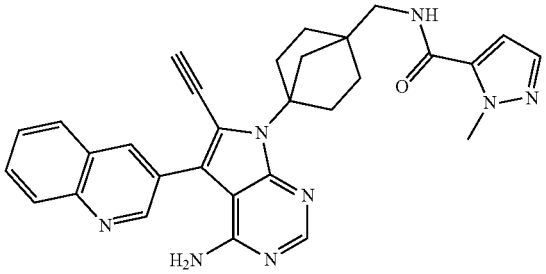 [SMILES: C#Cc1c(-c2cnc3ccccc3c2)c2c(N)ncnc2n1C12CCC(CNC(=O)c3ccnn3C)(CC1)C2] | 1H-NMR (DMSO-D6) δ: 8.97-8.96 (1H, m), 8.61-8.58 (1H, m), 8.39 (1H, brs), 8.18 (1H, s), 8.07-8.03 (2H, m), 7.81-7.78 (1H, m), 7.66-7.62 (1H, m), 7.45 (1H, m), 6.89 (1H, m), 6.26 (2H, brs), 4.60 (1H, s), 4.04 (3H, s), 3.46-3.45 (2H, m), 2.79-2.75 (2H, m), 2.57 (2H, s), 1.99-1.93 (2H, m), 1.78-1.72 (2H, m), 1.51-1.49 (2H, m). | 517 |
| 14 | 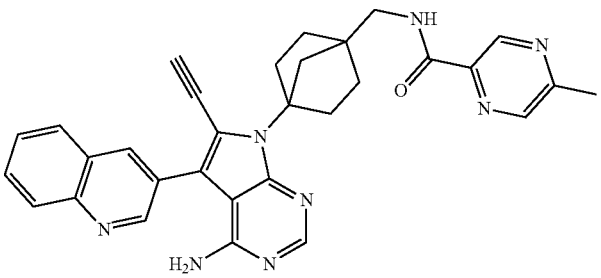 [SMILES: C#Cc1c(-c2cnc3ccccc3c2)c2c(N)ncnc2n1C12CCC(CNC(=O)c3cnc(C)cn3)(CC1)C2] | 1H-NMR (DMSO-D6) δ: 9.07 (1H, s), 8.96 (1H, d, J = 1.8 Hz), 8.91-8.88 (1H, m), 8.64 (1H, s), 8.38 (1H, brs), 8.19 (1H, s), 8.07-8.02 (2H, m), 7.81-7.77 (1H, m), 7.66-7.62 (1H, m), 6.26 (2H, brs), 4.60 (1H, s), 3.55 (2H, d, J = 6.6 Hz), 2.79-2.74 (2H, m), 2.60-2.57 (5H, m), 1.99-1.92 (2H, m), 1.79-1.73 (2H, m), 1.50-1.47 (2H, m). | 529 |
| 15 | 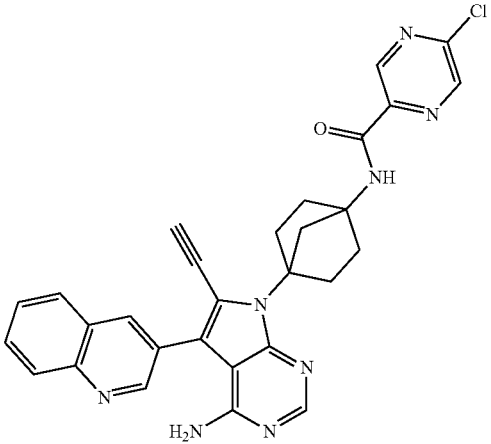 [SMILES: C#Cc1c(-c2cnc3ccccc3c2)c2c(N)ncnc2n1C12CCC(NC(=O)c3cnc(Cl)cn3)(CC1)C2] | 1H-NMR (CDCl3) δ: 9.18-9.18 (1H, m), 9.13 (1H, d, J = 2.2 Hz), 8.52-8.51 (1H, m), 8.29-8.29 (1H, m), 8.25 (1H, s), 8.22 (1H, s), 8.19 (1H, d, J = 8.4 Hz), 7.91-7.89 (1H, m), 7.82-7.78 (1H, m), 7.66-7.62 (1H, m), 3.46 (1H, s), 3.23 (2H, s), 3.02-2.98 (2H, m), 2.29-2.14 (6H, m). | 535, 537 |
| 16 | 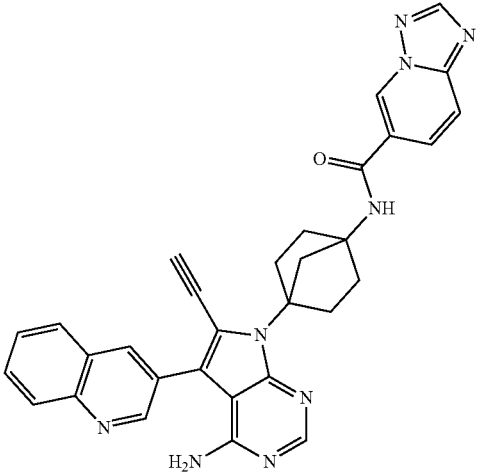 [SMILES: C#Cc1c(-c2cnc3ccccc3c2)c2c(N)ncnc2n1C12CCC(NC(=O)c3ccc4ncnn4c3)(CC1)C2] | 1H-NMR (DMSO-D6) δ: 9.54-9.52 (1H, m), 8.95 (1H, d, J = 2.2 Hz), 8.90 (1H, s), 8.60 (1H, s), 8.40-8.36 (1H, m), 8.18 (1H, s), 8.10-7.99 (3H, m), 7.88 (1H, d, J = 9.5 Hz), 7.80-7.74 (1H, m), 7.65-7.59 (1H, m), 6.28 (2H, br s), 4.64 (1H, s), 3.09 (2H, s), 2.89-2.80 (2H, m), 2.17-2.02 (6H, m). | 540 |

TABLE 1-continued
| Compound No. | Structural formula | NMR | ESI-MS [M + H]+ |
|---|---|---|---|
| 17 | 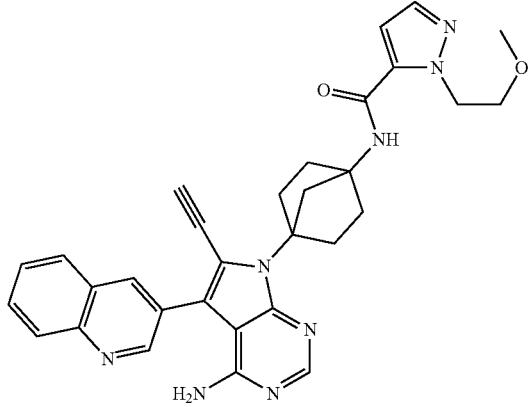 [SMILES: C#Cc1c(-c2cnc3ccccc3c2)c2c(N)ncnc2n1C12CCC(NC(=O)c3ccnn3CCOC)(CC1)C2] | 1H-NMR (DMSO-D6) δ: 8.95 (1H, d, J = 2.2 Hz), 8.64-8.61 (1H, m), 8.39-8.37 (1H, m), 8.18 (1H, s), 8.07-8.00 (2H, m), 7.80-7.74 (1H, m), 7.65-7.59 (1H, m), 7.45 (1H, d, J = 1.8 Hz), 6.87 (1H, d, J = 1.8 Hz), 6.26 (2H, br s), 4.65-4.60 (2H, m), 4.63 (1H, s), 3.65-3.60 (2H, m), 3.18 (3H, s), 3.06-3.01 (2H, m), 2.86-2.79 (2H, m), 2.09-1.97 (6H, m). | 547 |
| 18 | 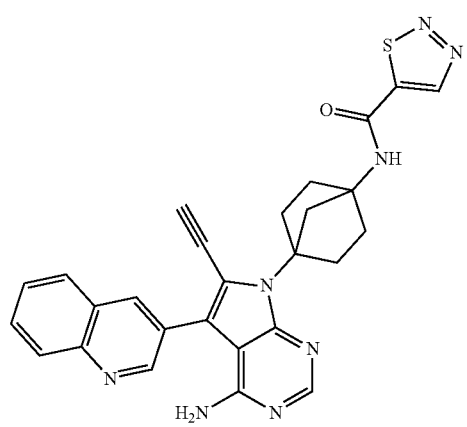 [SMILES: C#Cc1c(-c2cnc3ccccc3c2)c2c(N)ncnc2n1C12CCC(NC(=O)c3cnns3)(CC1)C2] | 1H-NMR (DMSO-D6) δ: 9.40 (1H, s), 9.37 (1H, s), 8.95 (1H, d, J = 2.2 Hz), 8.40-8.36 (1H, m), 8.18 (1H, s), 8.07-8.00 (2H, m), 7.81-7.75 (1H, m), 7.65-7.60 (1H, m), 6.28 (2H, br s), 4.64 (1H, s), 3.10-3.04 (2H, m), 2.89-2.77 (2H, m), 2.12-2.01 (6H, m). | 507 |
| 19 | 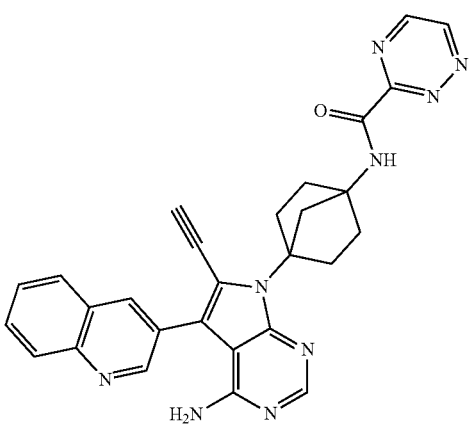 [SMILES: C#Cc1c(-c2cnc3ccccc3c2)c2c(N)ncnc2n1C12CCC(NC(=O)c3nccnn3)(CC1)C2] | 1H-NMR (DMSO-D6) δ: 9.58 (1H, d, J = 2.2 Hz), 9.24 (1H, brs), 9.06-8.95 (2H, m), 8.41 (1H, brs), 8.21 (1H, s), 8.14-7.97 (2H, m), 7.82-7.78 (1H, m), 7.67-7.63 (1H, m), 6.30 (2H, brs), 4.66 (1H, s), 3.14 (2H, brs), 2.92-2.87 (2H, m), 2.27-2.00 (6H, m) | 502 |

TABLE 1-continued

| Compound No. | Structural formula | NMR | ESI-MS [M + H]+ |
|---|---|---|---|
| 20 | | 1H-NMR (DMSO-D6) δ: 8.95 (1H, d, J = 2.2 Hz), 8.61 (1H, s), 8.40-8.36 (1H, m), 8.18 (1H, s), 8.07-7.99 (2H, m), 7.80-7.74 (1H, m), 7.66-7.59 (1H, m), 7.36 (1H, d, J = 2.2 Hz), 6.84 (1H, d, J = 2.2 Hz), 6.27 (2H, br s), 4.63 (1H, s), 4.49-4.41 (1H, m), 3.05 (2H, s), 2.87-2.78 (2H, m), 2.11-1.98 (6H, m), 1.07-1.02 (2H, m), 0.95-0.89 (2H, m). | 529 |
| 21 | | 1H-NMR (CDCl3) δ: 9.15 (1H, d, J = 1.8 Hz), 8.34 (1H, s), 8.31 (1H, d, J = 1.8 Hz), 8.24 (1H, d, J = 2.6 Hz), 8.20-8.17 (1H, m), 7.91-7.89 (1H, m), 7.82-7.77 (1H, m), 7.66-7.61 (2H, m), 7.54 (1H, br s), 6.42-6.40 (1H, m), 4.96 (2H, br s), 3.44 (1H, s), 3.21 (2H, br s), 3.04-2.99 (2H, m), 2.31-2.09 (6H, m). | 489 |
| 22 | | 1H-NMR (DMSO-D6) δ: 8.96-8.91 (2H, m), 8.38-8.35 (1H, m), 8.27 (1H, s), 8.17 (1H, s), 8.06-7.99 (2H, m), 7.79-7.74 (1H, m), 7.66-7.58 (1H, m), 6.27 (2H, br s), 4.63 (1H, s), 4.18 (3H, s), 3.04 (2H, s), 2.87-2.76 (2H, m), 2.09-1.99 (6H, m). | 504 |

TABLE 1-continued

| Compound No. | Structural formula | NMR | ESI-MS [M + H]+ |
|---|---|---|---|
| 23 | | 1H-NMR (DMSO-D6) δ: 8.95 (1H, d, J = 2.2 Hz), 8.41-8.36 (1H, m), 8.28 (1H, s), 8.18 (1H, s), 8.07-7.99 (2H, m), 7.81-7.73 (1H, m), 7.67-7.57 (1H, m), 7.34-7.30 (1H, m), 6.96-6.93 (1H, m), 6.27 (2H, br s), 4.62 (1H, s), 3.93 (3H, s), 3.05 (2H, s), 2.87-2.78 (2H, m), 2.20-2.10 (2H, m), 2.08-1.98 (2H, m), 1.97-1.88 (2H, m). | 503 |
| 24 | | 1H-NMR (DMSO-D6) δ: 8.97 (1H, d, J = 2.2 Hz), 8.63-8.60 (1H, m), 8.40 (1H, d, J = 1.8 Hz), 8.20 (1H, s), 8.08-8.03 (2H, m), 7.81-7.77 (1H, m), 7.66-7.62 (1H, m), 7.44 (1H, d, J = 1.8 Hz), 6.96 (1H, d, J = 2.2 Hz), 6.33-6.24 (2H, m), 4.66 (1H, s), 4.04 (3H, s), 3.06 (2H, s), 2.86-2.81 (2H, m), 2.09-2.03 (6H, m). | 503 |
| 25 | | 1H-NMR (DMSO-D6) δ: 9.49 (1H, s), 8.94 (1H, d, J = 2.2 Hz), 8.72 (1H, s), 8.66 (1H, s), 8.39-8.35 (1H, m), 8.18 (1H, s), 8.06-7.99 (2H, m), 7.80-7.74 (1H, m), 7.65-7.58 (1H, m), 6.26 (2H, br s), 4.64 (1H, s), 3.49 (3H, s), 3.04 (2H, s), 2.88-2.78 (2H, m), 2.16-1.88 (6H, m). | 531 |

TABLE 1-continued
| Compound No. | Structural formula | NMR | ESI-MS [M + H]+ |
|---|---|---|---|
| 26 | 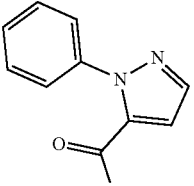 | 1H-NMR (DMSO-D6) δ: 8.94 (1H, d, J = 2.2 Hz), 8.90 (1H, s), 8.39-8.34 (1H, m), 8.17 (1H, s), 8.07-7.99 (2H, m), 7.81-7.74 (1H, m), 7.70 (1H, d, J = 1.8 Hz), 7.65-7.59 (1H, m), 7.50-7.34 (5H, m), 6.86 (1H, d, J = 1.8 Hz), 6.27 (2H, br s), 4.61 (1H, s), 2.97 (2H, s), 2.86-2.75 (2H, m), 2.10-1.88 (6H, m). | 565 |
| 27 | 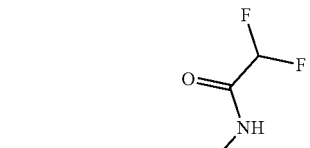 | 1H-NMR (DMSO-D6) δ: 9.10 (1H, brs), 8.97 (1H, d, J = 1.8 Hz), 8.40 (1H, brs), 8.20 (1H, s), 8.08-8.03 (2H, m), 7.82-7.78 (1H, m), 7.67-7.63 (1H, m), 6.29-6.02 (3H, m), 4.65 (1H, s), 3.01 (2H, s), 2.83 (2H, t, J = 7.7 Hz), 2.08-1.93 (6H, m). | 473 |
| 28 | 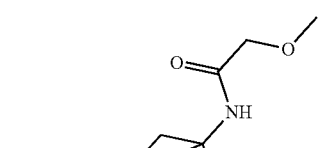 | 1H-NMR (DMSO-D6) δ: 8.97 (1H, d, J = 2.2 Hz), 8.39 (1H, brs), 8.19 (1H, s), 8.08-8.03 (2H, m), 7.87 (1H, brs), 7.82-7.78 (1H, s), 7.66-7.62 (1H, m), 6.28 (2H, brs), 4.64 (1H, s), 3.79 (2H, s), 3.32 (3H, s), 2.98 (2H, s), 2.83-2.79 (2H, m), 2.09-1.86 (6H, m). | 467 |

TABLE 1-continued

| Compound No. | Structural formula | NMR | ESI-MS [M + H]+ |
|---|---|---|---|
| 29 | | 1H-NMR (DMSO-D6) δ: 8.95 (1H, d, J = 2.2 Hz), 8.71-8.67 (1H, m), 8.40-8.37 (1H, m), 8.18 (1H, s), 8.08-8.00 (2H, m), 7.81-7.75 (1H, m), 7.66-7.59 (1H, m), 7.10-7.06 (1H, m), 6.28 (2H, br s), 5.30 (2H, d, J = 48.4 Hz), 4.64 (1H, s), 4.04 (3H, s), 3.04 (2H, s), 2.85-2.77 (2H, m), 2.10-1.99 (6H, m). | 535 |
| 30 | | 1H-NMR (DMSO-D6) δ: 9.01-8.95 (3H, m), 8.44 (1H, brs), 8.41 (1H, brs), 8.21 (1H, s), 8.13-8.12 (1H, m), 8.08-8.04 (2H, m), 7.82-7.78 (1H, m), 7.67-7.63 (1H, m), 6.30 (2H, brs), 4.65 (1H, s), 3.40 (3H, s), 3.14 (2H, s), 2.91-2.88 (2H, m), 2.22-2.05 (6H, m). | 578 |
| 31 | | 1H-NMR (DMSO-D6) δ: 8.97-8.93 (1H, m), 8.56 (1H, s), 8.48 (1H, d, J = 5.9 Hz), 8.39-8.36 (1H, m), 8.34 (1H, s), 8.18 (1H, s), 8.06-7.99 (2H, m), 7.80-7.74 (1H, m), 7.65-7.58 (1H, m), 7.15 (1H, d, J = 5.9 Hz), 6.27 (2H, br s), 4.63 (1H, s), 3.91 (3H, s), 3.04 (2H, s), 2.86-2.77 (2H, m), 2.18-1.88 (6H, m). | 530 |

TABLE 1-continued

| Compound No. | Structural formula | NMR | ESI-MS [M + H]+ |
|---|---|---|---|
| 32 | | 1H-NMR (DMSO-D6) δ: 8.99 (1H, d, J = 2.3 Hz), 8.64-8.63 (1H, m), 8.44-8.41 (1H, m), 8.24-8.18 (2H, m), 8.11-8.03 (3H, m), 7.84-7.78 (1H, m), 7.69-7.63 (1H, m), 6.35 (2H, br s), 4.67 (1H, s), 3.17 (6H, s), 3.12-3.09 (2H, m), 2.91-2.82 (2H, m), 2.27-2.16 (2H, m), 2.12-2.03 (2H, m), 2.03-1.91 (2H, m). 500 MHz | 544 |
| 33 | | 1H-NMR (CDCl3) δ: 9.15 (1H, d, J = 2.0 Hz), 8.26 (1H, d, J = 2.0 Hz), 8.24 (1H, brs), 8.22 (1H, s), 8.19 (1H, d, J = 8.1 Hz), 7.90 (1H, d, J = 8.1 Hz), 7.80 (1H, t, J = 8.1 Hz), 7.64 (1H, t, J = 8.1 Hz), 7.46 (1H, d, J = 1.7 Hz), 6.51 (1H, d, J = 1.7 Hz), 6.28 (2H, brs), 4.19 (3H, s), 3.18 (2H, s), 2.83-3.01 (2H, m), 2.09-2.27 (6H, m), 2.01 (3H, s) | 517 |
| 34 | | 1H-NMR (CDCl3) δ: 9.17 (1H, d, J = 2.2 Hz), 9.14 (1H, d, J = 2.2 Hz), 8.98 (1H, d, J = 1.8 Hz), 8.42-8.41 (1H, m), 8.30-8.30 (1H, m), 8.21-8.18 (2H, m), 7.92-7.89 (1H, m), 7.84-7.79 (1H, m), 7.67-7.63 (1H, m), 6.55 (1H, s), 3.48 (1H, s), 3.24-3.21 (2H, m), 3.04-2.99 (2H, m), 2.27-2.19 (6H, m). | 525 |

TABLE 1-continued

| Compound No. | Structural formula | NMR | ESI-MS [M + H]⁺ |
|---|---|---|---|
| 35 | | 1H-NMR (CDCl3) δ: 9.15-9.12 (1H, m), 8.78 (1H, s), 8.60 (1H, d, J = 2.6 Hz), 8.31-8.30 (2H, m), 8.18 (1H, d, J = 8.4 Hz), 7.90-7.87 (2H, m), 7.81-7.77 (1H, m), 7.65-7.61 (1H, m), 6.48 (1H, br s), 5.28 (2H, brs), 3.45 (1H, s), 3.22 (2H, s), 3.03-2.98 (2H, m), 2.25-2.19 (6H, m). | 518 |
| 36 | | 1H-NMR (DMSO-D6) δ: 9.14-9.09 (1H, m), 8.97-8.92 (1H, m), 8.39-8.35 (1H, m), 8.20-8.15 (1H, m), 8.07-7.98 (2H, m), 7.80-7.73 (1H, m), 7.65-7.58 (1H, m), 6.27 (2H, br s), 4.62 (1H, s), 3.04 (2H, s), 2.87-2.78 (2H, m), 2.64 (3H, s), 2.15-1.93 (6H, m). | 505 |
| 37 | | 1H-NMR (DMSO-D6) δ: 9.04-9.01 (1H, m), 8.94 (1H, d, J = 2.2 Hz), 8.75 (1H, s), 8.58 (1H, s), 8.40-8.36 (1H, m), 8.17 (1H, s), 8.06-7.98 (2H, m), 7.80-7.74 (1H, m), 7.65-7.59 (1H, m), 6.26 (2H, br s), 4.62 (1H, s), 3.09 (2H, s), 2.88-2.78 (2H, m), 2.57 (3H, s), 2.22-1.94 (6H, m). | 515 |

TABLE 1-continued
| Compound No. | Structural formula | NMR | ESI-MS [M + H]+ |
|---|---|---|---|
| 38 | 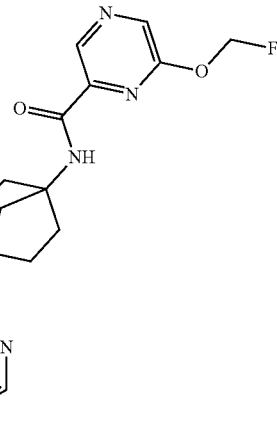 | 1H-NMR (DMSO-D6) δ: 8.98 (1H, d, J = 2.2 Hz), 8.93 (1H, brs), 8.78 (1H, brs), 8.69 (1H, s), 8.41 (1H, brs), 8.22 (1H, s), 8.08-8.04 (2H, m), 7.82-7.78 (1H, m), 7.67-7.63 (1H, m), 6.46-6.33 (4H, m), 4.67 (1H, s), 3.14 (2H, brs), 2.98-2.79 (2H, m), 2.22-2.04 (6H, m). | 549 |
| 39 | 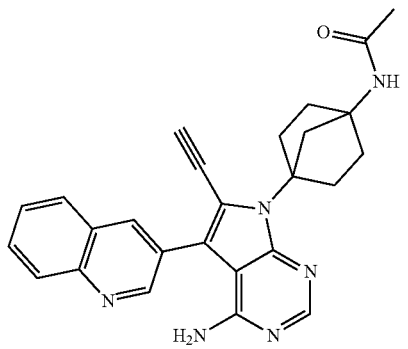 [SMILES: C#Cc1c(-c2cnc3ccccc3c2)c2c(N)ncnc2n1C12CCC(NC(C)=O)(CC1)C2] | 1H-NMR (DMSO-D6) δ: 8.96 (1H, d, J = 2.2 Hz), 8.39-8.38 (1H, m), 8.18 (1H, s), 8.12 (1H, br s), 8.07-8.02 (2H, m), 7.81-7.77 (1H, m), 7.66-7.61 (1H, m), 6.28 (2H, br s), 4.63 (1H, s), 2.93-2.91 (2H, m), 2.82-2.76 (2H, m), 2.06-1.93 (4H, m), 1.85-1.79 (5H, m). | 437 |
| 40 | 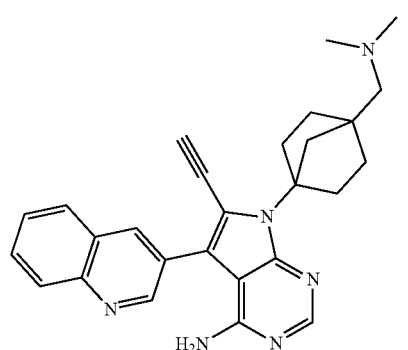 | 1H-NMR (DMSO-D6) δ: 8.97 (1H, d, J = 2.1 Hz), 8.39 (1H, d, J = 2.1 Hz), 8.21-8.17 (2H, m), 8.08-8.02 (2H, m), 7.81-7.78 (1H, m), 7.66-7.63 (1H, m), 6.25 (2H, brs), 4.62 (1H, s), 2.81-2.72 (2H, m), 2.56-2.53 (2H, m), 2.49-2.35 (2H, m), 2.27 (6H, s), 2.01-1.86 (2H, m), 1.80-1.69 (2H, m), 1.58-1.44 (2H, m). | 437 |
| 41 | 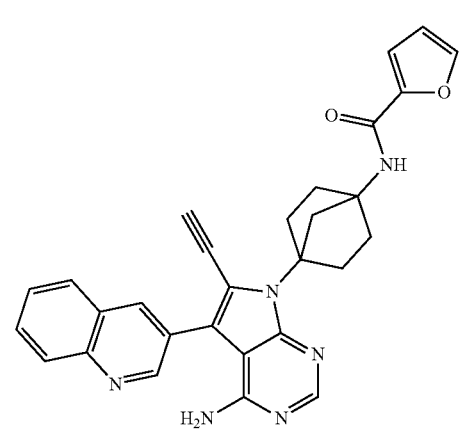 [SMILES: C#Cc1c(-c2cnc3ccccc3c2)c2c(N)ncnc2n1C12CCC(NC(=O)c3ccco3)(CC1)C2] | 1H-NMR (DMSO-D6) δ: 8.97 (1H, d, J = 2.2 Hz), 8.48 (1H, s), 8.40 (1H, d, J = 1.8 Hz), 8.19 (1H, s), 8.08-8.03 (2H, m), 7.82-7.77 (2H, m), 7.66-7.62 (1H, m), 7.16-7.15 (1H, m), 6.61 (1H, dd, J = 3.3, 1.8 Hz), 6.29 (2H, brs), 4.64 (1H, s), 3.05 (2H, br s), 2.87-2.81 (2H, m), 2.14-1.98 (6H, m). | 489 |

TABLE 1-continued

| Compound No. | Structural formula | NMR | ESI-MS [M + H]+ |
|---|---|---|---|
| 42 | | 1H-NMR (DMSO-D6) δ: 9.86 (1H, s), 8.96 (1H, d, J = 2.2 Hz), 8.76 (1H, d, J = 4.4 Hz), 8.41-8.38 (1H, m), 8.26 (1H, s), 8.20 (1H, s), 8.07-7.99 (3H, m), 7.94-7.91 (1H, m), 7.80-7.75 (1H, m), 7.65-7.59 (1H, m), 6.27 (2H, br s), 4.65 (1H, s), 3.13 (2H, s), 2.92-2.83 (2H, m), 2.92-2.18 (2H, m), 2.15-1.98 (4H, m). | 540 |
| 43 | | 1H-NMR (DMSO-D6) δ: 9.03 (1H, d, J = 1.5 Hz), 8.99 (1H, d, J = 2.2 Hz), 8.85 (1H, s), 8.70 (1H, dd, J = 4.8, 1.5 Hz), 8.46-8.45 (1H, m), 8.30 (1H, d, J = 3.3 Hz), 8.25-8.22 (1H, m), 8.10-8.05 (2H, m), 7.85-7.80 (1H, m), 7.69-7.65 (1H, m), 7.51 (1H, dd, J = 8.1, 4.8 Hz), 6.90 (2H, br s), 4.74 (1H, s), 3.09 (2H, br s), 2.89-2.82 (2H, m), 2.17-2.03 (6H, m). | 500 |
| 44 | | 1H-NMR (DMSO-D6) δ: 9.16 (1H, br s), 8.97 (1H, d, J = 2.2 Hz), 8.73 (1H, d, J = 1.8 Hz), 8.40 (1H, d, J = 1.8 Hz), 8.19 (1H, s), 8.07-8.03 (2H, m), 7.82-7.77 (1H, m), 7.66-7.62 (1H, m), 7.11 (1H, d, J = 1.8 Hz), 6.30 (2H, br s), 4.65 (1H, s), 3.09-3.04 (2H, m), 2.86-2.80 (2H, m), 2.10-2.01 (6H, m). | 490 |

TABLE 1-continued
| Compound No. | Structural formula | NMR | ESI-MS [M + H]+ |
|---|---|---|---|
| 45 | 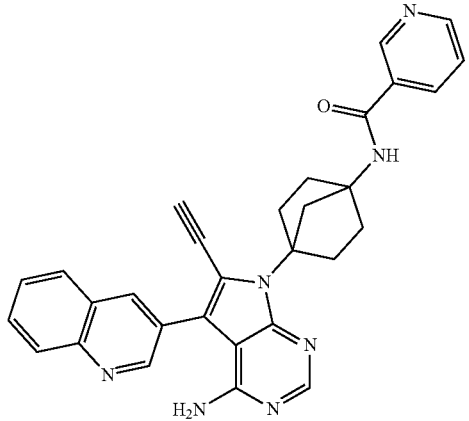 [SMILES: C#Cc1c(-c2cnc3ccccc3c2)c2c(N)ncnc2n1C12CCC(NC(=O)c3cccnc3)(CC1)C2] | 1H-NMR (DMSO-D6) δ: 8.98 (1H, d, J = 2.2 Hz), 8.94 (1H, s), 8.73-8.71 (2H, m), 8.44 (1H, d, J = 1.5 Hz), 8.26 (1H, s), 8.09-8.04 (2H, m), 7.84-7.78 (3H, m), 7.68-7.64 (1H, m), 6.68 (1H, s), 6.68 (1H, s), 4.71 (1H, s), 3.09 (2H, s), 2.89-2.81 (2H, m), 2.18-2.02 (6H, m). | 500 |
| 46 | 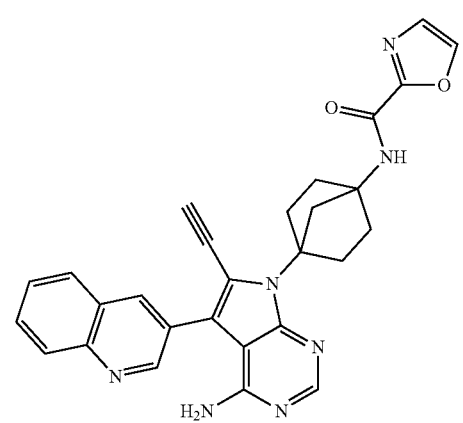 [SMILES: C#Cc1c(-c2cnc3ccccc3c2)c2c(N)ncnc2n1C12CCC(NC(=O)c3ncco3)(CC1)C2] | 1H-NMR (DMSO-D6) δ: 9.04 (1H, s), 8.95 (1H, d, J = 2.2 Hz), 8.40-8.36 (1H, m), 8.30-8.28 (1H, m), 8.18-8.15 (1H, m), 8.07-8.00 (2H, m), 7.80-7.74 (1H, m), 7.65-7.59 (1H, m), 7.43 (1H, s), 6.26 (2H, br s), 4.62 (1H, s), 3.05 (2H, s), 2.87-2.77 (2H, m), 2.18-1.92 (6H, m). | 490 |
| 47 | 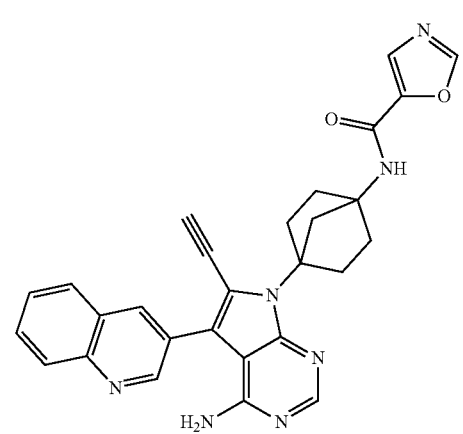 [SMILES: C#Cc1c(-c2cnc3ccccc3c2)c2c(N)ncnc2n1C12CCC(NC(=O)c3cnco3)(CC1)C2] | 1H-NMR (DMSO-D6) δ: 8.95 (1H, d, J = 2.2 Hz), 8.81 (1H, s), 8.52 (1H, s), 8.40-8.36 (1H, m), 8.18 (1H, s), 8.07-7.99 (2H, m), 7.81 (1H, s), 7.80-7.74 (1H, m), 7.66-7.59 (1H, m), 6.29 (2H, br s), 4.63 (1H, s), 3.04 (2H, s), 2.88-2.77 (2H, m), 2.11-1.99 (6H, m). | 468 |

TABLE 1-continued

| Compound No. | Structural formula | NMR | ESI-MS [M + H]⁺ |
|---|---|---|---|
| 48 | | 1H-NMR (DMSO-D6) δ: 9.20-9.19 (1H, m), 8.97 (1H, d, J = 2.2 Hz), 8.88-8.87 (2H, m), 8.73-8.72 (1H, m), 8.41-8.40 (1H, m), 8.20 (1H, s), 8.08-8.03 (2H, m), 7.81-7.77 (1H, m), 7.66-7.62 (1H, m), 6.30 (2H, br s), 4.65 (1H, s), 3.12 (2H, br s), 2.89-2.84 (2H, m), 2.23-2.16 (2H, m), 2.11-1.99 (4H, m). | 501 |
| 49 | | 1H-NMR (DMSO-D6) δ: 9.40-9.36 (1H, m), 9.22-9.16 (1H, m), 8.97-8.92 (1H, m), 8.40-8.35 (1H, m), 8.23-8.15 (2H, m), 8.07-7.98 (2H, m), 7.92-7.86 (1H, m), 7.80-7.72 (1H, m), 7.66-7.56 (1H, m), 6.22 (2H, br s), 4.61 (1H, s), 3.16-3.09 (2H, m), 2.90-2.78 (2H, m), 2.26-1.94 (6H, m). | 501 |
| 50 | | 1H-NMR (DMSO-D6) δ: 8.96 (1H, d, J = 2.2 Hz), 8.39 (1H, d, J = 1.8 Hz), 8.18 (1H, s), 8.07-8.02 (2H, m), 7.81-7.77 (1H, m), 7.66-7.61 (1H, m), 6.27 (2H, br s), 6.14 (1H, s), 5.64 (1H, t, J = 5.5 Hz), 4.63 (1H, s), 3.03-2.97 (2H, m), 2.87 (2H, br s), 2.83-2.77 (2H, m), 2.05-1.92 (4H, m), 1.76-1.69 (2H, m), 0.98 (3H, t, J = 7.1 Hz). | 466 |

TABLE 1-continued

| Compound No. | Structural formula | NMR | ESI-MS [M + H]+ |
|---|---|---|---|
| 51 | | 1H-NMR (DMSO-D6) δ: 9.01-8.94 (3H, m), 8.87 (1H, brs), 8.41 (1H, brs), 8.22 (1H, s), 8.08-8.04 (2H, m), 7.82-7.78 (1H, m), 7.71-7.62 (2H, m), 6.34 (2H, brs), 4.66 (1H, s), 3.11 (2H, s), 2.91-2.86 (2H, m), 2.14-1.91 (6H, m). | 501 |
| 52 | | 1H-NMR (DMSO-D6) δ: 8.96 (1H, d, J = 2.2 Hz), 8.39 (1H, d, J = 1.5 Hz), 8.18 (1H, s), 8.07-8.02 (2H, m), 7.81-7.77 (1H, m), 7.69-7.62 (2H, m), 7.16 (1H, br s), 6.28 (2H, br s), 4.63 (1H, s), 3.41-3.35 (2H, m), 3.10 (2H, br s), 2.84-2.76 (2H, m), 2.20-1.97 (6H, m), 1.06 (3H, t, J = 7.1 Hz). | 482 |
| 53 | | 1H-NMR (CDCl3) δ: 9.13 (1H, s), 8.22 (3H, s), 7.91-7.81 (3H, m), 7.65-7.57 (3H, m), 3.45 (1H, s), 3.24-3.18 (2H, m), 3.03-2.94 (2H, m), 2.32-2.08 (6H, m). | 506 |
| 54 | | 1H-NMR (DMSO-D6) δ: 8.97 (1H, d, J = 2.3 Hz), 8.39 (1H, d, J = 2.1 Hz), 8.19 (1H, s), 8.09-8.01 (2H, m), 7.83-7.77 (1H, m), 7.68-7.61 (1H, m), 6.26 (2H, brs), 4.62 (1H, s), 4.60-4.38 (2H, m), 2.92-2.71 (6H, m) 2.55-2.52 (2H, m), 2.04-1.88 (2H, m), 1.82-1.68 (2H, m), 1.54-1.41 (2H, m). | 455 |

TABLE 1-continued

| Compound No. | Structural formula | NMR | ESI-MS [M + H]+ |
|---|---|---|---|
| 55 | | 1H-NMR (CDCl3) δ: 9.10-9.07 (1H, m), 8.20-8.18 (3H, m), 7.89-7.87 (2H, m), 7.82-7.78 (1H, m), 7.66-7.62 (1H, m), 3.49 (1H, s), 3.05 (2H, s), 2.86-2.81 (6H, m), 2.41 (6H, s), 2.19-2.15 (6H, m). | 494 |
| 56 | | 1H-NMR (CDCl3) δ: 9.09 (1H, s), 8.25 (1H, s), 8.21 (1H, s), 8.18 (1H, d, J = 8.8 Hz), 7.88 (1H, d, J = 7.7 Hz), 7.82-7.78 (1H, m), 7.65-7.61 (1H, m), 5.07 (1H, s), 4.24 (4H, s), 4.00 (4H, s), 3.49 (1H, s), 2.86-2.82 (6H, m), 2.68 (3H, s), 2.41-2.37 (6H, m). | 563 |
| 57 | | 1H-NMR (CDCl3) δ: 9.06 (1H, s), 8.80 (1H, s), 8.45 (1H, s), 8.41 (1H, s), 8.34 (1H, s), 8.16 (1H, d, J = 7.5 Hz), 7.88 (1H, d, J = 7.5 Hz), 7.77 (1H, t, J = 7.5 Hz), 7.61 (1H, t, J = 7.5 Hz), 3.50 (1H, s), 3.21-3.37 (2H, m), 3.16 (3H, brs), 2.90-3.05 (2H, m), 2.64 (3H, s), 2.50-2.75 (2H, m), 2.15-2.25 (2H, m), 2.03-2.13 (2H, m) | 529 |
| 58 | | 1H-NMR (CDCl3) δ: 9.14 (1H, d, J = 1.8 Hz), 8.30 (1H, d, J = 1.8 Hz), 8.23 (1H, s), 8.21 (1H, d, J = 7.5 Hz), 8.19 (1H, s), 7.91 (1H, d, J = 7.5 Hz), 7.82 (1H, t, J = 7.5 Hz), 7.76 (1H, s), 7.66 (1H, t, J = 7.5 Hz), 3.49 (1H, s), 3.47 (3H, s), 3.26 (2H, brs), 2.89-3.01 (2H, m), 2.53-2.73 (2H, m), 2.13-2.26 (2H, m), 2.02-2.11 (2H, m) | 504 |

TABLE 1-continued
| Compound No. | Structural formula | NMR | ESI-MS [M + H]+ |
|---|---|---|---|
| 59 | 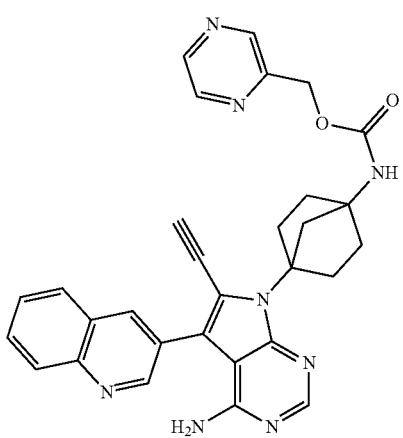 [SMILES: C#Cc1c(-c2cnc3ccccc3c2)c2c(N)ncnc2n1C12CCC(NC(=O)OCc3cnccn3)(CC1)C2] | 1H-NMR (DMSO-D6) δ: 8.97 (1H, d, J = 2.3 Hz), 8.73 8.70 (1H, m), 8.67 8.65 (1H, m), 8.64 8.61 (1H, m), 8.41-8.39 (1H, m), 8.20 (1H, s), 8.10-8.03 (2H, m), 7.87 (1H, br s), 7.83-7.78 (1H, m), 7.68-7.63 (1H, m), 6.22 (2H, br s), 5.17 (2H, s), 4.64 (1H, s), 2.97-2.90 (2H, m), 2.86-2.77 (2H, m), 2.10-2.00 (4H, m), 1.88-1.73 (2H, m). | 531 |
| 60 | 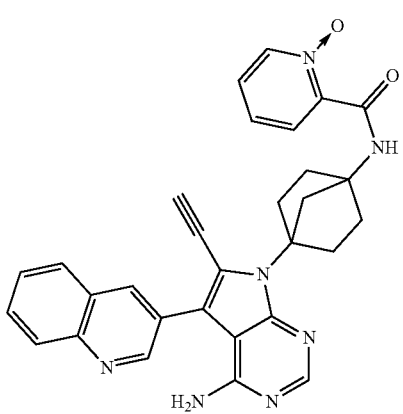 [SMILES: C#Cc1c(-c2cnc3ccccc3c2)c2c(N)ncnc2n1C12CCC(NC(=O)c3cccc[n+]3[O-])(CC1)C2] | 1H-NMR (DMSO-D6) δ: 11.72 (1H, s), 8.97 (1H, d, J = 2.0 Hz), 8.44 8.48 (1H, m), 8.40 (1H, br d, J = 2.0 Hz), 8.24-8.28 (1H, m), 8.21 (1H, s), 8.02-8.08 (2H, m), 7.77-7.82 (1H, m), 7.61-7.67 (3H, m), 6.30 (2H, br s), 4.66 (1H, s), 3.10 (2H, s), 2.83-2.93 (2H, m), 1.95-2.22 (6H, m). | 516 |
| 61 | 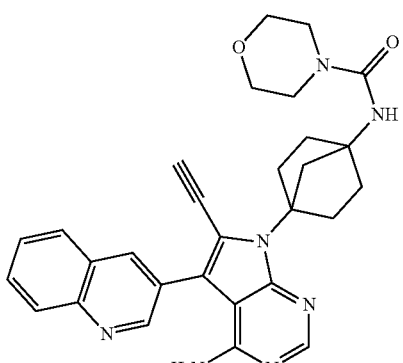 | 1H NMR (CHLOROFORM-d): δ 9.04-9.10 (1H, m), 8.30 (1H, br s), 8.19-8.25 (1H, m), 8.16 (1H, br d, J = 8.3 Hz), 7.90 (1H, br dd, J = 3.0 and 7.9 Hz), 7.73-7.85 (1H, m), 7.58-7.72 (1H, m), 7.27-7.30 (1H, m), 3.60-3.75 (4H, m), 3.50 (1H, s), 3.29-3.41 (4H, m), 2.48-3.12 (6H, m), 1.86-2.27 (4H, m) | 508 |

| Compound No. | Structural formula | NMR | ESI-MS [M + H]+ |
|---|---|---|---|
| 62 | 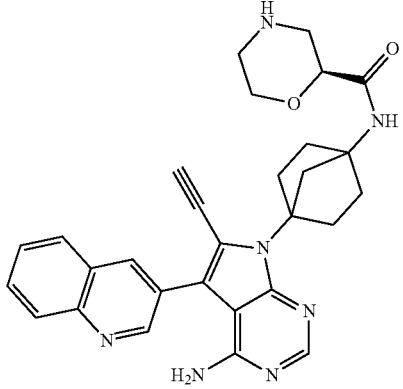 [SMILES: C#Cc1c(-c2cnc3ccccc3c2)c2c(N)ncnc2n1C12CCC(NC(=O)[C@@H]3CNCCO3)(CC1)C2] | 1H-NMR (DMSO-D6) δ: 8.95 (1H, d, J = 2.3 Hz), 8.39-8.38 (1H, m), 8.18 (1H, s), 8.07-8.02 (2H, m), 7.81-7.77 (1H, m), 7.66-7.62 (1H, m), 7.57 (1H, br s), 6.26 (2H, br s), 4.62 (1H, s), 3.83-3.74 (2H, m), 3.50-3.44 (1H, m), 3.00-2.94 (3H, m), 2.82-2.74 (2H, m), 2.69-2.57 (3H, m), 2.07-1.94 (4H, m), 1.89-1.82 (2H, m). | 508 |
| 63 | 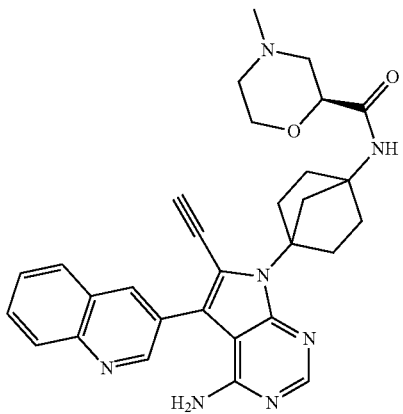 [SMILES: C#Cc1c(-c2cnc3ccccc3c2)c2c(N)ncnc2n1C12CCC(NC(=O)[C@@H]3CN(C)CCO3)(CC1)C2] | 1H-NMR (DMSO-D6) δ: 8.95 (1H, d, J = 2.3 Hz), 8.38 (1H, d, J = 2.3 Hz), 8.18 (1H, s), 8.07-8.02 (2H, m), 7.81-7.77 (1H, m), 7.67-7.62 (2H, m), 6.27 (2H, br s), 4.62 (1H, s), 3.89-3.85 (2H, m), 3.61-3.52 (1H, m), 2.98-2.76 (5H, m), 2.60-2.56 (1H, m), 2.19 (3H, s), 2.07-1.83 (8H, m). | 522 |
| 64 | 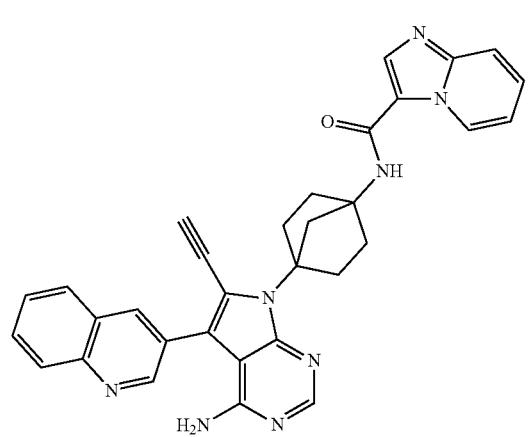 [SMILES: C#Cc1c(-c2cnc3ccccc3c2)c2c(N)ncnc2n1C12CCC(NC(=O)c3cnc4ccccn34)(CC1)C2] | 1H NMR (400 MHz, DMSO-d6) δ - 9.49 (d, J = 7.0 Hz, 1H), 8.97 (m, 1H), 8.63 (s, 1H), 8.45 (s, 1H), 8.41-8.38 (m, 1H), 8.20 (s, 1H), 8.07-8.02 (m, 2H), 7.81-7.75 (m, 1H), 7.70-7.60 (m, 2H), 7.47-7.40 (m, 1H), 7.12-7.06 (m, 1H), 6.29 (br s, 2H), 4.65 (s, 1H), 3.12-3.10 (m, 2H), 2.93 2.75 (m, 2H), 2.18 2.03 (m, 6H) | 539 |

TABLE 1-continued

| Compound No. | Structural formula | NMR | ESI-MS [M + H]+ |
|---|---|---|---|
| 65 | | 1H NMR (400 MHz, DMSO-d6) δ = 9.38-9.35 (m, 1H), 9.21-9.18 (m, 1H), 8.98-8.97 (m, 1H), 8.92 (s, 1H), 8.61 (s, 1H), 8.42-8.38 (m, 1H), 8.20 (s, 1H), 8.11-8.00 (m, 3H), 7.83-7.76 (m, 1H), 7.67-7.61 (m, 1H), 6.28 (br s, 2H), 4.66 (s, 1H), 3.12 (s, 2H), 2.97-2.77 (m, 2H), 2.18-2.04 (m, 6H) | 540 |
| 66 | | 1H NMR (400 MHz, DMSO d6) δ = 9.11 9.10 (m, 1H), 8.98 (m, 1H), 8.85 (s, 1H), 8.75 (m, 1H), 8.41 (m, 1H), 8.21 (s, 1H), 8.08-8.04 (m, 2H), 7.82-7.78 (m, 1H), 7.67-7.63 (m, 1H), 6.29 (brs, 2H), 5.76 (t, J = 5.8 Hz, 1H), 4.74 (d, J = 5.9 Hz, 2H), 4.65 (s, 1H), 3.18-3.09 (m, 2H), 2.97-2.78 (m, 2H), 2.23-1.98 (m, 6H). | 531 |
| 67 | | 1H NMR (400 MHz, DMSO d6) δ = 9.11 (m, 1H), 8.98 (m, 1H), 8.84 (s, 1H), 8.74-8.73 (m, 1H), 8.41 (m, 1H), 8.21-8.19 (m, 2H), 8.08-8.04 (m, 2H), 7.82-7.78 (m, 1H), 7.67-7.63 (m, 1H), 6.30 (brs, 2H), 4.65 (s, 1H), 3.91 (s, 2H), 3.13 (s, 2H), 2.90-2.88 (m, 2H), 2.33 (s, 3H), 2.24-2.01 (m, 6H) | 544 |

TABLE 1-continued

| Compound No. | Structural formula | NMR | ESI-MS [M + H]+ |
|---|---|---|---|
| 68 | | 1H NMR (400 MHz, DMSO-d6) δ = 9.11 (m, 1H), 8.98 (m, 1H), 8.86 (s, 1H), 8.72 8.71 (m, 1H), 8.41 (m, 1H), 8.21 (s, 1H), 8.08-8.04 (m 2H), 7.82-7.78 (m, 1H), 7.67-7.63 (m, 1H), 6.30 (brs, 2H), 4.65 (s, 1H), 3.69 (s, 2H), 3.13 (s, 2H), 2.91-2.83 (m, 2H), 2.22-1.99 (m, 12H) | 558 |
| 69 | | 1H NMR (400 MHz, DMSO-d6) δ = 9.12 9.11 (m, 1H), 8.98 (m, 1H), 8.84 (s, 1H), 8.74 (m, 1H), 8.41 (m, 1H), 8.21 (s, 1H), 8.08-8.04 (m, 2H), 7.82-7.78 (m, 1H), 7.67-7.63 (m, 1H), 6.30 (brs, 2H), 4.65 (s, 1H), 3.76 (s, 2H), 3.61-3.58 (m, 4H), 3.13 (s, 2H), 2.91-2.85 (m, 2H), 2.46-2.44 (m, 4H), 2.22-1.99 (m, 6H) | 600 |
| 70 | | 1H-NMR (400 MHz, CDCl3) δ = 9.17 (d, 1H, J = 2.3 Hz), 8.93 (m, 1H), 8.45 (m, 1H), 8.35 (m, 2H), 8.23 (m, 2H), 7.95 (m, 1H), 7.86 (m, 1H), 7.71 (m, 1H), 3.54 (s, 1H), 3.26 (m, 2H), 3.03 (m, 2H), 2.28 (s, 6H), 1.91 (s, 3H), 1.89 (s, 3H) | 576 |

Comparative Example A
(R)-1-(3(4-Amino-5-(quinolin-3-yl)-7H-pyrrolo[2,3-d]pyrimidin-7-yl)pyrrolidin-1-yl)-prop-2-en-1-one

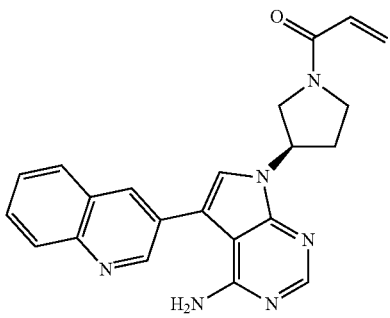 [SMILES: C=CC(=O)N1CC[C@@H](n2cc(-c3cnc4ccccc4c3)c3c(N)ncnc32)C1]

Comparative Example B
(R)-1-(3-(4-Amino-6-ethynyl-5-(quinolin-3-yl)-7H-pyrrolo[2,3-d]pyrimidin-7-yl) -pyrrolidin-1-yl)-prop-2-en-1-one

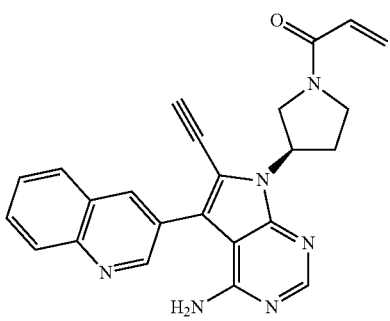 [SMILES: C#Cc1c(-c2cnc3ccccc3c2)c2c(N)ncnc2n1[C@@H]1CCN(C(=O)C=C)C1]

The above compounds were synthesized according to the procedures described in WO2013/118817.

Test Examples

The compounds of the above examples and comparative examples were evaluated by the test methods shown below.

Test Example 1

Test for inhibitory effect against the activity of various EGFR kinases (in vitro)
1) Measurement of inhibitory activity against EGFR (d746-750/T790M/C797S) kinase
The compounds of the above examples and comparative examples were measured for their inhibitory activity against EGFR (d746-750/T790M/C797S) kinase activity. Among the materials required for measurement of this inhibitory activity, the kinase protein (SEQ ID NO: 1) used was prepared as follows: the cytoplasmic domain of human EGFR (d746-750/T790M/C797S) fused at the ammo terminal end with a glutathione-S-transferase (GST) tag was expressed M insect cells (Sf9) by the baculovirus expression system and then purified an a glutathione sepharose column. For use as a substrate peptide, a peptide biotinylated at the N-terminal end (biotin -EEPLYWSFPAKKK) was synthesized by reference to Perkin Elmer LabChip® series reagent FL-Peptide 22.

Procedures for measurement of the inhibitory activity are as follows. First, the compounds of the present invention were each dissolved in dimethyl sulfoxide (DMSO), and their serial dilutions were then prepared with DMSO. Secondly, each compound serial dilution (final concentration of DMSO during kinase reaction: 2.5%) or DMSO (final concentration: 2.5%) was mixed with a solution containing the substrate peptide (final concentration: 250 nM), magnesium chloride (final concentration: 10 mM), manganese chloride (final concentration: 10 mM) and ATP (final concentration: 6 μM) in a kinase reaction buffer (Carna Biosciences Inc., Japan), and the EGFR (d746-750/T790M/C797S) protein was further added thereto, followed by incubation at 25° C. for 120 minutes to cause kinase reaction. To the reaction solution, EDTA was added to give a final concentration of 24 mM to thereby stop the reaction, followed by addition of a phospholylated tyrosine detection solution containing europium-labeled anti-phosphorylated tyrosine antibody PT66 (Perkin Elmer) and SureLight APC-SA (Perkin Elmer). The reaction solution was allowed to stand at room temperature for 2 hours or longer. As a background, DMSO was used instead of each compound solution in .DMSO, and EDIA was added prior to the addition of the EGFR EGFR (d746-750/T790M/C797S) protein, followed by incubation at 25° C. for 120 minutes. The same detection solution was also added to this reaction solution, which was then allowed to stand for 2 hours or longer. Finally, all the test samples were measured with a PHERAstar FS reader (BMG LABTECH) for their fluorescence intensity at two wavelengths of 620 nm and 665 nm upon irradiation with an excitation light of 337 nm wavelength, and the ratio of fluorescence intensities at these two wavelengths was obtained as data for each compound.

In analysis of the measured data, the fluorescence intensity ratio data in the sample where DMSO was added at a final concentration of 2.5% to cause kinase reaction was set to 0% inhibition of phosphorylation reaction, while the fluorescence intensity ratio data in the background was set to 100% inhibition of phosphorylation reaction, and the concentration of each compound required to produce 50% inhibition of EGFR (d746-750/T790M/C797S)—induced phosphorylation reaction was defined to be an IC50 value (nM).

Moreover, as control compounds, the above Comparative Example A (Example 3 in WO2013/118817) and Comparative Example B (Example 35 in WO2013/118817) known to have EGFR inhibitory activity were used.

The measured data are shown in Table 2 below.

TABLE 2

| | EGFR (d746-750/T790M/C797S) IC50 value (nM) |
|---|---|
| Example1 | <0.3 |
| Example2 | <0.3 |
| Example3 | <0.3 |
| Example4 | 0.36 |
| Example5 | 0.32 |
| Example6 | <0.3 |
| Example7 | 0.80 |
| Example8 | <0.3 |
| Example9 | <0.3 |
| Example10 | <0.3 |
| Example11 | <0.3 |
| Example12 | <0.3 |
| Example13 | <0.3 |
| Example14 | <0.3 |
| Example15 | <0.3 |
| Example16 | <0.3 |
| Example17 | <0.3 |

TABLE 2-continued

| | EGFR (d746-750/T790M/C797S) IC50 value (nM) |
|---|---|
| Example18 | <0.3 |
| Example19 | <0.3 |
| Example20 | <0.3 |
| Example21 | <0.3 |
| Example22 | <0.3 |
| Example23 | <0.3 |
| Example24 | <0.3 |
| Example25 | <0.3 |
| Example26 | <0.3 |
| Example27 | <0.3 |
| Example28 | <0.3 |
| Example29 | <0.3 |
| Example30 | <0.3 |
| Example31 | <0.3 |
| Example32 | <0.3 |
| Example33 | <0.3 |
| Example34 | <0.3 |
| Example35 | <0.3 |
| Example36 | <0.3 |
| Example37 | <0.3 |
| Example38 | <0.3 |
| Example39 | <0.3 |
| Example40 | <0.3 |
| Example41 | <0.3 |
| Example42 | <0.3 |
| Example43 | <0.3 |
| Example44 | <0.3 |
| Example45 | <0.3 |
| Example46 | <0.3 |
| Example47 | <0.3 |
| Example48 | <0.3 |
| Example49 | <0.3 |
| Example50 | <0.3 |
| Example51 | <0.3 |
| Example52 | <0.3 |
| Example53 | <0.3 |
| Example54 | <0.3 |
| Example55 | <0.3 |
| Example56 | <0.3 |
| Example57 | <0.3 |
| Example58 | <0.3 |
| Comparative Example A | 142 |
| Comparative Example B | 26 |

2) Measurement of inhibitory activity against EGFR (L858R/T790M/C797S) kinase

The compounds of the presein invention were measured for their inhibitory activity against EGFR (L858R/T790M/C797S) kinase activity.

The materials, measurement procedures and data analysis method used in this test are substantially the same as those shown in the section "Measurement of inhibitory activity against EGFR (d746-750/T790M/C797S) kinase." However, among the materials, the kinase protein (SEQ ID NO: 2) used was prepared as follows: the cytoplasmic domain of human EGFR (L858R/T790M/C797S) fused at the amino terminal end with a GST tag was expressed in insect cells (Sf9) by the baculovirus expression system and then purified on a glutathione sepharose column. In the measurement procedures, the final concentration of ATP was set to 0.5 µM. Finally, data analysis was conducted to determine the IC50 value (nM) of each compound against EGFR (L858R/T790M/C797S).

Moreover, as control compounds, the above Comparative Example A (Example 3 in WO2013/118817) and Comparative Example B (Example 35 in W)2013/118817) known to have EGFR inhibitory activity were used.

The measured data are shown in Table 3 below.

TABLE 3

| | EGFR (L858R/T790M/C797S) IC50 value (nM) |
|---|---|
| Example1 | 0.46 |
| Example2 | <0.3 |
| Example3 | <0.3 |
| Example4 | 0.38 |
| Example6 | 0.70 |
| Example10 | 0.56 |
| Example11 | 0.69 |
| Example12 | 0.39 |
| Example15 | 0.52 |
| Example16 | 0.36 |
| Example17 | 0.79 |
| Example18 | 0.42 |
| Example19 | <0.3 |
| Example20 | 0.44 |
| Example22 | 0.42 |
| Example23 | 0.42 |
| Example24 | <0.3 |
| Example25 | 0.60 |
| Example26 | 0.62 |
| Example27 | 0.47 |
| Example28 | 1.1 |
| Example29 | 0.31 |
| Example30 | 0.33 |
| Example31 | 0.52 |
| Example34 | <0.3 |
| Example35 | 0.50 |
| Example36 | 0.56 |
| Example37 | 0.52 |
| Example38 | 0.66 |
| Example39 | 0.36 |
| Example41 | 0.39 |
| Example42 | <0.3 |
| Example44 | 0.32 |
| Example46 | 0.41 |
| Example47 | 0.59 |
| Example48 | <0.3 |
| Example49 | 0.47 |
| Example50 | 0.68 |
| Example51 | 0.34 |
| Example52 | 0.60 |
| Example53 | 0.69 |
| Example58 | 1.5 |
| Comparative Example A | 102 |
| Comparative Example B | 43 |

3) Measurement of inhibitory activity against EGFR (d746-750/C797S) kinase

The compounds of the present invention were measured for their inhibitory activity against EGFR (d746-750/C797S) kinase activity.

The materials, measurement procedures and data analysis method used in this test are substantially the same as those shown in the section "Measurement of inhibitory activity aiainst EGFR (d746-750/T790M/C797S) kinase." However, among the materials, the kinase protein used was a purified recombinant human EGFR (d746-750/C797S) protein purchased from SignalChem, while the kinase reaction buffer used was 13.5 mM Tris (pH 7.5) containing 2 mM dithiothreitol and 0.009% Tween-20. In the measurement procedures, the final concentration of ATP was set to 14 µM, the final concentration of maganesium chloride was set to 20 mM, the final concentration of manganese chloride was set to 12.5 mM, the incubation time for kinase reaction was set to 60 minutes, and the final concentration of EDTA used to stop the kinase reaction was set to 40 mM. Finally, data analysis was conducted to determine to IC50 value (nM) of each compound against EGFR (d746-750/C797S).

Moreover, as control compounds, the above Comparative Example A (Example 3 in WO2013/118817) and Comparative Example B (Example 35 in WO2013/118817) known to have EGFR inhibitory activity were used.

The measured data are shown in Table 4 below.

TABLE 4

|  | EGFR (d746-750/C797S) IC50 value (nM) |
| --- | --- |
| Example1 | 1.8 |
| Example2 | 0.29 |
| Example3 | <0.3 |
| Example4 | 1.0 |
| Example5 | 1.2 |
| Example6 | 2.1 |
| Example7 | 2.3 |
| Example8 | 0.73 |
| Example9 | 0.36 |
| Example10 | 0.62 |
| Example11 | 1.6 |
| Example12 | 2.4 |
| Example13 | 0.67 |
| Example14 | 0.79 |
| Example15 | 0.79 |
| Example16 | 0.45 |
| Example17 | 0.61 |
| Example18 | 0.78 |
| Example19 | <0.3 |
| Example20 | 0.68 |
| Example21 | 0.78 |
| Example22 | <0.3 |
| Example23 | 0.70 |
| Example24 | 0.50 |
| Example25 | 0.40 |
| Example26 | 0.71 |
| Example27 | 1.2 |
| Example28 | 0.89 |
| Example29 | 0.32 |
| Example30 | 0.64 |
| Example31 | 0.49 |
| Example32 | 0.59 |
| Example33 | 1.9 |
| Example34 | 0.46 |
| Example35 | 0.55 |
| Example36 | 0.61 |
| Example37 | 0.50 |
| Example38 | 0.56 |
| Example39 | 0.75 |
| Example40 | 2.6 |
| Example41 | 1.4 |
| Example42 | 0.48 |
| Example43 | 0.73 |
| Example44 | 0.73 |
| Example45 | 0.67 |
| Example46 | 0.43 |
| Example47 | 0.33 |
| Example48 | 0.46 |
| Example49 | 0.49 |
| Example50 | 0.97 |
| Example51 | 0.83 |
| Example52 | 1.5 |
| Example53 | 0.88 |
| Example54 | 1.5 |
| Example55 | 0.86 |
| Example56 | 0.84 |

TABLE 4-continued

|  | EGFR (d746-750/C797S) IC50 value (nM) |
| --- | --- |
| Example57 | 2.5 |
| Example58 | 2.2 |
| Comparative Example A | 264 |
| Comparative Example B | 93 |

4) Measurement of inhibitory activity against EGFR (L858R/C797S) kinase

The compounds of the present invention were measured for their inhibitory activity aeainst EGFR (L858R/C797S) kinase activity.

The materials, measurement procedures and data analysis method used in this test are stibstantially the same as those shown in the section "Measurement of inhibitory activity against EGFR (d746-750/C797S) kinase." However, among the materials, the kinase protein used was a purified recombinant human EGFR (C797S/L858R) protein purchased from SignalChem. In the measurement procedures, the final concentration of ATP was set to 4 μM, and the incubation time for kinase reaction was set to 90 minutes. Finally, data analysis was conducted determine the IC50 value (nM) of each compound against EGFR (L858R/C797S).

Moreover, as control compounds, the above Comparative Example A (Example 3 in WO2013/118817) and Comparative Example B (Example 35 in WO2013/118817) known to have EGFR inhibitory activity were used.

The measured data are shown in Table 5 below.

TABLE 5

|  | EGFR (L858R/C797S) IC50 value (nM) |
| --- | --- |
| Example1 | 2.8 |
| Example2 | 0.46 |
| Example3 | 0.37 |
| Example4 | 1.5 |
| Example5 | 2.8 |
| Example6 | 4.6 |
| Example7 | 2.9 |
| Example8 | 1.4 |
| Example9 | 1.0 |
| Example10 | 0.95 |
| Example11 | 2.4 |
| Example12 | 3.8 |
| Example13 | 0.69 |
| Example14 | 1.3 |
| Example15 | 1.0 |
| Example16 | 0.49 |
| Example17 | 0.66 |
| Example18 | 0.67 |
| Example19 | 0.30 |
| Example20 | 1.2 |
| Example21 | 0.98 |
| Example22 | 0.35 |
| Example23 | 0.84 |
| Example24 | 0.59 |
| Example25 | 0.59 |
| Example26 | 0.84 |
| Example27 | 2.4 |
| Example28 | 1.7 |
| Example29 | 0.39 |
| Example30 | 1.2 |
| Example31 | 0.62 |
| Example32 | 0.78 |
| Example33 | 2.3 |
| Example34 | 0.45 |

TABLE 5-continued

| | EGFR (L858R/C797S) IC50 value (nM) |
|---|---|
| Example35 | 0.84 |
| Example36 | 0.99 |
| Example37 | 0.69 |
| Example38 | 0.97 |
| Example39 | 1.4 |
| Example40 | 4.0 |
| Example41 | 1.9 |
| Example42 | 0.43 |
| Example43 | 0.49 |
| Example44 | 0.94 |
| Example45 | 0.53 |
| Example46 | 0.43 |
| Example47 | 0.36 |
| Example48 | 0.60 |
| Example49 | 0.63 |
| Example50 | 2.0 |
| Example51 | 0.99 |
| Example52 | 2.6 |
| Example53 | 1.2 |
| Example54 | 2.8 |
| Example55 | 1.2 |
| Example56 | 0.90 |
| Example57 | 4.4 |
| Example58 | 3.4 |
| Comparative Example A | 187 |
| Comparative Example B | 97 |

5) EGFR (WT)

The compounds of the present invention were measured for their inhibitory activity nainst EGFR (WT) kinase activity.

The materials, measurement procedures and data analysis method used in this test. are substantially the same as those shown in the section "Measurement of inhibitory activity against EGFR (d746-750/T790M/C797S) kinase." However, among the materials, the kinase protein used was a purified recombinant human EGFR (WT) purchased from Carna Biosciences Inc., Japan. In the measurement procedures, the final concentration of ATP was set to 1.5 µM. Finally, data analysis was conducted to determine the IC50 value (nM) of each compound against EGFR (WT).

Moreover, as control compounds, the above Comparative Example A (Example 3 in WO20131118817) and Comparative Example B (Example 35 in WO2013/118817) known to have EGFR inhibitory activity were used.

The measured data are shown in Table 6 below.

TABLE 6

| | EGFR (WT) IC50 value (nM) |
|---|---|
| Example1 | 2.1 |
| Example2 | 0.52 |
| Example3 | 0.45 |
| Example4 | 2.9 |
| Example5 | 4.0 |
| Example6 | 5.2 |
| Example7 | 2.5 |
| Example8 | 3.2 |
| Example9 | 2.6 |
| Example10 | 1.1 |
| Example11 | 11 |
| Example12 | 2.1 |
| Example13 | 0.61 |
| Example14 | 1.7 |
| Example15 | 1.5 |
| Example16 | 0.53 |
| Example17 | 2.6 |
| Example18 | 1.4 |
| Example19 | 0.39 |
| Example20 | 2.1 |
| Example21 | 1.7 |
| Example22 | 0.55 |
| Example23 | 1.4 |
| Example24 | 0.73 |
| Example25 | 0.51 |
| Example26 | 2.1 |
| Example27 | 2.4 |
| Example28 | 3.2 |
| Example29 | 0.62 |
| Example30 | 1.9 |
| Example31 | 1.5 |
| Example32 | 1.0 |
| Example33 | 1.9 |
| Example34 | 0.84 |
| Example35 | 1.3 |
| Example36 | 2.6 |
| Example37 | 0.92 |
| Example38 | 1.6 |
| Example39 | 1.5 |
| Example40 | 5.0 |
| Example41 | 2.1 |
| Example42 | 0.31 |
| Example43 | 1.7 |
| Example44 | 0.80 |
| Example45 | 1.9 |
| Example46 | 0.79 |
| Example47 | 0.41 |
| Example48 | 0.75 |
| Example49 | 0.86 |
| Example50 | 1.2 |
| Example51 | 0.94 |
| Example52 | 0.88 |
| Example53 | 1.9 |
| Example54 | 6.3 |
| Example55 | 1.2 |
| Example56 | 0.94 |
| Example57 | 5.9 |
| Example58 | 3.9 |
| Comparative Example A | 1.6 |
| Comparative Example B | 0.95 |

As can be seen from the results of 1) to 5) in Test Example 1, the compounds of the present invention were confirmed to have strong inhibitory activity not only against EGFR (d746-750/C797S) and EGFR (L858R/C797S) but also against EGFR (d746-750/T790M/C797S) and EGFR (L858R/T790M/C797S), when compared to the known compounds. Moreover, a comparison with Comparative Examples A and B indicated that the inhibitory activity was greatly affected by the presence of an alkyne at the 6-position and a bicyclo ring structure at the 7-position. Such a substituent -induced difference in activity not been elucidated at all, and is therefore a surprising finding.

Test Example 2

Test for inhibitory activity against the growth of cell lines expressing wild-type and mutated EGFRs (in vitro)

(1) Mouse cell line Ba/F3-EGFR (d746-750/T790M/C797S) transfected with and stably expressing EGFR (d746-750/T790M/C797S), mouse cell Ba/F3-EGFR (L858R/T790M/C797S) transfected with and stably expressing EGFR (L858R/T790M/C797S), and mouse cell line Ba/F3-EGFR (WT) transfected with and stably expressing wild-type EGFR were each suspended in RPMI-1640 cell culture medium (RPMI-1640, 10% FBS, 100 unit/ml penicillin, 0.1 mg/ml streptomycin). In the case of the mouse cell line Ba/F3-EGFR (WT), RPMI-1640 cell culture medium containing EGF at a final concentration of 50 ng/ml was used to suspend this cell line. It should be noted that the mouse cell line Ba/F3-EGFR (d746-750/T790M/C797S) transfected with and stably expressing EGFR (d746-750/T790M/C797S), the mouse cell line Ba/F3-EGFR (L858R/T790M/C797S) transfected with and stably expressing EGFR (L858R/T790M/C797S) and the mouse cell line Ba/F3-EGFR (WT) transfected with and stably expressing wild-type EGFR were prepared by using nucleotide sequences encoding the proteins of SEQ ID NOs: 1 and 2 in accordance with Test Example 1 in WO2018/079310, These cell suspensions were seeded in wells of 96-well flat-bottomed plates. The compounds of the present invention were dissolved in DMSO, and serial dilutions of these test compounds were prepared with DMSO (1000-fold of the final concentration). Each test compound solution in DMSO or DMSO alone was diluted with RPMI-1640 cell culture medium for each cell line, and this dilution was added to wells of the cell culture plate such that the final concentration of DMSO was 0.1%, followed by culture at 37° C. for 3 days in a 5% carbon dioxide gas-containing incubator. Before and after addition of each test compound solution in DMSO, the number of cells was counted using the CellTiter-Glo® system (Promega) on the basis of the protocol recommended by Promega.

In each cell line, the rate of cell growth inhibition was calculated according to the equation shown below in wells to which each test compound was added at different concentrations. Moreover, the inhibition rate at each concentration was plotted for each test compound, and the concentration of each test compound required to give 50% cell survival rate, i.e., IC50 (nM) was determined by curve fitting software XLfit (IDBS).

Cell survival rate (%)=T/C×100

T: emission intensity in a well cultured for 3 days after addition of a test compound solution C: emission intensity in a well cultured for 3 days after addition of DMSO Moreover, as control compounds, the above Comparative Example A (Example 3 in WO2013/118817) and Comparative Example B (Example 35 in WO2013/118817) known to have EGFR inhibitory activity were used.

These results are shown in Table 7 below.

The compounds of the present invention showed a weak growth inhibitory effect against: the cell line expressing wild-type EGFR. In contrast, the compounds of the present invention were found to have a strong growth inhibitory effect against the cell line expressing EGFR (d746-750/T790M/C797S) and the cell line expressing EGFR (L858R/T790M/C797S). These results indicated that the compounds of the present invention selectively exerted a growth inhibitory effect against the cell lines expressing mutated EGFRs.

Test Example 3

Test for inhibitory effect against the activity of various EGFR kinases (in vitro)

1) Measurement of inhibitory activity against EGFR (d746-750/T790M/C797S) kinase In accordance with the same procedures as shown in 1) in Test Example 1, the compounds of the above examples were measured for their inhibitory activity against EGFR (d746-750/T790M/C797S) kinase activity. The measured data are shown in Table 8 below.

TABLE 8

| | EGFR (d746-750/T790M/C797S) IC50 value (nM) |
|---|---|
| Example 59 | 0.37 |
| Example 60 | <0.3 |
| Example 61 | <0.3 |
| Example 62 | <0.3 |
| Example 63 | <0.3 |
| Example 64 | <0.3 |
| Example 65 | <0.3 |
| Example 66 | <0.3 |
| Example 67 | <0.3 |
| Example 68 | <0.3 |
| Example 69 | <0.3 |
| Example 70 | <0.3 |

2) Measmement of inhibitory activity against EGFR (L858R/T790M/C797S) kinase

In accordance with the same procedures as shown in 2) in Test Example 1, the compounds of the present invention were measured for their inhibitory activity against EGFR (L858R/T790M/C797S) kinase activity. The measured data are shown in Table 9 below.

TABLE 7

| | BaF3_EGFR (d746-750/T790M/C797S) IC50 value (nM) | BaF3_EGFR (L858R/T790M/C797S) IC50 value (nM) | BaF3_EGFR (WT) IC50 value (nM) |
|---|---|---|---|
| Example2 | 20 | 185 | 2646 |
| Example3 | 56 | 529 | 3330 |
| Example13 | 239 | 910 | 3596 |
| Example14 | 204 | 952 | 3500 |
| Example24 | 34 | 403 | 3790 |
| Example37 | 21 | 270 | 2972 |
| Example43 | 57 | 417 | 3287 |
| Example45 | 42 | 305 | 3397 |
| Example46 | 19 | 204 | 2412 |
| Example48 | 24 | 223 | 2487 |
| Example49 | 19 | 290 | 3072 |
| Comparative ExampleA | 3658 | 2258 | 2462 |
| Comparative ExampleB | 1075 | 3586 | 1046 |

TABLE 9

|  | EGFR (L858R/T790M/C797S) IC50 value (nM) |
|---|---|
| Example 59 | 0.47 |
| Example 60 | <0.3 |
| Example 61 | 1.6 |
| Example 62 | <0.3 |
| Example 63 | <0.3 |
| Example 64 | <0.3 |
| Example 65 | <0.3 |
| Example 66 | <0.3 |
| Example 67 | <0.3 |
| Example 68 | <0.3 |
| Example 69 | <0.3 |
| Example 70 | <0.3 |

3) Measurement of inhibitory activity aaainst EGFR (d746-750/C797S) kinase

In accordance with the same procedures as shown in 3) in Test Example 1, the compounds of the present invention were measured for their inhibitory activity against EGFR (d746-750/C797S) kinase activity. The measured data are shown in Table 10 below.

TABLE 10

|  | EGFR (d746-750/C797S) IC50 value (nM) |
|---|---|
| Example 59 | 0.83 |
| Example 60 | 0.30 |
| Example 61 | 0.54 |
| Example 62 | 0.34 |
| Example 63 | 0.51 |
| Example 64 | 0.86 |
| Example 65 | 0.40 |
| Example 66 | <0.3 |
| Example 67 | 0.30 |
| Example 68 | <0.3 |
| Example 69 | <0.3 |
| Example 70 | 0.70 |

4) Measurement of inhibitory activity against EGFR (L858R/C797S) kinase

In accordance with the same procedures as shown in 4) in Test Example 1, the compounds of the present invention were measured for their inhibitor activity against. EGFR (L858R/C797S) kinase activity. The measured data are shown in Table 11 below.

TABLE 11

|  | EGFR (L858R/C797S) IC50 value (nM) |
|---|---|
| Example 59 | 1.7 |
| Example 60 | 0.48 |
| Example 61 | 1.1 |
| Example 64 | 0.32 |
| Example 65 | <0.3 |
| Example 66 | <0.3 |
| Example 67 | 0.37 |
| Example 68 | 0.36 |
| Example 69 | 0.59 |
| Example 70 | 1.6 |

5) EGFR (WT)

In accordance with the same procedures as shown in 5) in Test Example 1, the compounds of the present invention were measured for their inhibitory activity against. EGFR (WT) kinase activity. The measured data are shown in Table 12 below.

TABLE 12

|  | EGFR (WT) IC50 value (nM) |
|---|---|
| Example 59 | 2.2 |
| Example 60 | 0.72 |
| Example 61 | 2.7 |
| Example 62 | 1.6 |
| Example 63 | 2.8 |
| Example 64 | 0.41 |
| Example 65 | <0.3 |
| Example 66 | <0.3 |
| Example 67 | 0.35 |
| Example 68 | 0.43 |
| Example 69 | 0.74 |
| Example 70 | 0.94 |

As can be seen from the results of 1) to 5) in Test Example 2, the compounds of the present invention were confirmed to have strong inhibitory activity not only against EGFR (d746-750/C797S) and EGFR (L858R/C797S) but also against EGFR (d746-750/T790M/C797S) and EGFR (L858R/T790M/C797S).

Test Example 4

Test for inhibitory activity against the growth of cell lines expressing wild-type and mutated EGFRs (in vitro)

In accordance with the same procedures as shown in Test Example 2, the compounds of the present invention were tested for their inhibitory activity against the growth of the cell hoes expressing wild-type and mutated EGFRs. The measured data are shown in Table 13 below.

TABLE 13

|  | BaF3_EGFR (d746-750/T790M/C797S) IC50 value (nM) | BaF3_EGFR (L858R/T790M/C797S) IC50 value (nM) | BaF3_EGFR (WT) IC50 value (nM) |
|---|---|---|---|
| Example 1 | 98 | 887 | 3485 |
| Example 9 | 59 | 592 | >2000 |
| Example 16 | 32 | 283 | 1922 |
| Example 18 | 124 | 1268 | 2475 |
| Example 20 | 31 | 245 | 2652 |
| Example 23 | 31 | 649 | 3189 |
| Example 27 | 110 | 754 | >2000 |
| Example 35 | 44 | 348 | 2957 |
| Example 36 | 59 | 448 | >2000 |
| Example 39 | 98 | 658 | 2362 |

TABLE 13-continued

| | BaF3_EGFR (d746-750/T790M/C797S) IC50 value (nM) | BaF3_EGFR (L858R/T790M/C797S) IC50 value (nM) | BaF3_EGFR (WT) IC50 value (nM) |
|---|---|---|---|
| Example 41 | 102 | 843 | 3244 |
| Example 44 | 30 | 268 | 2264 |
| Example 47 | 33 | 382 | 2064 |
| Example 53 | 162 | 978 | 3289 |
| Example 63 | 73 | 672 | 2994 |

The compounds of the present invention showed a weak growth inhibitory effect against the cell line expressing wild-type EGFR. In contrast, the compounds of the present invention were found to have a strong growth inhibitory effect against the cell line expressing EGFR (d746-750/T790M/C797S) and the cell line expressing. EGFR (L858R/T790M/C797S). These results indicated that the compounds of the present invention selectively exerted a growth inhibitory effect against the cell lines expressing mutated EGFRs.

```
EGFR d746-750/T790M/C797S
                                (SEQ ID NO: 1)
MSPILGYWKIKGLVQPTRLLLEYLEEKYEEHLYER

DEGDKWRNKKFELGLEFPNLPYYIDGDVKLTQSMA

IIRYIADKHNMLGGCPKERAEISMLEGAVLDIRYG

VSRIAYSKDFETLKVDFLSKLPEMLKMFEDRLCHK

TYLNGDHVTITPDFMLYDALDVVLYMDPMCLDAFP

KLVCFKKRIEAIPQIDKYLKSSKYIAWPLQGWQAT

FGGGDHPPKSDGSRRRHIVRKRTLRRLLQERELVE

PLTPSGEAPNQALLRILKETEFKKIKVLGSGAFGT

VYKGLWIPEGEKVKIPVAIKTSPKANKEILDEAYV

MASVDNPHVCRLLGICLTSTVQLIMQLMPFGSLLD

YVREHKDNIGSQYLLNWCVQIAKGMNYLEDRRLVI

IRDLAARNVLVKTPQHVKITDFGLAKLLGAEEKEY

HAEGGKVPIKWMALESILHRIYTHQSDVWSYGVTV

WELMTFGSKPYDGIPASEISSILEKGERLPQPPIC

TIDVYMIMVKCWMIDADSRPKFRELIIEFSKMARD

PQRYLVIQGDERMHLPSPTDSNFYRALIVEDEEDT

VEDDVVDADEYLIPQQGFFSSPSTSRTPLLSSLSA

TSNNSTVACIDRNGLQSCPIKEDSFLQRYSSDPTG

ALTEDSIDDTFLPVPEYINQSVPKRPAGSVQNPVY

HNQPLNPAPSRDPHYQDPHSTAVGNPEYLNTVQPT

CVNSTFDSPAHWAQKGSHQISLDNPDYQQDFFPKE

AKPNGIFKGSTAENAEYLRVAPQSSEFIGA

EGFR L858R/T790M/C797S
                                (SEQ ID NO: 2)
MSPILGYWKIKGLVQPTRLLLEYLEEKYEEHLYER

DEGDKWRNKKFELGLEFPNLPYYIDGDVKLTQSMA

IIRYIADKHNIVILGGCPKERAEISMLEGAVLDIR

YGVSRIAYSKDFETLKVDFLSKLPEMLKMFEDRLC

HKTYLNGDHVTITPDFMLYDALDVVLYMDPMCLDA

FPKLVCFKKRIEAIPQIDKYLKSSKYIAWPLQGWQ

ATFGGGDHPPKSDGSRRRHIVRKRTLRRLLQEREL

VEPLTPSGEAPNQALLRILKETEFKKIKVLGSGAF

GTVYKGLWIPEGEKVKIPVAIKELREATSPKANKE

ILDEAYVMASVDNPHVCRLLGICLTSTVQLIMQLM

PFGSLLDYVREHKDNIGSQYLLNWCVQIAKGMNYL

EDRRLVEIRDLAARNVLVKTPQHVKITDFGRAKLL

GAEEKEYHAEGGKVPIKWMALESILEIRIYTHQSD

VWSYGVTVWELMTFGSKPYDGIPASEISSILEKGE

RLPQPPICTIDVYMIMVKCWMIDADSRPKFRELII

EFSKMARDPQRYLVIQGDERMHLPSPTDSNFYRAL

MDEEDMDDVVDADEYLIPQQGFFSSPSTSRTPLLS

SLSATSNNSTVACIDRNGLQSCPIKEDSFLQRYSS

DPTGALTEDSIDDTFLPVPEYINQSVPKRPAGSVQ

NPVYHNQPLNPAPSRDPHYQDPHSTAVGNPEYLNT

VQPTCVNSTFDSPAHWAQKGSHQISLDNPDYQQDF

FPKEAKPNGIFKGSTAENAEYLRVAPQSSEFIGA
```

The invention claimed is:
1. A compound represented by formula (I):

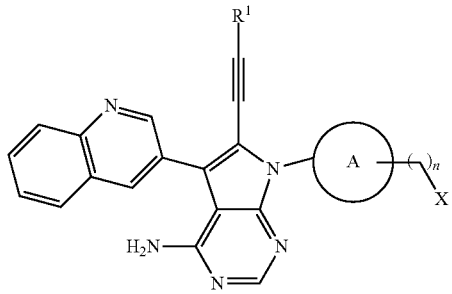

(I)

or a pharmaceutically acceptable salt thereof,
wherein:
ring A is bicyclo[2.2.1]heptanyl or bicyclo[2.2.2]octanyl;
$R^1$ is H or $C_1$-$C_3$ alkyl;
wherein the $C_1$-$C_3$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl; and
wherein each heterocyclyl substituent of the $C_1$-$C_3$ alkyl is independently saturated or unsaturated;
X is $NR^2R^3$, $OR^4$, monocyclic heterocyclyl, or polycyclic heterocyclyl;
wherein the monocyclic heterocyclyl or polycyclic heterocyclyl is saturated or unsaturated;
wherein the monocyclic heterocyclyl or polycyclic heterocyclyl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl; and
wherein each heterocyclyl substituent of the monocyclic heterocyclyl or polycyclic heterocyclyl is independently saturated or unsaturated;
$R^2$ is H or $C_1$-$C_6$ alkyl;
wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl; and
wherein each heterocyclyl substituent of the $C_1$-$C_6$ alkyl is independently saturated or unsaturated;
$R^3$ is H, $C_1$-$C_6$ alkyl, C(O)$R^5$, C(S)$R^6$, S(O)$_2R^7$, or $C_3$-$C_7$ cycloalkyl;
wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl;
wherein the $C_3$-$C_7$ cycloalkyl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl; and
wherein each heterocyclyl substituent of the $C_1$-$C_6$ alkyl or $C_3$-$C_7$ cycloalkyl is independently saturated or unsaturated;
$R^4$ is H, $C_1$-$C_6$ alkyl, C(O)$NH_2$, or C3-C7 cycloalkyl;
wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl;
wherein the $NH_2$ of C(O)NH2 is optionally substituted with 1 or 2 substituents independently selected from the group consisting of alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), $OCH_2F$, S(O)$_2CH_3$, cycloalkyl, heterocyclyl, and aryl;
wherein the $C_3$-$C_7$ cycloalkyl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, and aryl; and
wherein each heterocyclyl substituent of the $C_1$-$C_6$ alkyl, NH2 of C(O)$NH_2$, or $C_3$-$C_7$ cycloalkyl is independently saturated or unsaturated;
$R^5$ is $C_1$-$C_6$ alkyl, $NH_2$, $OC_1$-$C_6$ alkyl, $C_3$-$C_7$ cycloalkyl, monocyclic 4- to 10-membered heterocyclyl, polycyclic 4- to 10 membered heterocyclyl, monocyclic 5- to 10-membered heterocyclyl, polycyclic 5- to 10 membered heterocyclyl, monocyclic 6- to 10-membered aryl, or polycyclic 6- to 10-membered aryl;
wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl;
wherein the $NH_2$ is optionally substituted with 1 or 2 substituents independently selected from the group consisting of alkyl, haloalkyl, alkyl-$NH_2$, alkyl-NH(alkyl), alkyl-N(alkyl)$_2$, alkyl-OH, alkyl -O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), $OCH_2F$, S(O)$_2CH_3$, cycloalkyl, heterocyclyl, and aryl;
wherein the $OC_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), $OCH_2F$, =O, P(O)(R)$_2$, S(O)$_2CH_3$, cycloalkyl, heterocyclyl, and aryl;
wherein the $C_3$-$C_7$ cycloalkyl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 4- to 10-membered heterocyclyl or polycyclic 4- to 10-membered heterocyclyl is saturated;

wherein the monocyclic 4- to 10-membered heterocyclyl or polycyclic 4- to 10-membered heterocyclyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 5- to 10-membered heterocyclyl or polycyclic 5- to 10-membered heterocyclyl is unsaturated;

wherein the monocyclic 5- to 10-membered heterocyclyl or polycyclic 5- to 10-membered heterocyclyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 6- to 10-membered aryl or polycyclic 6- to 10-membered aryl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl; and wherein each heterocyclyl substituent of the C$_1$-C$_6$ alkyl, NH$_2$, OC$_1$-C$_6$ alkyl, C$_3$-C$_7$ cycloalkyl, monocyclic 4- to 10-membered heterocyclyl, polycyclic 4- to 10-membered heterocyclyl, monocyclic 5- to 10-membered heterocyclyl, polycyclic 5- to 10-membered heterocyclyl, monocyclic 6- to 10-membered aryl, or polycyclic 6- to 10-membered aryl is independently saturated or unsaturated;

R$^6$ is H, C$_1$-C$_6$ alkyl, NHC$_1$-C$_6$ alkyl, N(C$_1$-C$_6$ alkyl)$_2$, C$_3$-C$_7$ cycloalkyl, monocyclic 4- to 10-membered heterocyclyl, or polycyclic 4- to 10 membered heterocyclyl;

wherein the C$_1$-C$_6$ alkyl is optionally substituted with 1, 2, or 3 substituents independently selected from the group consisting of halogen, CN, NO$_2$, C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the C$_1$-C$_6$ alkyl of the NHC$_1$-C$_6$ alkyl or N(C$_1$-C$_6$ alkyl)2 is optionally substituted with 1, 2, or 3 substituents independently selected from the group consisting of halogen, CN, NO$_2$, C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the C$_3$-C$_7$ cycloalkyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 4- to 10-membered heterocyclyl or polycyclic 4- to 10-membered heterocyclyl is saturated;

wherein the monocyclic 4- to 10-membered heterocyclyl or polycyclic 4- to 10-membered heterocyclyl contains 1, 2, 3, or 4 heteroatoms or heteroatomic groups independently selected from the group consisting of N, NH, O, and S;

wherein the monocyclic 4- to 10-membered heterocyclyl or polycyclic 4- to 10-membered heterocyclyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl -OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl; and wherein each heterocyclyl substituent of the C$_1$-C$_6$ alkyl, C$_1$-C$_6$ alkyl of NHC$_1$-C$_6$ alkyl, C$_1$-C$_6$ alkyl of N(C$_1$-C$_6$ alkyl)$_2$, C$_3$-C$_7$ cycloalkyl, monocyclic 4- to 10-membered heterocyclyl, or polycyclic 4- to 10-membered heterocyclyl is independently saturated or unsaturated;

R$^7$ is C$_1$-C$_6$ alkyl, C$_3$-C$_7$ cycloalkyl, 5- to 10 membered heterocyclyl, or 6- to 10-membered aryl;

wherein the C$_1$-C$_6$ alkyl is optionally substituted with 1, 2, or 3 substituents independently selected from the group consisting of halogen, CN, NO$_2$, C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the C$_3$-C$_7$ cycloalkyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the 5- to 10-membered heterocyclyl is saturated or unsaturated;

wherein the 5- to 10-membered heterocyclyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the 6- to 10-membered aryl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl-OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl; and wherein each heterocyclyl substituent of the $C_1$-$C_6$ alkyl, $C_3$-$C_7$ cycloalkyl, 5- to 10-membered heterocyclyl, or 6- to 10-membered aryl is independently saturated or unsaturated;

each R is independently halogen, alkyl, or aryl; and n is 0, 1, 2, or 3.

2. The compound of claim 1, or a pharmaceutically acceptable salt thereof, wherein ring A is bicyclo[2.2.1]heptanyl.

3. The compound of claim 1, or a pharmaceutically acceptable salt thereof, wherein $R^1$ is H or $C_1$-$C_3$ alkyl.

4. The compound of claim 1, or a pharmaceutically acceptable salt thereof, wherein $R^1$ is H.

5. The compound of claim 1, or a pharmaceutically acceptable salt thereof, wherein the optional substituents for X are independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), =O, cycloalkyl, heterocyclyl, and aryl.

6. The compound of claim 1, or a pharmaceutically acceptable salt thereof, wherein n is 0 or 1.

7. The compound of claim 1, or a pharmaceutically acceptable salt thereof, wherein n is 0.

8. The compound of claim 1, or a pharmaceutically acceptable salt thereof, wherein:

X is $NR^2R^3$ or a monocyclic 5- to 7-membered heterocyclyl;

wherein the monocyclic 5- to 7-membered heterocyclyl is saturated or unsaturated; and wherein the monocyclic 5- to 7-membered heterocyclyl contains 1, 2, or 3 heteroatoms or heteroatomic groups independently selected from the group consisting of N, NH, O, and S;

$R^2$ is H or $C_1$-$C_6$ alkyl;

$R^3$ is $C_1$-$C_6$ alkyl, C(O)$R^5$, or C(S)$R^6$;

wherein the $C_1$-$C_6$ alkyl is optionally substituted with 1, 2, or 3 substituents independently selected from the group consisting of halogen, CN, and a monocyclic 5- to 7-membered heterocyclyl;

wherein each monocyclic 5- to 7-membered heterocyclyl substituent of the $C_1$-$C_6$ alkyl independently contains 1, 2, or 3 heteroatoms or heteroatomic groups independently selected from the group consisting of N, NH, O, and S; and wherein each monocyclic 5- to 7-membered heterocyclyl substituent of the $C_1$-$C_6$ alkyl is independently unsaturated; and $R^4$ is H;

$R^5$ is $C_1$-$C_6$ alkyl, NH$C_1$-$C_6$ alkyl, N($C_1$-$C_6$ alkyl)$_2$, OC$C_1$-$C_6$ alkyl, monocyclic 5- to 10-membered heterocyclyl, polycyclic 5- to 10 membered heterocyclyl, monocyclic 6- to 10-membered aryl, or polycyclic 6- to 10-membered aryl;

wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 5- to 10-membered heterocyclyl or polycyclic 5- to 10-membered heterocyclyl is unsaturated;

wherein the monocyclic 5- to 10-membered heterocyclyl or polycyclic 5- to 10-membered heterocyclyl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl -OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 6- to 10-membered aryl or polycyclic 6- to 10-membered aryl is optionally substituted with 1, 2, or 3 substituents independently selected from the group consisting of halogen, CN, $NO_2$, alkyl, haloalkyl, alkyl-$NH_2$, alkyl-NH(alkyl), alkyl-N(alkyl)$_2$, alkyl-OH, alkyl-O(alkyl), alkyl(heterocyclyl), alkyl(aryl), C(O)$NH_2$, C(O)OH, C(O)O(alkyl), $NH_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl; and wherein each heterocyclyl substituent of the $C_1$-$C_6$ alkyl, monocyclic 5- to 10-membered heterocyclyl, polycyclic 5- to 10-membered heterocyclyl, monocyclic 6- to 10-membered aryl, or polycyclic 6- to 10-membered aryl is independently saturated or unsaturated; and $R^6$ is NH$C_1$-$C_6$ alkyl, N($C_1$-$C_6$ alkyl)$_2$, monocyclic 4- to 10-membered heterocyclyl, or polycyclic 4- to 10 membered heterocyclyl;

wherein the monocyclic 4- to 10-membered heterocyclyl or polycyclic 4- to 10-membered heterocyclyl is saturated;

wherein the monocyclic 4- to 10-membered heterocyclyl or polycyclic 4- to 10-membered heterocyclyl contains 1, 2, 3, or 4 heteroatoms or heteroatomic groups independently selected from the group consisting of N, NH, O, and S; and wherein the monocyclic 4- to 10-membered heterocyclyl or polycyclic 4- to 10-membered heterocyclyl is optionally substituted with 1, 2, or 3 independently selected $C_1$-$C_6$ alkyl substituents.

9. The compound of claim 1, or a pharmaceutically acceptable salt thereof, wherein:

X is $NR^2R^3$ or a monocyclic 5- to 7-membered heterocyclyl;

wherein the monocyclic 5- to 7-membered heterocyclyl is saturated or unsaturated; and wherein the monocyclic 5- to 7-membered heterocyclyl contains 1, 2, or 3 heteroatoms or heteroatomic groups independently selected from the group consisting of N, NH, O, and S;

$R^2$ is H;

$R^3$ is C(O)$R^5$; and $R^5$ is $C_1$-$C_6$ alkyl, NH$C_1$-$C_6$ alkyl, N($C_1$-$C_6$ alkyl)$_2$, O$C_1$-$C_6$ alkyl, monocyclic 5- to 10-membered heterocyclyl, polycyclic 5- to 10 membered heterocyclyl, monocyclic 6- to 10-membered aryl, or polycyclic 6- to 10-membered aryl;

wherein the $C_1$-$C_6$ alkyl is optionally substituted with 1, 2, or 3 substituents independently selected from the group consisting of halogen, CN, $NO_2$, C(O)$NH_2$, C(O)OH, C(O)O(alkyl), $NH_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl;

wherein the monocyclic 5- to 10-membered heterocyclyl or polycyclic 5- to 10-membered heterocyclyl is unsaturated;

wherein the monocyclic 5- to 10-membered heterocyclyl or polycyclic 5- to 10-membered heterocyclyl is optionally substituted with 1, 2, or 3 substituents independently selected from the group consisting of halogen, CN, NO$_2$, alkyl, haloalkyl, alkyl-NH$_2$, alkyl-NH(alkyl), alkyl-N(alkyl)$_2$, alkyl -OH, alkyl-O(alkyl), alkyl(heterocyclyl), alkyl(aryl), C(O)NH$_2$, C(O)OH, C(O)O(alkyl), NH$_2$, NH(alkyl), N(alkyl)$_2$, OH, O(alkyl), OCH$_2$F, =O, P(O)(R)$_2$, S(O)$_2$CH$_3$, cycloalkyl, heterocyclyl, and aryl; and wherein each heterocyclyl substituent of the C$_1$-C$_6$ alkyl, monocyclic 5- to 10-membered heterocyclyl, or polycyclic 5- to 10-membered heterocyclyl is independently saturated or unsaturated.

10. The compound of claim 1, or a pharmaceutically acceptable salt thereof, wherein:
X is NR$^2$R$^3$ or a monocyclic 5- to 7-membered heterocyclyl;
  wherein the monocyclic 5- to 7-membered heterocyclyl is saturated; and
  wherein the monocyclic 5- to 7-membered heterocyclyl contains 1, 2, or 3 heteroatoms or heteroatomic groups independently selected from the group consisting of N, NH, O, and S;
R$^2$ is H;
R$^3$ is C(O)R$^5$; and
R$^5$ is C$_1$-C$_6$ alkyl, monocyclic 5- to 10-membered heterocyclyl, or polycyclic 5- to 10 membered heterocyclyl;
  wherein the C$_1$-C$_6$ alkyl is optionally substituted with 1, 2, or 3 independently selected halogen substituents;
  wherein the monocyclic 5- to 10-membered heterocyclyl or polycyclic 5- to 10-membered heterocyclyl is partially unsaturated or fully unsaturated;
  wherein the monocyclic 5- to 10-membered heterocyclyl or polycyclic 5- to 10-membered heterocyclyl contains 1, 2, 3, or 4 heteroatoms or heteroatomic groups independently selected from the group consisting of N, NH, O, and S; and
  wherein the monocyclic 5- to 10-membered heterocyclyl or polycyclic 5- to 10-membered heterocyclyl is optionally substituted with 1, 2, or 3 independently selected C$_1$-C$_6$ alkyl substituents.

11. A pharmaceutical composition comprising a pharmaceutically acceptable carrier and a compound of claim 1, or a pharmaceutically acceptable salt thereof.

12. A method for inhibiting epidermal growth factor receptor activity in a subject, wherein the method comprises administering to the subject in need thereof a therapeutically effective amount of a compound of claim 1, or a pharmaceutically acceptable salt thereof.

13. A method for treating a tumor in a subject, wherein the method comprises administering to the subject in need thereof a therapeutically effective amount of a compound of claim 1, or a pharmaceutically acceptable salt thereof.

14. A compound selected from the group consisting of:

(1)

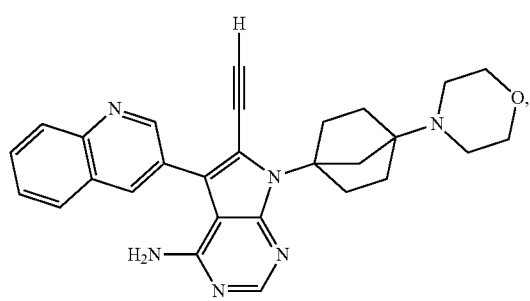

-continued (2)

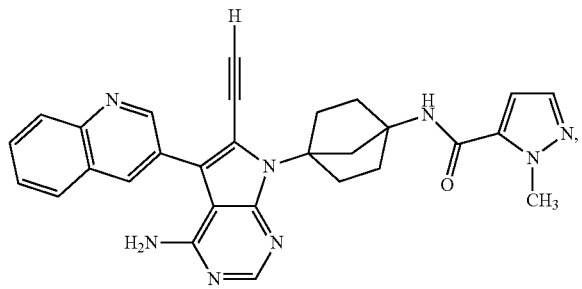

(3)

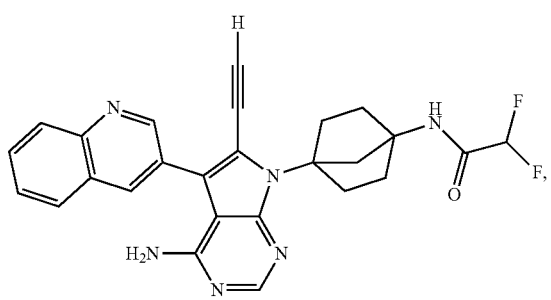

(4)

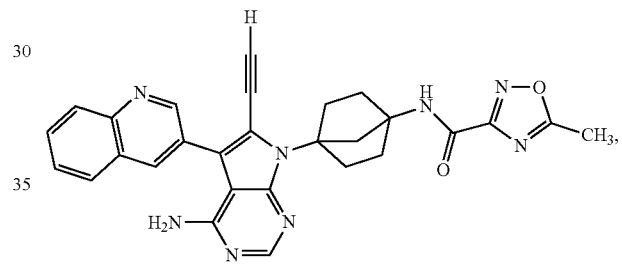

(5)

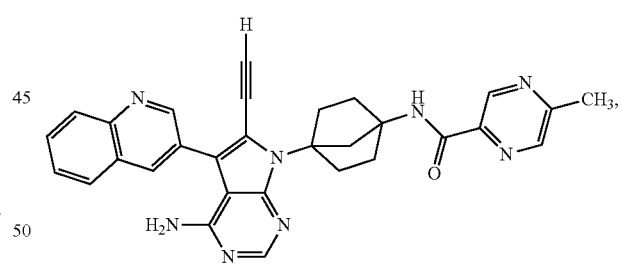

(6)

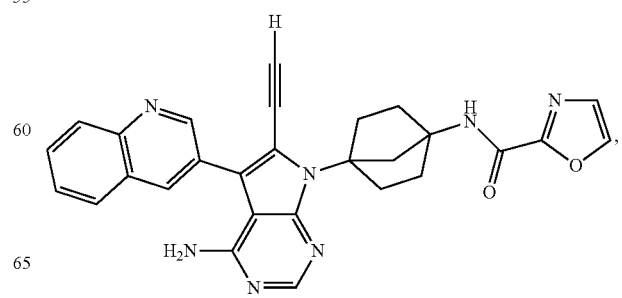

(7)
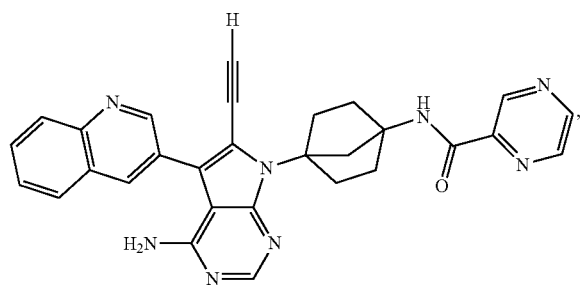
(8)
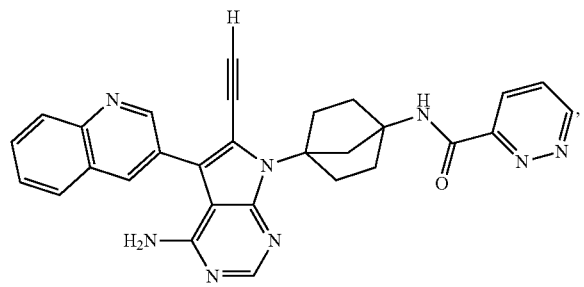
(9)
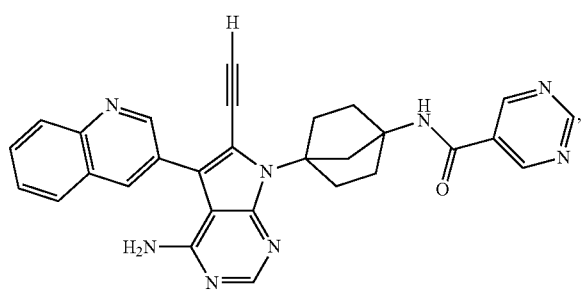
(10)
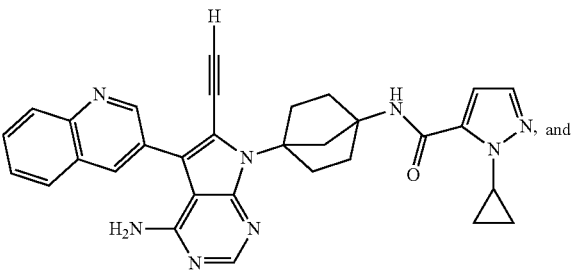
(11)
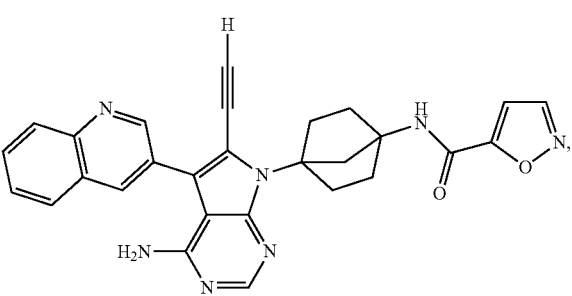
or a pharmaceutically acceptable salt thereof.
* * * * *

SEQUENCE LISTING

```
<160> NUMBER OF SEQ ID NOS: 2

<210> SEQ ID NO 1
<211> LENGTH: 759
<212> TYPE: PRT
<213> ORGANISM: Artificial
<220> FEATURE:
<223> OTHER INFORMATION: Synthetic Protein
```

-continued

```
<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Arg Arg
    210                 215                 220

Arg His Ile Val Arg Lys Arg Thr Leu Arg Arg Leu Leu Gln Glu Arg
225                 230                 235                 240

Glu Leu Val Glu Pro Leu Thr Pro Ser Gly Glu Ala Pro Asn Gln Ala
                245                 250                 255

Leu Leu Arg Ile Leu Lys Glu Thr Glu Phe Lys Lys Ile Lys Val Leu
            260                 265                 270

Gly Ser Gly Ala Phe Gly Thr Val Tyr Lys Gly Leu Trp Ile Pro Glu
        275                 280                 285

Gly Glu Lys Val Lys Ile Pro Val Ala Ile Lys Thr Ser Pro Lys Ala
    290                 295                 300

Asn Lys Glu Ile Leu Asp Glu Ala Tyr Val Met Ala Ser Val Asp Asn
305                 310                 315                 320

Pro His Val Cys Arg Leu Leu Gly Ile Cys Leu Thr Ser Thr Val Gln
                325                 330                 335

Leu Ile Met Gln Leu Met Pro Phe Gly Ser Leu Leu Asp Tyr Val Arg
            340                 345                 350

Glu His Lys Asp Asn Ile Gly Ser Gln Tyr Leu Leu Asn Trp Cys Val
        355                 360                 365

Gln Ile Ala Lys Gly Met Asn Tyr Leu Glu Asp Arg Arg Leu Val His
    370                 375                 380

Arg Asp Leu Ala Ala Arg Asn Val Leu Val Lys Thr Pro Gln His Val
385                 390                 395                 400

Lys Ile Thr Asp Phe Gly Leu Ala Lys Leu Leu Gly Ala Glu Glu Lys
```

```
            405                 410                 415
Glu Tyr His Ala Glu Gly Gly Lys Val Pro Ile Lys Trp Met Ala Leu
            420                 425                 430

Glu Ser Ile Leu His Arg Ile Tyr Thr His Gln Ser Asp Val Trp Ser
        435                 440                 445

Tyr Gly Val Thr Val Trp Glu Leu Met Thr Phe Gly Ser Lys Pro Tyr
    450                 455                 460

Asp Gly Ile Pro Ala Ser Glu Ile Ser Ser Ile Leu Glu Lys Gly Glu
465                 470                 475                 480

Arg Leu Pro Gln Pro Pro Ile Cys Thr Ile Asp Val Tyr Met Ile Met
            485                 490                 495

Val Lys Cys Trp Met Ile Asp Ala Asp Ser Arg Pro Lys Phe Arg Glu
            500                 505                 510

Leu Ile Ile Glu Phe Ser Lys Met Ala Arg Asp Pro Gln Arg Tyr Leu
            515                 520                 525

Val Ile Gln Gly Asp Glu Arg Met His Leu Pro Ser Pro Thr Asp Ser
        530                 535                 540

Asn Phe Tyr Arg Ala Leu Met Asp Glu Glu Asp Met Asp Asp Val Val
545                 550                 555                 560

Asp Ala Asp Glu Tyr Leu Ile Pro Gln Gln Gly Phe Phe Ser Ser Pro
                565                 570                 575

Ser Thr Ser Arg Thr Pro Leu Leu Ser Ser Leu Ser Ala Thr Ser Asn
            580                 585                 590

Asn Ser Thr Val Ala Cys Ile Asp Arg Asn Gly Leu Gln Ser Cys Pro
        595                 600                 605

Ile Lys Glu Asp Ser Phe Leu Gln Arg Tyr Ser Ser Asp Pro Thr Gly
    610                 615                 620

Ala Leu Thr Glu Asp Ser Ile Asp Asp Thr Phe Leu Pro Val Pro Glu
625                 630                 635                 640

Tyr Ile Asn Gln Ser Val Pro Lys Arg Pro Ala Gly Ser Val Gln Asn
                645                 650                 655

Pro Val Tyr His Asn Gln Pro Leu Asn Pro Ala Pro Ser Arg Asp Pro
            660                 665                 670

His Tyr Gln Asp Pro His Ser Thr Ala Val Gly Asn Pro Glu Tyr Leu
        675                 680                 685

Asn Thr Val Gln Pro Thr Cys Val Asn Ser Thr Phe Asp Ser Pro Ala
    690                 695                 700

His Trp Ala Gln Lys Gly Ser His Gln Ile Ser Leu Asp Asn Pro Asp
705                 710                 715                 720

Tyr Gln Gln Asp Phe Phe Pro Lys Glu Ala Lys Pro Asn Gly Ile Phe
                725                 730                 735

Lys Gly Ser Thr Ala Glu Asn Ala Glu Tyr Leu Arg Val Ala Pro Gln
            740                 745                 750

Ser Ser Glu Phe Ile Gly Ala
        755

<210> SEQ ID NO 2
<211> LENGTH: 764
<212> TYPE: PRT
<213> ORGANISM: Artificial
<220> FEATURE:
<223> OTHER INFORMATION: Synthetic Protein

<400> SEQUENCE: 2

Met Ser Pro Ile Leu Gly Tyr Trp Lys Ile Lys Gly Leu Val Gln Pro
```

-continued

```
1               5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
 50                 55                  60
Leu Thr Gln Ser Met Ala Ile Ile Arg Tyr Ile Ala Asp Lys His Asn
 65                 70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
                130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Gly Ser Arg Arg
                210                 215                 220
Arg His Ile Val Arg Lys Arg Thr Leu Arg Arg Leu Leu Gln Glu Arg
225                 230                 235                 240
Glu Leu Val Glu Pro Leu Thr Pro Ser Gly Glu Ala Pro Asn Gln Ala
                245                 250                 255
Leu Leu Arg Ile Leu Lys Glu Thr Glu Phe Lys Lys Ile Lys Val Leu
                260                 265                 270
Gly Ser Gly Ala Phe Gly Thr Val Tyr Lys Gly Leu Trp Ile Pro Glu
                275                 280                 285
Gly Glu Lys Val Lys Ile Pro Val Ala Ile Lys Glu Leu Arg Glu Ala
                290                 295                 300
Thr Ser Pro Lys Ala Asn Lys Glu Ile Leu Asp Glu Ala Tyr Val Met
305                 310                 315                 320
Ala Ser Val Asp Asn Pro His Val Cys Arg Leu Leu Gly Ile Cys Leu
                325                 330                 335
Thr Ser Thr Val Gln Leu Ile Met Gln Leu Met Pro Phe Gly Ser Leu
                340                 345                 350
Leu Asp Tyr Val Arg Glu His Lys Asp Asn Ile Gly Ser Gln Tyr Leu
                355                 360                 365
Leu Asn Trp Cys Val Gln Ile Ala Lys Gly Met Asn Tyr Leu Glu Asp
                370                 375                 380
Arg Arg Leu Val His Arg Asp Leu Ala Ala Arg Asn Val Leu Val Lys
385                 390                 395                 400
Thr Pro Gln His Val Lys Ile Thr Asp Phe Gly Arg Ala Lys Leu Leu
                405                 410                 415
Gly Ala Glu Glu Lys Glu Tyr His Ala Glu Gly Gly Lys Val Pro Ile
                420                 425                 430
```

```
Lys Trp Met Ala Leu Glu Ser Ile Leu His Arg Ile Tyr Thr His Gln
            435                 440                 445

Ser Asp Val Trp Ser Tyr Gly Val Thr Val Trp Glu Leu Met Thr Phe
        450                 455                 460

Gly Ser Lys Pro Tyr Asp Gly Ile Pro Ala Ser Glu Ile Ser Ser Ile
465                 470                 475                 480

Leu Glu Lys Gly Glu Arg Leu Pro Gln Pro Pro Ile Cys Thr Ile Asp
                485                 490                 495

Val Tyr Met Ile Met Val Lys Cys Trp Met Ile Asp Ala Asp Ser Arg
            500                 505                 510

Pro Lys Phe Arg Glu Leu Ile Ile Glu Phe Ser Lys Met Ala Arg Asp
        515                 520                 525

Pro Gln Arg Tyr Leu Val Ile Gln Gly Asp Glu Arg Met His Leu Pro
    530                 535                 540

Ser Pro Thr Asp Ser Asn Phe Tyr Arg Ala Leu Met Asp Glu Glu Asp
545                 550                 555                 560

Met Asp Asp Val Val Asp Ala Asp Glu Tyr Leu Ile Pro Gln Gln Gly
                565                 570                 575

Phe Phe Ser Ser Pro Ser Thr Ser Arg Thr Pro Leu Leu Ser Ser Leu
            580                 585                 590

Ser Ala Thr Ser Asn Asn Ser Thr Val Ala Cys Ile Asp Arg Asn Gly
        595                 600                 605

Leu Gln Ser Cys Pro Ile Lys Glu Asp Ser Phe Leu Gln Arg Tyr Ser
    610                 615                 620

Ser Asp Pro Thr Gly Ala Leu Thr Glu Asp Ser Ile Asp Asp Thr Phe
625                 630                 635                 640

Leu Pro Val Pro Glu Tyr Ile Asn Gln Ser Val Pro Lys Arg Pro Ala
                645                 650                 655

Gly Ser Val Gln Asn Pro Val Tyr His Asn Gln Pro Leu Asn Pro Ala
            660                 665                 670

Pro Ser Arg Asp Pro His Tyr Gln Asp Pro His Ser Thr Ala Val Gly
        675                 680                 685

Asn Pro Glu Tyr Leu Asn Thr Val Gln Pro Thr Cys Val Asn Ser Thr
    690                 695                 700

Phe Asp Ser Pro Ala His Trp Ala Gln Lys Gly Ser His Gln Ile Ser
705                 710                 715                 720

Leu Asp Asn Pro Asp Tyr Gln Gln Asp Phe Phe Pro Lys Glu Ala Lys
                725                 730                 735

Pro Asn Gly Ile Phe Lys Gly Ser Thr Ala Glu Asn Ala Glu Tyr Leu
            740                 745                 750

Arg Val Ala Pro Gln Ser Ser Glu Phe Ile Gly Ala
        755                 760
```